(12) United States Patent
Sareen et al.

(10) Patent No.: US 11,767,513 B2
(45) Date of Patent: Sep. 26, 2023

(54) NEUROMUSCULAR JUNCTION

(71) Applicant: CEDARS-SINAI MEDICAL CENTER, Los Angeles, CA (US)

(72) Inventors: Dhruv Sareen, Porter Ranch, CA (US); Berhan Mandefro, Sherman Oaks, CA (US); Anjoscha Kaus, Los Angeles, CA (US)

(73) Assignee: Cedars-Sinai Medical Center, Los Angeles, CA (US)

(*) Notice: Subject to any disclaimer, the term of this patent is extended or adjusted under 35 U.S.C. 154(b) by 396 days.

(21) Appl. No.: 16/492,906

(22) PCT Filed: Mar. 14, 2018

(86) PCT No.: PCT/US2018/022511
§ 371 (c)(1),
(2) Date: Sep. 10, 2019

(87) PCT Pub. No.: WO2018/170180
PCT Pub. Date: Sep. 20, 2018

(65) Prior Publication Data
US 2020/0071673 A1 Mar. 5, 2020

Related U.S. Application Data

(63) Continuation-in-part of application No. 15/458,185, filed on Mar. 14, 2017.

(60) Provisional application No. 62/471,273, filed on Mar. 14, 2017.

(51) Int. Cl.
| | | |
|---|---|---|
| *C12N 5/077* | (2010.01) | |
| *C12N 5/074* | (2010.01) | |
| *C12N 5/073* | (2010.01) | |
| *C12N 5/00* | (2006.01) | |
| *C12N 5/071* | (2010.01) | |
| *C12N 5/0793* | (2010.01) | |

(52) U.S. Cl.
CPC ......... *C12N 5/0658* (2013.01); *C12N 5/0068* (2013.01); *C12N 5/0603* (2013.01); *C12N 5/0619* (2013.01); *C12N 5/0696* (2013.01); *C12N 5/0697* (2013.01); *C12N 2501/105* (2013.01); *C12N 2501/115* (2013.01); *C12N 2501/12* (2013.01); *C12N 2501/999* (2013.01); *C12N 2506/02* (2013.01); *C12N 2506/45* (2013.01); *C12N 2533/50* (2013.01)

(58) Field of Classification Search
CPC .................................................. C12N 5/0697
See application file for complete search history.

(56) References Cited

U.S. PATENT DOCUMENTS

| | | | |
|---|---|---|---|
| 6,300,080 B1 | 10/2001 | Brenner et al. | |
| 7,989,197 B2 | 8/2011 | Yoo et al. | |
| 8,647,861 B2 | 2/2014 | Ingber et al. | |
| 9,790,470 B2 | 10/2017 | Vallier et al. | |
| 10,174,289 B2 | 1/2019 | Wells et al. | |
| 11,326,149 B2 | 5/2022 | Kerns et al. | |
| 2004/0247571 A1 | 12/2004 | Meijer et al. | |
| 2007/0077649 A1 | 4/2007 | Sammak et al. | |
| 2007/0128722 A1 | 6/2007 | Lin | |
| 2007/0281353 A1 | 12/2007 | Vacanti et al. | |
| 2008/0044847 A1 | 2/2008 | Shusta et al. | |
| 2008/0132445 A1 | 6/2008 | Ormandy et al. | |
| 2008/0305086 A1 | 12/2008 | Poole | |
| 2009/0075374 A1 | 3/2009 | Palecek et al. | |
| 2009/0123383 A1 | 5/2009 | Frangioni | |
| 2009/0258337 A1 | 10/2009 | Yagi | |
| 2009/0317852 A1 | 12/2009 | Parker et al. | |
| 2009/0324559 A1 | 12/2009 | Sakurada et al. | |
| 2011/0097796 A1 | 4/2011 | Loa | |
| 2011/0111499 A1 | 5/2011 | Torihashi | |
| 2011/0245307 A1 | 10/2011 | Alkon | |
| 2011/0250585 A1 | 10/2011 | Ingber et al. | |
| 2012/0094381 A1 | 4/2012 | Chambers et al. | |
| 2012/0107934 A1 | 5/2012 | Poole | |
| 2012/0128655 A1 | 5/2012 | Kim et al. | |
| 2012/0171354 A1 | 7/2012 | O'Neill et al. | |
| 2012/0211373 A1 | 8/2012 | El-Sayed et al. | |
| 2013/0137130 A1 | 5/2013 | Wells et al. | |
| 2013/0224857 A1 | 8/2013 | Blak et al. | |
| 2013/0280802 A1 | 10/2013 | Schulz et al. | |

(Continued)

FOREIGN PATENT DOCUMENTS

| | | |
|---|---|---|
| AU | 2015204375 A1 | 8/2015 |
| AU | 2016341880 A1 | 5/2018 |

(Continued)

OTHER PUBLICATIONS

Lenzi (2016, Stem Cell Res, 17:140-147).*
Burkhardt (2013, Mol Cell Neurosci, 56:355-364).*
Ionescu (2016, European Journal of Cell Biology, 95:69-88).*
ISR-WO—for PCT/US2019/026193 dated Jul. 1, 2019, 8 pages.
International Search Report and Written Opinion of PCT/US2019/26183, dated Jun. 12, 2019, 10 Pages.
Sundberg, m. et al., Improved cell therapy protocol for Parkinson's Disease based on differentiation efficiency and safety of Hesc-, Hipsc and non-human primate Ipsc-derived DA neurons, Stem Cells, 2013, 31:8, pp. 1-25.

(Continued)

*Primary Examiner* — Valarie E Bertoglio
(74) *Attorney, Agent, or Firm* — Nixon Peabody LLP

(57) ABSTRACT

The invention relates to culturing motor neuron cells together with skeletal muscle cells in a fluidic device under conditions whereby the interaction of these cells mimic the structure and function of the neuromuscular junction (NMJ) providing a NMJ-on-chip. Good viability, formation of myo-fibers and function of skeletal muscle cells on fluidic chips allow for measurements of muscle cell contractions. Embodiments of motor neurons co-cultures with contractile myo-fibers are contemplated for use with modeling diseases affecting NMJ's, e.g. Amyotrophic lateral sclerosis (ALS).

16 Claims, 34 Drawing Sheets

(56) References Cited

U.S. PATENT DOCUMENTS

| | | | |
|---|---|---|---|
| 2013/0288969 A1 | 10/2013 | Scadden | |
| 2014/0038279 A1 | 2/2014 | Ingber et al. | |
| 2014/0065660 A1 | 3/2014 | Hanseup et al. | |
| 2014/0093905 A1 | 4/2014 | Ingber et al. | |
| 2014/0134732 A1 | 5/2014 | Ashton | |
| 2014/0142370 A1 | 5/2014 | Wong et al. | |
| 2014/0171380 A1 | 6/2014 | Kim et al. | |
| 2014/0199700 A1 | 7/2014 | Kume et al. | |
| 2014/0248621 A1 | 9/2014 | Collins | |
| 2014/0288093 A1 | 9/2014 | Krainc et al. | |
| 2014/0315990 A1 | 10/2014 | Alkon et al. | |
| 2014/0329321 A1 | 11/2014 | Rajesh et al. | |
| 2014/0342445 A1 | 11/2014 | Ingber et al. | |
| 2015/0017674 A1 | 1/2015 | Christensen et al. | |
| 2015/0023928 A1 | 1/2015 | Hassiotou | |
| 2015/0037320 A1 | 2/2015 | McGrath et al. | |
| 2015/0151011 A1 | 6/2015 | Jang et al. | |
| 2015/0218522 A1 | 8/2015 | Peterson et al. | |
| 2015/0232810 A1 | 8/2015 | Luo et al. | |
| 2015/0252328 A1 | 9/2015 | Woodruff et al. | |
| 2015/0258124 A1 | 9/2015 | Katajisto et al. | |
| 2015/0265652 A1 | 9/2015 | George et al. | |
| 2015/0329828 A1 | 11/2015 | Rezania | |
| 2016/0145642 A1 | 5/2016 | Cui et al. | |
| 2016/0152950 A1 | 6/2016 | Zhang et al. | |
| 2016/0175401 A1 | 6/2016 | Spiegelman et al. | |
| 2017/0107498 A1 | 4/2017 | Sareen et al. | |
| 2017/0226478 A1 | 8/2017 | Kerns et al. | |
| 2017/0240866 A1 | 8/2017 | Wells et al. | |
| 2017/0253856 A1 | 9/2017 | Douvaras et al. | |
| 2017/0283772 A1 | 10/2017 | Qian et al. | |
| 2017/0292116 A1 | 10/2017 | Erlls et al. | |
| 2017/0313976 A1 | 11/2017 | Kuwahara et al. | |
| 2018/0021383 A1 | 1/2018 | George et al. | |
| 2018/0057788 A1 | 3/2018 | Kerns et al. | |
| 2018/0237741 A1 | 8/2018 | Gazit et al. | |
| 2018/0298331 A1 | 10/2018 | Kerns et al. | |
| 2018/0298332 A1 | 10/2018 | Kerns et al. | |
| 2018/0305651 A1 | 10/2018 | Kerns et al. | |
| 2018/0305668 A1 | 10/2018 | Gazit et al. | |
| 2019/0009270 A1 | 1/2019 | Gazit et al. | |
| 2019/0018000 A1 | 1/2019 | Gazit et al. | |
| 2019/0031992 A1 | 1/2019 | Kerns et al. | |
| 2019/0153395 A1 | 5/2019 | Barrett et al. | |
| 2019/0194606 A1 | 6/2019 | Vatine et al. | |
| 2019/0359924 A1 | 11/2019 | Kerns et al. | |
| 2020/0000267 A1 | 1/2020 | Zuidervaart et al. | |
| 2020/0002671 A1 | 1/2020 | Qu et al. | |
| 2020/0032215 A1 | 1/2020 | Svendsen et al. | |
| 2020/0071673 A1 | 3/2020 | Sareen et al. | |
| 2020/0157508 A1 | 5/2020 | Barrett et al. | |
| 2021/0000880 A1 | 1/2021 | Svendsen et al. | |
| 2021/0023039 A1 | 1/2021 | Laperle et al. | |
| 2021/0024886 A1 | 1/2021 | Laperle et al. | |
| 2021/0033628 A1 | 2/2021 | Laperle et al. | |
| 2021/0130774 A1 | 5/2021 | Sances et al. | |
| 2023/0159896 A1 | 5/2023 | Sharma et al. | |

FOREIGN PATENT DOCUMENTS

| | | |
|---|---|---|
| AU | 2017213795 A1 | 8/2018 |
| AU | 2017214468 A1 | 9/2018 |
| AU | 2017319168 A1 | 3/2019 |
| AU | 2017321489 A1 | 3/2019 |
| AU | 2018235950 A1 | 10/2019 |
| AU | 2018236273 A1 | 10/2019 |
| AU | 2018270270 A1 | 12/2019 |
| AU | 2017319168 B2 | 4/2021 |
| AU | 2016341880 B2 | 5/2021 |
| CA | 3002399 A1 | 4/2017 |
| CA | 3013337 A1 | 8/2017 |
| CA | 3013357 A1 | 8/2017 |
| CA | 3034614 A1 | 3/2018 |
| CA | 3035058 A1 | 3/2018 |
| CA | 3055992 A1 | 9/2018 |
| CA | 3056089 A1 | 9/2018 |
| CA | 3064086 A1 | 11/2018 |
| EP | 3008168 A1 | 4/2016 |
| EP | 3031908 A1 | 6/2016 |
| EP | 3365424 | 8/2018 |
| EP | 3411470 A2 | 12/2018 |
| EP | 3411472 A1 | 12/2018 |
| EP | 3503901 A1 | 7/2019 |
| EP | 3504319 A1 | 7/2019 |
| EP | 3625331 A1 | 3/2020 |
| EP | 3768823 | 1/2021 |
| EP | 3775161 | 2/2021 |
| EP | 3787613 | 3/2021 |
| EP | 3787649 A1 | 3/2021 |
| EP | 4048282 | 8/2022 |
| GB | 2561312 A | 10/2018 |
| GB | 2562406 A | 11/2018 |
| GB | 2564582 A | 1/2019 |
| GB | 2568446 A | 5/2019 |
| GB | 2569058 A | 6/2019 |
| GB | 2574988 A | 12/2019 |
| GB | 2575574 A | 1/2020 |
| GB | 2561312 B | 3/2021 |
| GB | 2564582 B | 9/2021 |
| HK | 1260726 B2 | 7/2021 |
| JP | 2014-171434 A | 9/2014 |
| JP | 2014171434 | 9/2014 |
| JP | 2015-504676 A | 2/2015 |
| JP | 2015504676 | 2/2015 |
| JP | 2018533940 A | 11/2018 |
| JP | 2019506861 A | 3/2019 |
| JP | 2021-520784 A1 | 8/2021 |
| JP | 2021-523700 A | 9/2021 |
| JP | 2021-523888 A | 9/2021 |
| KR | 20180069882 A | 6/2018 |
| KR | 10-2022-0084282 | 6/2022 |
| SG | 11201803143Y A | 5/2018 |
| SG | 11201901621V A | 3/2019 |
| SG | 11201901628X A | 3/2019 |
| SG | 11201908358P A | 10/2019 |
| SG | 11201908359U A | 10/2019 |
| WO | 2000053218 | 9/2000 |
| WO | 2005021720 A2 | 3/2005 |
| WO | WO 2005/021720 A2 | 3/2005 |
| WO | WO 2010009307 A2 | 1/2010 |
| WO | WO 2010/108005 A2 | 9/2010 |
| WO | 2011109440 A1 | 9/2011 |
| WO | 2012/100084 A1 | 7/2012 |
| WO | WO 2012/118799 A2 | 9/2012 |
| WO | 2013/056216 A1 | 4/2013 |
| WO | 2013/071282 A1 | 5/2013 |
| WO | WO 2013/065763 A1 | 5/2013 |
| WO | 2013/086486 A1 | 6/2013 |
| WO | 2013106677 A1 | 7/2013 |
| WO | 2013/184193 A1 | 12/2013 |
| WO | 2014159356 A1 | 10/2014 |
| WO | WO 2014/172682 A1 | 10/2014 |
| WO | WO 2014/176606 A1 | 10/2014 |
| WO | WO 2015/052143 A1 | 4/2015 |
| WO | WO 2015/057261 A1 | 4/2015 |
| WO | WO 2015/126528 A1 | 8/2015 |
| WO | 2015143342 A1 | 9/2015 |
| WO | WO 2015/138032 A2 | 9/2015 |
| WO | WO 2015/138034 A2 | 9/2015 |
| WO | WO 2015/163823 A1 | 10/2015 |
| WO | WO 2015153451 A1 | 10/2015 |
| WO | WO 2015/181253 A1 | 12/2015 |
| WO | WO 2015/183920 A2 | 12/2015 |
| WO | WO 2015/188131 A1 | 12/2015 |
| WO | 2016/061464 A1 | 4/2016 |
| WO | 016063985 A1 | 4/2016 |
| WO | 2016061464 A1 | 4/2016 |
| WO | WO 2016/086040 A1 | 6/2016 |
| WO | WO 2016/093222 A | 6/2016 |
| WO | 2016/141137 A1 | 9/2016 |
| WO | 2016162747 A2 | 10/2016 |
| WO | 2016183252 A1 | 11/2016 |
| WO | WO 2017/035119 A1 | 3/2017 |
| WO | WO 2017/070224 A1 | 4/2017 |

(56) References Cited

FOREIGN PATENT DOCUMENTS

| | | |
|---|---|---|
| WO | 2017075271 A1 | 5/2017 |
| WO | 2017078807 A1 | 5/2017 |
| WO | WO 2017/075271 A1 | 5/2017 |
| WO | 2017/112455 A1 | 6/2017 |
| WO | WO 2017/123806 A1 | 7/2017 |
| WO | WO 2017/136462 A2 | 8/2017 |
| WO | WO 2017/136479 A1 | 8/2017 |
| WO | WP 2017/143049 A1 | 8/2017 |
| WO | WO 2017/200486 A1 | 11/2017 |
| WO | 2017/219000 A1 | 12/2017 |
| WO | 2018/035214 A1 | 2/2018 |
| WO | WO 2018/044885 A1 | 3/2018 |
| WO | WO 2018/044934 A1 | 3/2018 |
| WO | 2018/140647 A1 | 8/2018 |
| WO | 2018/176001 A2 | 9/2018 |
| WO | WO 2018/170139 A1 | 9/2018 |
| WO | WO 2018/170180 A1 | 9/2018 |
| WO | WO 2018/213773 A1 | 11/2018 |
| WO | 2019/122291 A1 | 6/2019 |
| WO | 2019/178550 A1 | 9/2019 |
| WO | WO 2019/183597 A1 | 9/2019 |
| WO | 2019195798 A1 | 10/2019 |
| WO | 2019195800 A1 | 10/2019 |
| WO | WO 2019/195798 A1 | 10/2019 |
| WO | 2019212690 A1 | 11/2019 |
| WO | 2019212691 A1 | 11/2019 |
| WO | 2021/081229 A1 | 4/2021 |
| WO | 2021/081237 A1 | 4/2021 |
| WO | 2021222724 A1 | 11/2021 |

OTHER PUBLICATIONS

Chou, B.K. et al., Efficient human iPS cell derivation by a non-integrating plasmid from blood cells with unique epigenetic and gene eIDS filed Oct. 3, 2020pression signatures, Cell Research, 2011, 21:3, pp. 518-529.

Kilpatrick, K. et al., Genetic and chemical activation of TFEB mediates clearance of aggregated a-synuclein, PLoS One, 2015, 10:3, pp. 1-21.

Li, Y. et al., Protein kinase C controls lysosome biogenesis independently of mTORC1, Nature Cell Biology, 2016, 10:10, pp. 1-26.

Lee et al. Microfluidic 3D bone tissue model for high-throughput evaluation of would healing and infection-preventing biomaterials, Biomaterials 33.4 2012 999-1006.

JP Notice of Reasons for Rejection dated Mar. 1, 2021.

Extended European Search Report for EP 18802136.4 dated Jan. 22, 2021, 12 pages.

Kuratnik et al., Intestinal organoids at tissue surrogates for toxicological and pharmacological studies, biochemical Pharmacology, Apr. 25, 2013, vol. 85:12, pp. 1721-1726.

Workman et al., Intestine-Chip: A new model to understand the role of the Intestinal Epithelium in IBD by combining Microengineering Technology and IPSC-Derived human intestinal organoids, Gastroenterology, Apr. 1, 2017, vol. 152:5, Abstract only.

Written Opinion 11201901628X dated Mar. 10, 2021, 9 pages.

Amoroso M. W. et al., Accelerated High-Yield Generation of Limb-Innervating Motor Neurons from Human Stem Cells. J Neurosci, Jan. 9, 2013, vol. 33, No. 2, pp. 574-586 pp. 575 and 578, Fig. 1 and 2.

Faravelli I. et al., Motor neuron derivation from human embryonic and induced pluripotent stem cells: Experimental approaches and clinical perspectives. Stem Cell Res Ther, Jul. 14, 2014, vol. 5, No. 4, pp. 87.

Jha et al., Motor Neuron differentiation from Pluripotent Stem Cells and Other Intermediate Proliferative Precursors that can be Discriminated by Lineage Specific Reports, Stem Cell Rev Rep, Aug. 2014, 11:194-204.

International Search Report and Written Opinion of PCT/US2019/26178, dated Jun. 11, 2019, 14 Pages.

ISR-WO—for PCT/US2019/026195 dated Jun. 12, 2019, 10 pages.

Kondo, T. et al., Ipsc-based Coound screening and in vitro trials identify a synergistic anti-amyloid b combination for Alzheimer's Disease, Cell Reports, 2017, vol. 21, pp. 2304-2312.

McKinney, C.E. et al., Using induced pluripotent stem cells derived neurons to model brain diseases, Neural Regeneration Research, 2017, 12:7 pp. 1-11.

EP 19771249.0 Partial Supplemental European Search Report dated Nov. 8, 2011, 15 pages.

EP 18802136.4 Examination Report dated Oct. 14, 2021, 8 pages.

Abbott et al., Structure and function of the blood-brain barrier, Neurobiology of Desease, 2010 27:13-25.

Abbott et al., Structure and function of the blood-brain barrier, Pharm Tox BBB: Feb. 1-3, 2010, Conf. Abstract.

Demers et al., Development-on-Chip: in vitro Neutral Tube Patterning with a Microfluidic Device, Development, 2016, vol. 143(11), pp. 1884-1892.

Kauffman et al., Alternative functional in vitro models of human intestinal epithelia, frontiers in Pharmacology, Jul. 2013, vol. 4, Article 79, 18 pages.

Kelamangalath et al. k-Opioid receptor inhibition of calcium oscillations in spinal cord neurons,, Molecular Pharmacology, 2011, 79:1061-1071.

Kwasny et al., Static biofilm cultures of gram-positive pathogens grown in a microtiter format used for anti-biofilm drug discovery, Current Protocols in Pharmacology, 2010, 13A.8.1-13A.8.23.

Loo et al., An Arduous Journey from Human Pluripotent Stem Cells to Functional Pancreatic Beta Cells, Diabetes Obes Metab., 2018, vol. 20(3), pp. 3-13.

McGaugh et al., Efficient Differentiation of Pluripotent Stem Cells to NKX6-1 + Pancreating Progenitors, Journal of Visualized Experiments, 2017, vol. 121, pp. 1-5.

Naik et al., In vitro blood-brain models: Current and perspective technologies, J. Phar Sci., 2012, 1014(4):1337-1354.

Perry et al., The Neuromuscular junction: Structure and function, downloaded from the internet (Neuromuscular junction: Parts, structure and steps/Kenhub>, pp. 1-6, downloaded Feb. 25, 2021.

Polydimethylsiloxane—Wikipedia, dowloaded on Feb. 24, 2021 <Silicon dioxide—Wikipedia>, pp. 1-11.

Ryan et al., Progranulin is expressed within motor neurons and promotes neuronal cell survival, BMC Neuroscience, 2009, 10:130, pp. 1-22.

Sances et al., Modeling ALS with Motor Neurons Derived from Human Induced Pluripotent Stem Cells, Nature Neuroscience , 2016, vol. 19, pp. 542-553.

Santaguida et al., Side By Side Comparison Between Dynamic Versus Static Models of Blood-Brain-Barrier in vitro: A Permeability Study, Brain Research, 2006, vol. 1109(1), pp. 1-13.

Schiesser et al., Derivation of Insulin-Producing Beta-Cells from Human Pluripotent Stem Cells, The Review of Diabetic Studies, 2014, vol. 11(1), pp. 6-18.

Schwartz et al., Allan-Herndon-Dudley Syndrome and the Monocarboxylate Transporter 8 (MCT8) Gene, 2005, AJHG, vol. 77(1), pp. 41-53.

Silicon dioxide—Wikipedia, downloaded on Feb. 24, 2021 <silicon dioxide—Wikipedia> pp. 1-20.

Southam et al., Microfluidic primary culture model of the lower motor neuron-neuromuscular junction circuit, J Neurosc Meth 2013, 218:164-169.

Southam et al., A Novel in vitro Primary Culture Model of the Lower Motor Neuron—Nueromuscular Junction Circuit, Microfludic and Compartmentalized Platforms for Neurobiological Research, Humana Press, 2015, pp. 181-193, abstract only.

Uzei et al., Microfluidic Device for the Formation of Optically Excitable, Three-Dimensional, Compartmentalized Motor Units, Science Advances, 2016, pp. e1501429.

Wang et al., Microfluidics: A new cosset for neurobiology, Lab Chip, 2009, 9:644-652.

Wang et al., Generation of an Induced Pluripotent Stem Cell Line (SHCDNi003-A) from a One-Year Old Chinese Han Infant with Allan-Herndon-Dudley Syndrome, Stem Cell Research, 2020, vol. 46, 4 pages.

Yang et al., From the vascular microenvironment to neurogenesis, Brain Res Bull. Jan. 15, 2011; 84(1):1-7.

(56) References Cited

OTHER PUBLICATIONS

International Search Report and Written Opinion of PCT Application No. PCT/US2017/013250, dated Mar. 31, 2017, 12 Pages.
International Search Report and Written Opinion of PCT Application No. PCT/US2016/057724, dated Jan. 9, 2017, 17 Pages.
International Search Report and Written Opinion of PCT/US2017/016098, dated Jun. 22, 2017, 14 Pages.
International Search Report and Written Opinion of PCT/US2017/016079, dated Jul. 25, 2017, 26 Pages.
International Search Report and Written Opinion of PCT/US2017/049193, dated Nov. 6, 2017, 9 Pages.
International Search Report and Written Opinion of PCT/US2017/049115, dated Nov. 28, 2017, 11 Pages.
International Search Report and Written Opinion of PCT/US2018/022511, dated Jul. 26, 2018, 11 Pages.
International Search Report and Written Opinion of PCT/US2018/033498, dated Aug. 9, 2018, 9 Pages.
International Search Report and Written Opinion for PCT/US2018/022455 dated Aug. 23, 2018, 13 pages.
International Preliminary Report on Patentability for PCT/US2016/057724 dated Apr. 24, 2018, 15 pages.
International Preliminary Report on Patentability for PCT/US2017/013250 dated Jul. 17, 2018, 7 pages.
International Preliminary Report on Patentability for PCT/US2017/016098 dated Aug. 7, 2018, 10 pages.
International Preliminary Report on Patentability for PCT/US2017/016079 dated Aug. 7, 2018, 21 pages.
International Preliminary Report on Patentability for PCT/US2018/022511 dated Sep. 17, 2019, 8 pages.
International Preliminary Report on Patentability for PCT/US2018/022455 dated Aug. 23, 2018, 9 pages.
International Preliminary Report on Patentability for PCT/US2018/033498 dated Nov. 19, 2019, 8 pages.
International Preliminary Report on Patentability for PCT/US2017/049193 dated Mar. 5, 2019, 8 pages.
International Preliminary Report on Patentability for PCT/US2017/049115 dated Mar. 5, 2019, 8 pages.
International Search Report and Written Opinion of PCT/US2019/023749, dated Jun. 25, 2019, 12 Pages.
AU 2016341880 Examination Report dated Jan. 15, 2020, 5 pages.
AU 2017214468 Examination Report dated Dec. 10, 2019, 5 pages.
CA 3034614 Examination Report dated Jul. 5, 2019, 5 pages.
EP 16858141.1 Extended Search Report dated Mar. 15, 2019, 10 pages.
EP 17748100.9 European Partial Supplementary Search Report dated Sep. 18, 2019, 15 pages.
EP 17748100.9 European Extended Search Report dated Dec. 20, 2019, 12 pages.
EP 17748084.5 European Extended Search Report dated Sep. 10, 2019.
EP 17847396.3 European Extended Search Report dated, Jan. 28, 2020, 11 pages.
EP17847365.8 European Extended Search Report dated Jan. 21, 2020, 11 pages.
GB1811716.8 Examination Report dated Feb. 12, 2020, 6 pages.
GB 1903007.1 Search Report dated Apr. 1, 2019, 8 pages.
SG 11201803143Y Search Report dated Jul. 15, 2019, 3 pages.
Action Potential, Wikipedia, pp. 1-29 Downloaded on Apr. 28, 2019, https://en.wikipedia.org/wiki/Action_potential.
Adriani et al., Modeling the Blood-Brain Barrier in a 3D Triple Co-Culture Microfluidic System, 37th Annual International Conference of the IEEE Engineering in Medicine and Biology Society, IEEE, pp. 338-341.
Armstrong et al., Human Induced Pluripotent Stem Cell Lines Show Stress Defense Mechanisms and Mitochondrial Regulation Similar to Those of Human Embryonic Stem Cells, 2010, Stem Cells, vol. 28(4), pp. 661-673.
Barrett et al., Reliable Generation of Induced Pluripotent Stem Cells from Human Pymphoblastoid Cell Lines, 2014, Stem Cells Translational Medicine, vol. 3, pp. 1429-1434.
Ben-Zvi et al., Modeling Human Nutrition Using Human Embryonic Stem Cells, Cell, 2015, vol. 161(1), pp. 12-17.
Bhatia et al., Microfluidic Organs-on-Chips, Nature Biotechnology, 2014, vol. 32(8), pp. 760-772.
Booth, Ross Hunter, A Microfluidic in Vitro Model of the Blood-Brain Barrier, Dissertation, 2014, pp. 1-177.
Boyer et al., More than a Bystander: The Contributions of Intrinsic Skeletal Muscle Defects in Motor Neuron Diseases, 2013, Frontiers in Physiology, vol. 4, Article 356, pp. 1-12.
Brown et al., Recreating Blood-Brain Barrier Physiology and Structure on Chip: A Novel Neurovascular Microfluidic Bioreactor, 2015, Biomicrofluidics, vol. 9(5).
Cashman et al., Induced Pluripotent Stem Cells and Motor Neuron Disease: Toward an Era of Individualized Medicine, J. Neurosci, 2013, vol. 33, pp. 8587-8589.
Chal et al., Differentiation of Pluripotent Stem Cells to Muscle Fiber to Model Duchenne Muscular Dystrophy, 2015, Nature Biotechnology, vol. 33(9), pp. 962-969.
Chen et al., Surface Marker Epithelial Cell Adhesion Molecule and E-Cadherin Facilitate the Identification and Selection of Induced Pluripotent Stem Cells, 2011, Stem Cell Rev., vol. 7(3), pp. 722-735.
Date et al., Mini-Gut Organoids: Reconstruction of the Stem Cell Niche, Annu. Rev. Cell Dev. Biol., 2015, vol. 31, pp. 269-289.
Dhumpa et al., Temporal Gradients in Microfluidic Systems to Probe Cellular Dynamics: A Review, Anal. Chim. Acta, 2012, vol. 743, pp. 9-18.
Dimos et al., Induced Pluripotent Stem Cells Generated from Patients with ALS can be Differentiated into Motor Nuerons, Science, 2008, vol. 321, pp. 1218-1221.
Douville et al., Fabrication of Two-Layered Channel System with Embedded Electrodes to Measure Resistance Across Epithelial and Endothelial Barriers, 2010, Analytical Chemistry, vol. 82(6), pp. 2505-2511.
Ebert et al., EZ Spheres: A Stable and Expandable Culture System for the Generation of Pre-rosette Multipotent Stem Cells from Human ESCs and iPSCs., 2013, Stem Cell Research, vol. 10(3), pp. 417-427.
Esch et al., Organs-on-Chips at the Frontiers of Drig Discovery, Nature Reviews, 2015, vol. 14(4), pp. 248-269.
Evans et al., The Development of a Method for the Preparation of Rat Intestinal Epithelial Cell Primary Cultures, 1992, Journal of Cell Science, vol. 101, pp. 219-231.
Gao et al., Regulation of Cell Migration and Osteogenic Differentiation in Mesenchymal Stem Cells under Extremely Low Fluidic Shear Stress, Biomicrofluidics, 2014, vol. 8(5), Article No. 052008.
Gel, Wikipedia, pp. 1-29 Downloaded on Sep. 14, 2018, https://en.wikipedia.org/wiki/Gel.
Gracz et al., CD24 and CD44 Mark Human Intestinal Epithelial Cell Populations with Characteristics of Active and Facultative Stem Cells, 2013, Stem Cells, vol. 31(9), pp. 2024-2030.
Gross et al., Applications of Microfluidics for Neuronal Studies, 2007, Journal of the Neurological Sciences, vol. 252, pp. 135-143.
Hu et al. Neural differentiation of human induced pluripotent stem cells follows developmental principles but with variable potency, PNAS, 2010, vol. 107(9), pp. 4335-4340.
Hu et al., Derivation, Expansion and Motor Neuron Differentiation of Human-Induced Pluripotent Stem Cells with Non-Integrating Episomal Vectors and a Defined Xenogeneic-Free Culture System, Mol Neurobiol, 2016, vol. 53, pp. 1589-1600.
Hughes et al., Matrigel: A Complex Protein Mixture Required for Optimal Growth of Cell Culture, 2010, Proteomics, vol. 10, pp. 1886-1890.
Huh et al., From 3D Cell Culture to Organs-on-Chips, Trends in Cell Biology, 2011, vol. 21(2), pp. 745-754.
Huh et al., Microfabrication of Human Organs-on-Chips, Nature Protocols, 2013, vol. 8(11), pp. 2135-2157.
Hynds et al., Concise Review: The Relevance of Human Stem Cell-Derived Organoid Models for Epithelial Transitional Medicine, Stem Cells, 2013, vol. 1 31, pp. 417-422.
Jang et al., JAK-STAT Pathway and Myogenic Differentiation, JAKSTAT, 2013, vol. 2(2), pp. e23282-1 to e-23282-6.

(56) References Cited

OTHER PUBLICATIONS

Joo-Eun, L., Patient-Specific Induced Pluripotent Stem Cell Models of Variant Angina Derived from Peripheral Blood, The Department of Biomedical Sciences Seoul National University College of Medicine, Jul. 2017, pp. 1-75.

Kilic et al., Brain-on-a-Chip Model Enables Analysis of Human Neuronal Differentiation and Chemotaxis, 2016, Lab on a Chip, vol. 16(21), pp. 4152-4162.

Kim et al., Human Gut-on-a-Chip Inhabited by a Microbial Flora that Experiences Intestinal Peristalsis-Like Motions and Flow, Lab on a Chip, 2012, vol. 12(12). pp. 2165.

Kim et al., Gut-on-a-Chip Microenvironmental Induces Human Intestinal Cells to Undergo Villus Differentiation, Integrative Biology, 2013, vol. 5(9), p. 1130-1140.

Kim et al., Contributions of Microbiome and Mechanical Deformation to Intestinal Bacterial Overgrowth and Inflammation in a Human Gut-on-a-Chip, PNAS, 2015, vol. 113(1), pp. E7-E15.

Kirkby et al., A Role for Correlated Spontaneous Activity in the Assembly of Neural Circuits, 2013, Neuron, vol. 80(5), 27 Pages.

Lenner, J., Fat Cells More Easily Programmed into iPS Cells, 2009, pp. 1-2.

Lin et al., Neural Stem Cell Differentiation in a Cell-Collagen-Bioreactor Culture System, 2004, Developmental Brain Research, vol. 153, pp. 163-173.

Lippmann, et al., Human Blood-Brain Barrier Endothelial Cells Derived from Pluripotent Stem Cells, 2012, Nature Biotechnology, vol. 30(8), pp. 783-791.

Lippmann et al., A Retinoic Acid-Enhanced, Multicellular Human Blood-Brain Barrier Model Derived from Stem Cell Sources, Scientific Reports, vol. 4(1), 2014, pp. 1-10.

Lippmann et al., Chemically Defined Differentiation of Human Pluripotent Stem Cells to Hindbrain and Spinal Cord Neural Stem Cells with Defined Regional Identifies, 2015, Protocol Exchange.

Martin et al., Laparoscopic Colorectal Resection in the Obese Patient, 2011, Clinics in Colon and Rectal Surgery, vol. 24(4), pp. 263-273.

Massumi et al., Efficient Programming of Human Eye Conjunctiva-Derived Induced Pluripotent Stem (ECiPS) Cells into Definitive Endoderm-Like Cells, Experimental Cell Research, 2014, vol. 322, pp. 51-61.

Medical Dictionary—Myotube, Downloaded on Jul. 8, 2018, https://medical-dictionary.thefreedictionary.com/myotube, p. 1.

Murphy et al., Scaffolds for 3D in vitro Culture of Neural Lineage Cells, Acta Biomaterialia, 2017, vol. 54, pp. 1-20.

Nicoleau et al., Embryonic Stem Cells Neural Differentiation Qualifies the Role of Wnt/[beta]—Catenin Signals in Human Telecephalic Specification and Regionalization: Human ESC Telencephalic Differentiation, Stem Cells, 2013, vol. 31(9), pp. 1763-1774.

Niego et al., Improved Method for the Preparation of a Human Cell-based, Contact Model of the Blood-Brain Barrier, 2013, J. Vis. Exp., vol. 81(e50934), pp. 1-9.

Nostro et al., Efficient Generation of NKX6-1+ Pancreatic Progenitors from Multiple Human Pluripotent Stem Cell Lines, Stem Cell Reports, 2015 4(4), pp. 591-604.

Ochetta et al., High-Throughput Microfluidic Platform for 3D Cultures of Mesenchymal Stem Cells, Towards Engineering Developmental Processes, Scientific Reports, 2015, vol. 5, Artcle No. 10288, pp. 1-12.

Okita et al., A More Efficient Method to Generate Integration-Free Human iPS Cells, 2011, Nature Methods, vol. 8(5), pp. 409-412.

Ong et al., A Gel-Free 3D Microfluidic Cell Culture System, Biomaterials, 2008, vol. 29, pp. 3237-3244.

Park et al., Chip-Based Comparison of the Osteogenesis of Human Bone Marrow and Adipose Tissue-Derived Mesenchymal Stem Cells under Mechanical Stimulation, PLOS One, 2012, vol. 7(9), pp. 1-12.

Polini et al., Organs-on-a-Chip: A New Tool for Drug Discovery, Expert Opinion on Drug Discovery, 2014, vol. 9(4), pp. 335-352.

Prabhakarpandian et al., SyM-BBB: A Microfluidic Blood Brain Barrier Model, Lab on a Chip, 2013, vol. 13(6), p. 1093.

Qian et al., A Simple and Efficient System for Regulating Gene Expression in Human Pluripotent Stem Cells and Derivatives, Stem Cells, 2014, vol. 32(5), pp. 1230-1238.

Rajesh et al., Human Lymphoblastoid B-Cell Lines Reprogrammed to EBV-Free Induced Pluripotent Stem Cells, 2011, Blood, vol. 118(7), pp. 1797-1800.

Rhee et al., Patterned Cell Culture Inside Microfluidic Devices, Lab Chip, 2005, vol. 5(1), pp. 102-107.

Roberts et al., Expression of the Thyroid Hormone Transports Monocarboxylate Transporter-8 (SLC16A2) and Organic Ion Transporter-14 (SLCO1C1) at the Blood-Brain Barrier, Endocrinol, 2008, vol. 149(12), pp. 6251-6261.

Rosenberg et al., Calcium Signaling in Neuronal Development, 2011, Cold Spring Harb Perspect Biol., vol. 3(a004259), 13 Pages.

Sareen et al., Human Neural Progenitor Cells Generated from Induced Pluripotent Stem Cells can Survive, Migrate, and Integrate in the Rodent Spinal Cord, Journal of Comparative Neurology, 2014, vol. 522(12), pp. 2707-2728.

Sareen et al., Targeting RNA foci in iPSC-Derived Motor Neurons from ALS Patients with C90RF72 Repeat Expansion, 2013, Science Translational Medicine, vol. 5(208), 208ra149, 26 Pages.

Shimojo et al., Rapid, Efficient and Simple Motor Neuron Differentiation from Human Pluripotent Stem Cells, Moleculuar Brain, 2015, vol. 8(1), pp. 1-15.

Shimuzu et al., Microfluidic Devices for Construction of Contractile Skeletal Muscle Microtissues, J. Biosci. Bioeng., 2015, vol. 119, pp. 212-216.

Soria-Valles et al., NF-kB Activation Impairs Somatic Cell Reprogramming in Ageing, 2015, Nat. Cell Biol., vol. 17(8), pp. 1004-1013.

Stepniewski et al., Induced Pluripotent Stem Cells as a Model for Diabetes Investigation, Scientific Reports, 2015, 5:8597, 14 pages.

Telias et al., Electrical Maturation of Neurons Derived from Human Embryonic Stem Cells, F1000 Research, 2014, vol. 3(196), p. 1-12.

Tenstad et al., Extensive Adipogenic and Osteogenic Differentiation of Patterned Human Mesenchymal Stem Cells in a Microfluidic Device, Lab on a Chip, 2010, vol. 10(11), pp. 1401-1409.

Uzel et al., New Microfluidic Chip Replicates Muscle-Nerve Connection, 2016, Science Daily, pp. 1-4.

Vatine et al., Human iPSC-Derived Blood-Brain Barrier Chips Enable Disease Modeling and Personalized Medicine Applications, Cell Stem Cell, 2019, vol. 24(6), pp. 995-1005.

Vatine et al., Human iPSC-Derived Blood-Brain Barrier Chips Enable Disease Modeling and Personalized Medicine Applications,Cell Stem Cell, 2019, vol. 24, Supplemental Figures, p. 1-10.

Wang et al., Androgen Receptor-Mediated Apoptosis in Bovine Testicular Induced Pluripotent Stem Cells in Response to Phthalate Esters, 2013, Cell Death Dis., vol. 4(e907), pp. 1-11.

Wang et al., Modeling the Mitochondrial Cardiomyopathy of Barth Syndrome with Induced Pluripotent Stem Cell and Heart-on-Chip Technologies, Nature Medicine, 2014, vol. 20(6), pp. 616-623.

Watson et al., Modelling the Endothelial Blood-CNS Barriers: A Method for the Production of Robust in Vitro Models of the Rat Blood-Brain Barrier and Blood-Spinal Cord Barrier, 2013, BMC Neuroscience, vol. 14(59), pp. 1-21.

Wehkamp et al., Reduced Paneth Cell [alpha]-Defensins in Ileal Crohn's Disease, PNAS, 2005, vol. 102, pp. 18129-18134.

Workman et al., Enhanced Utilization of Induced Pluripotent Stem Cell-Derived Human Intestinal Organoids Using Microengineered Chips, CMGH Cellular and Molecular Gastroenterology and Hepatology, 2018, vol. 5(4), pp. 669-677.

Yamamoto et al., Fluid Shear Stress Induces Differentiation of Flk-1-positive Embryonic Stem Cells into Vascular Endothelial Cells in vitro., 2004, Am. J. Physiol. Heart Circ. Physiol., vol. 288, pp. 1915-1924.

Zilio et al., Universal Hydrophilic Coating of Thermoplastic Polymers Currently Used in Microfluidics, 2014, Biomed. Microdevices, vol. 16(1), pp. 107-114.

Fridley et al., Hydrodynamic modulation of pluripotent stem cells, Stem cell research & therapy,2012, vol. 45.

Zhang et al., Patient-specific 3D microfluidic tissue model for multiple myeloma, Tissue Engineering Part C: Methods, 2014, pp. 663-670.

(56) References Cited

OTHER PUBLICATIONS

Jenke et al., DNA Methylation Analysis in the Intestinal Epithelium—Effect of Cell Separation on Gene Expression an Methylation Profile, PLOS One, 2013, vol. 8(2), pp. 1-8.
Brittan et al., The gastrointestial stem cell, Cell Prolif., 2004, vol. 37, pp. 35-53.
Yamamoto et al., The Stabilization Effect of Mesenchymal Stem Cells on the Formation of Microvascular Networks in a Microfluidic Device, Journal of Biomechanical Science and Engineering, 2013, vol. 8(2).
Danmark et al., Development of a novel microfluidic device for long-term in situ monitoring of live cells in 3-dimensional matrices, Biomed Microdevices, 2012, pp. 885-893.
Yu et al., A Microfluidic-Based Multi-Shear Device for Investigating the Effects of Low Fluid-Induced Stresses on Osteoblasts, PLOS One, 2014, vol. 9(2), pp. 1-7.
GB 1903007.1 Search Report dated Jun. 24, 2020, 3 pages.
International Search Report and Written Opinion for PCT/US2020/056906 dated Mar. 16, 2021, 13 pages.
International Search Report and Written Opinion for PCT/US2018/015318 dated May 2, 2018, 16 pages.
International Search Report and Written Opinion for PCT/US2018/024198 dated Aug. 13, 2018, 15 pages.
International Search Report and Written Opinion for PCT/US2020/056896 dated Oct. 22, 2020, 11 pages.
International Preliminary Report on Patentability for PCT/US2018/015318 dated Jul. 30, 2019, 12 pages.
International Preliminary Report on Patentability for PCT/US2018/024198 dated Feb. 25, 2020, 12 pages.
EP 19782199.4 Partial Supplementary Search Report dated Nov. 30, 2021, 15 pages.
EP 19796470.3 European Extended Search Report dated Dec. 10, 2021, 11 pages.
EP 19782199.4 Extended European Search Report dated Mar. 3, 2022, 12 pages.
EP 19796911.6 Extended Search Report dated Apr. 29, 2022, 15 pages.
Akhtar et al., Inducible Expression of GDNF in Transplanted iPSC-Derived Nueral Progenitor Cells, Stem Cell Reports, 2018, vol. 10, pp. 1696-1704.
Araoka, et al., Efficient and rapid induction of human iPSCs/ESCs into nephrogenic intermediate mesoderm using small molecule-based differentiation methods, PLOS One, 2014, 9(1), 14 pages.
Badger et al., Parkinson's disease in a dish Using stem cells as a molecular tool. Neuropharmacology, 2014, vol. 76, pp. 88-96.
Bai et al., BMP-2, VEGF and bFGF Synergistically Promote the Osteogenic Differentiation of Rat Bone Marrow-Derived Mesenchymal Stem Cells, Biotechnol Lett, 2013, vol. 35, pp. 301-308.
Bar-Am et al., Regulation of protein kinase C by the anti-Parkinson drug, MAO-B inhibitor, rasagiline and its derivatives, in vivo, Journal of Neurochemistry, 2004, vol. 89, No. 5, pp. 1119-1125.
Bohrnsen et al. Supportive angiogenic and osteogenic differentiation of mesenchymal stromal cells and endothelial cells in monolayer and co-cultures. International Journal of Oral Science (2016) 8, 223-230 (Year: 2016).
Chen, et al., Chemically defined conditions for human iPSC derivation and culture, 2011, Nat. Methods, 8(5), 8 pages.
Cooper et al., Differentiation of human ES and Parkinson's disease iPS cells into ventral midbrain dopaminergic neurons requires a high activity form of SHH, FGF8a and specific regionalization by retinoic acid, Molecular and Cellular Neurosciences, 2010, vol. 45, No. 3, pp. 258-266.
Farrelly et al., Extracellular matrix regulates apoptosis in mammary epithelium through a control on insulin signaling, The Journal of Cell Biology, 1999, 144(6):1337-1347.
Gurusamy et al., Hepatocyte Growth Factor-Like Protein is a Positive Regulator of Early Mammary Gland Ductal Morphogenesis, Mechanisms of Development, 2014, vol. 133, pp. 11-22.
Hens et al., BMP4 and PTHrP interact to stimulate ductal outgrowth during embryonic mammary development and to inhibit hair follicle induction, Development, 2017, 134:1221-1230.
Ichida et al., Probing disorders of the nervous system using reprogramming approaches, The EMBO Journal / European Molecular Biology Organization, 2015, vol. 34, No. 11, pp. 1456-1477.
Kessier et al., The Notch and Wnt pathways Regulate Stemness and Differentiation in Human Fallopian Tube Organoids, Nature Communications, 2015, vol. 6, p. 8989.
Kim et al. A practical guide to microfluidic perfusion culture of adherent mammalian cells. Lab Chip, 2007, 7, 681-694 (Year: 2007).
Kim et al. Shear Stress Induced by an Interstitial Level of Slow Flow Increases the Osteogenic Differentiation of Mesenchymal Stem Cells through TAZ Activation. PLoS ONE 9(3): e92427. p. 1-9 (Year: 2014).
Kitamura et al., Possible Involvement of Both Mitochondria and Endoplasmic Reticulum-Dependent Caspase Pathways in Retenone-Induced Apoptosis in Human Neuroblastoma SH-SY5Y Cells, Neuroscience Letters, 2002, vol. 2002, pp. 25-28.
Kreke et al. Effect of Intermittent Shear Stress on Mechanotransductive Signaling and Osteoblastic Differentiation of Bone Marrow Stromal Cells. Tissue Engineering: Part A vol. 14, No. 4, 2008. p. 529-537 (Year: 2008).
Levanon, et al., Primary ex vivo cultures of human fallopian tube epithelium as a model for serous ovarian carcinogenesis, Oncogene, 2010, 29(8):1103-1113.
Maegawa et al. Enhancement of osteoblastic differentiation of mesenchymal stromal cells cultured by selective combination of bone morphogenetic protein-2 (BMP-2) and fibroblast growth factor-2 (FGF-2). J Tissue Eng Regen Med 2007; 1: 306-313 (Year: 2007) Abstract Only.
Nishimura et al. Effect of osteogenic differentiation medium on proliferation and differentiation of human mesenchymal stem cells in threedimensional culture with radial flow bioreactor. Regenerative Therapy 2 (2015) 24-31 (Year: 2015).
Rey, et al., Chapter 7, Sexual Differentiation, 2016 [online]. [Retrieved on Sep. 19, 2019]. Retrieved from the internet <URL:https://www.endotext.org/wp-content/uploads/pdfs/sexual-differentiation.pdf>, 89 pages.
Ryan et al., Isogenic Human iPSC Parkinson's Model Shows Nitrosative Stress-Induced Dysfunction in MEF2-PGCl [alpha] Trans, Cell, Elsevier,2013, vol. 155, No. 6, pp. 1351-1364.
Qu et al., Differentiation of human induced pluripotent stem cells to mammary-like organoids, Stem Cell Reports, 2017, 8(2):205-215.
Sanchez-Danes et al., Disease-specific phenotypes in dopamine neurons from human iPS-based models of genetic and sporadic Parkinson's disease, EMBO Molecular Medicine, 2015, vol. 4, No. 5, pp. 380-395.
Simeone et al., The Otx Family, Pattern Formation and Development Mechanisms, 2002, vol. 12, pp. 409-415.
Sun et al., Role of Bone Morphogenetic Protein-2 in Osteogenic Differentiation of MesenChymal Stem Cells, Molecular Medicine Reports, 2015, vol. 12, pp. 4230-4237.
Tian et al., Salvianolic Acid B, An Antioxidant from Saliva Miltiorrhiza, prevents 6-hydroxydopamine Induced Apoptosis in SH-SY5Y Cells, The International Science Journal of Biochemistry & Cell Biology, 2008, vol. 40, pp. 409-422.
Vogel et al., Co-culture of human induced pluripotent stem cells 9iPSCs) with human fallopian tube epithelium (FTE) induces Pax8 and CK7 expression: Initial steps in modeling fallopian tube epithelium to study serous carcinogenesis; Gynecologic Oncology, 2015 137(1):206.
Wu et al., Nuclear Accumulation of Histone Deacetylase 4 (HDAC4) Exerts Neurotoxicity in Models of Parkinson's Disease, Moi Neurobiol, 2017, vol. 54, pp. 6970-6983.
Zhang et al., Regulation and Patterning of Cell Differentiation and Pluripotency, Thesis, Columbia University, pp. 1-177, 2011.
Zhang et al., FGF Ligands of the Postnatal Mammary Stroma Regulate Distinct Aspects of Epithelial Morphogenesis, Stem Cells and Regeneration, 2014, vol. 141, pp. 3352-3362.
DMEM F-12 Formulation, pp. 1-5, 2022.

(56) References Cited

OTHER PUBLICATIONS

Mehta et al., The actions of retinoids on cellular growth correlate with their actions on gap junctional communication, JCB 108, 1053-1065, 1989.

Essential 8 medium C037161 Essential8System Brochure (thermofisher.com), downloaded on Aug. 24, 2022, pp. 1-2.

ISR and WO for PCT/US2021/030128 dated Aug. 25, 2021, 10 pages.

Arendt et al., Form and Function: how Estrogen and Progesterone Regulate the Mammary Epithelial Hierarchy, J. Mammary Gland Biol Neoplasia, 2015, 20:9-25.

Qiao et al, AP2y regulates neural and epiderman development downstream of the BMP pathway at early stages of ectodermal patterning, Cell Research, 2012, 22:1546-1561.

Lin et al., Embryoid body formation from human pluripotent stem cells in chemically defined E8 media, StemBook, ed, Jun. 1, 2014.

JP Reasons for Rejection—2020-560893 dated Feb. 6, 2023, 9 pages.

Matsumoto et al., Functional neurons generated from T Cell-derived induced pluripotent stem cells for neurological disease modeling, 2016, 6:422-435.

Moors et al., Therapeutic potential of autophagy-enhancing agents in Parkinson's disease, Molecular Neurodegeneration, 2017, 12:11, p. 1-18.

Okita et al., An efficient nonviral method to generate integration-free human-induced pluripotent stem cells from cord blood and peripheral blood cells, Stem Cells 2013, 31:458-466.

Kondo et al., iPSC-Based compound screening and in vitro trials identify a synergistic anti-amyloid B combination for Alzheimer's Disease, Cell Reports 2017, 21:2304-2312.

Hojo et al., Development of high-throughput screening system for osteogenic drugs using a cell-based sensor, Biochemical and Biophysical Research Communiatins 376(2):375-379, 2008.

* cited by examiner

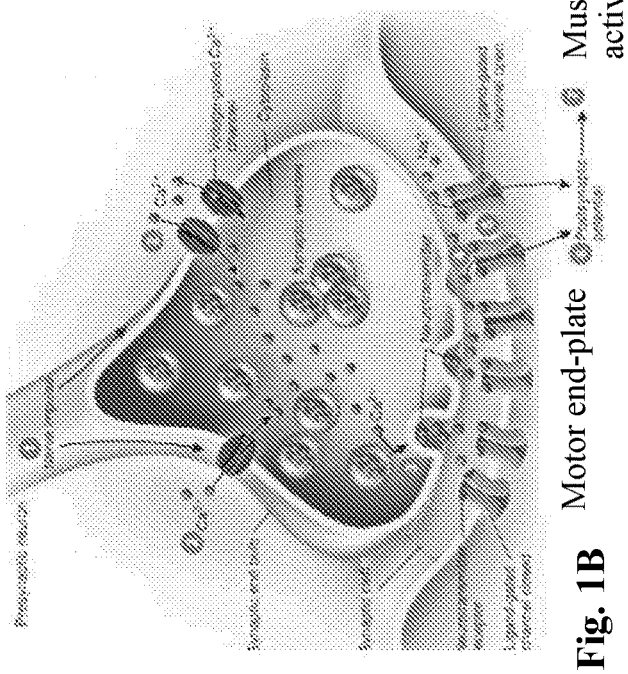
Fig. 1B Motor end-plate
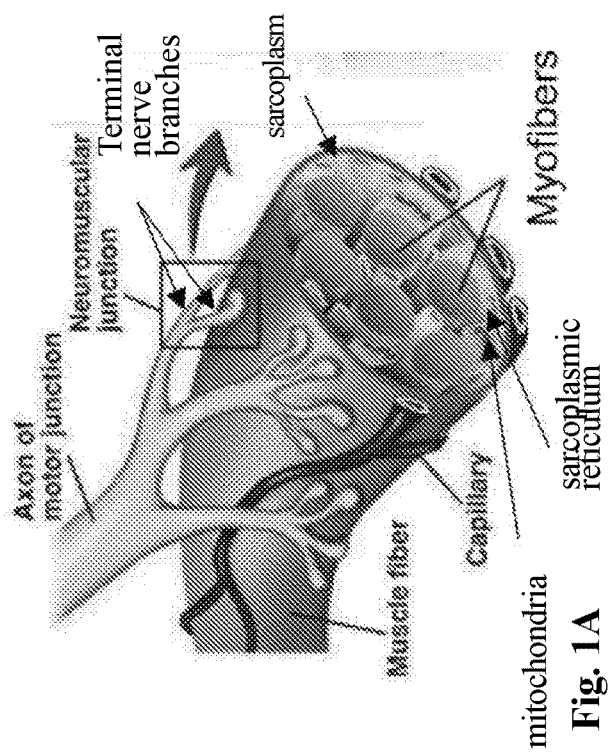
Fig. 1A
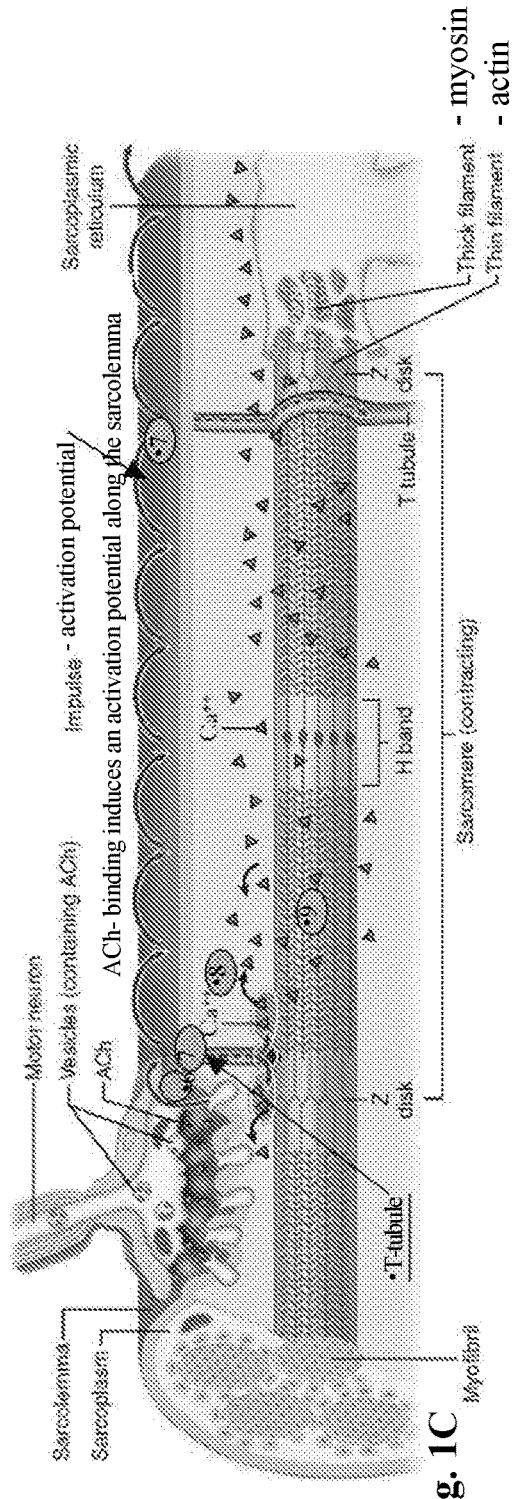
Fig. 1C

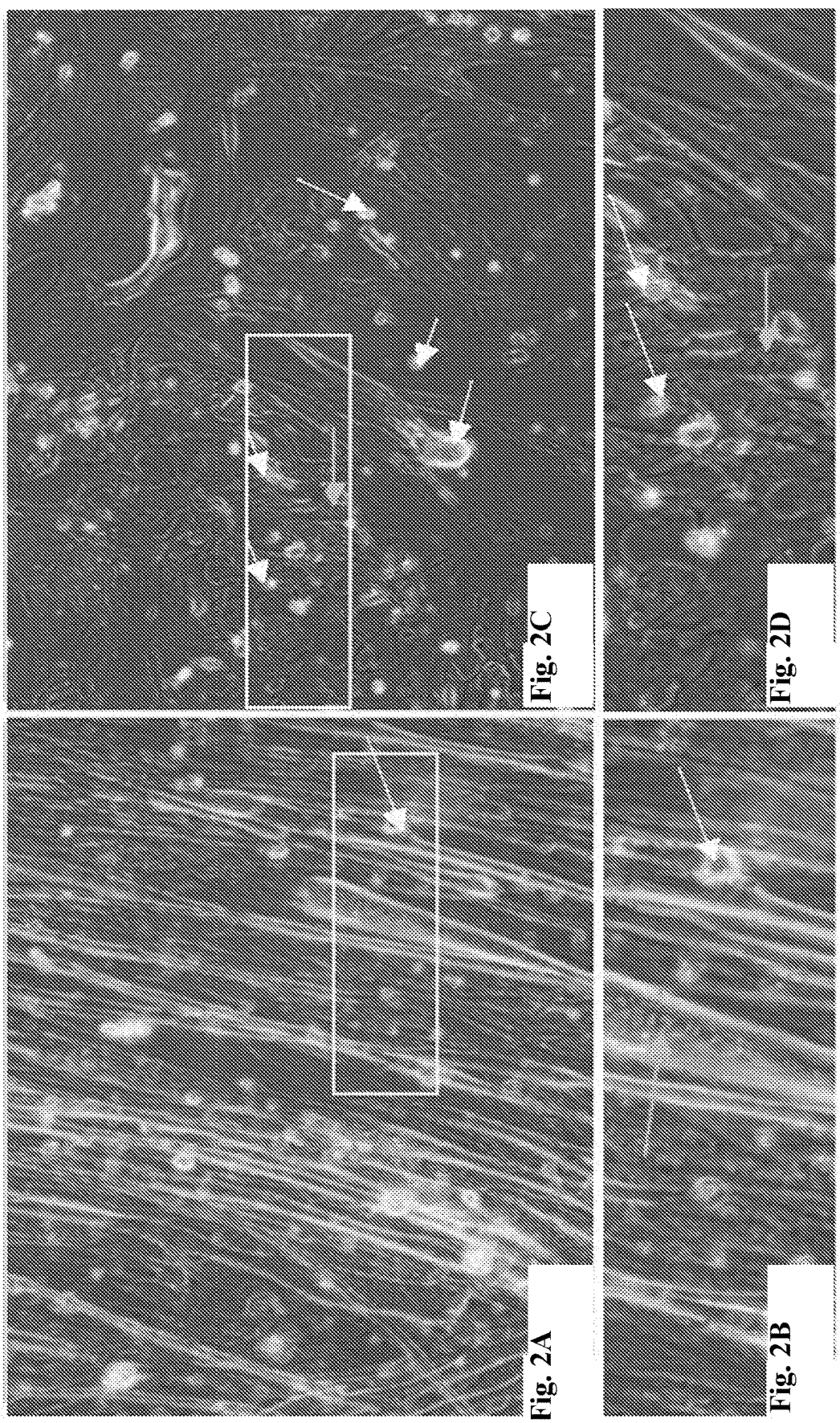

Regular ECM | Sulfo Sanpah

Human fetal Skeletal Muscle Cells (hSkMCs)
ECM (Laminine)
Cross linking of ECM with Sulfo Sanpah

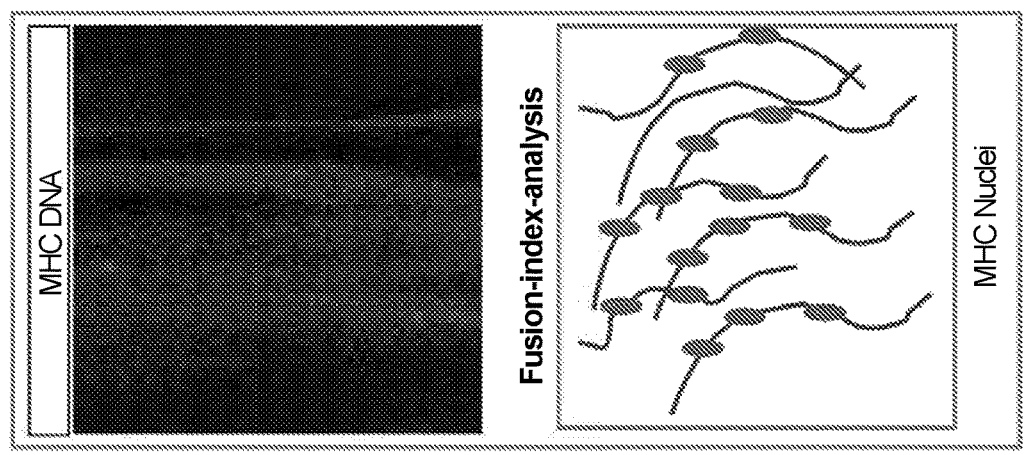
Fig. 5C
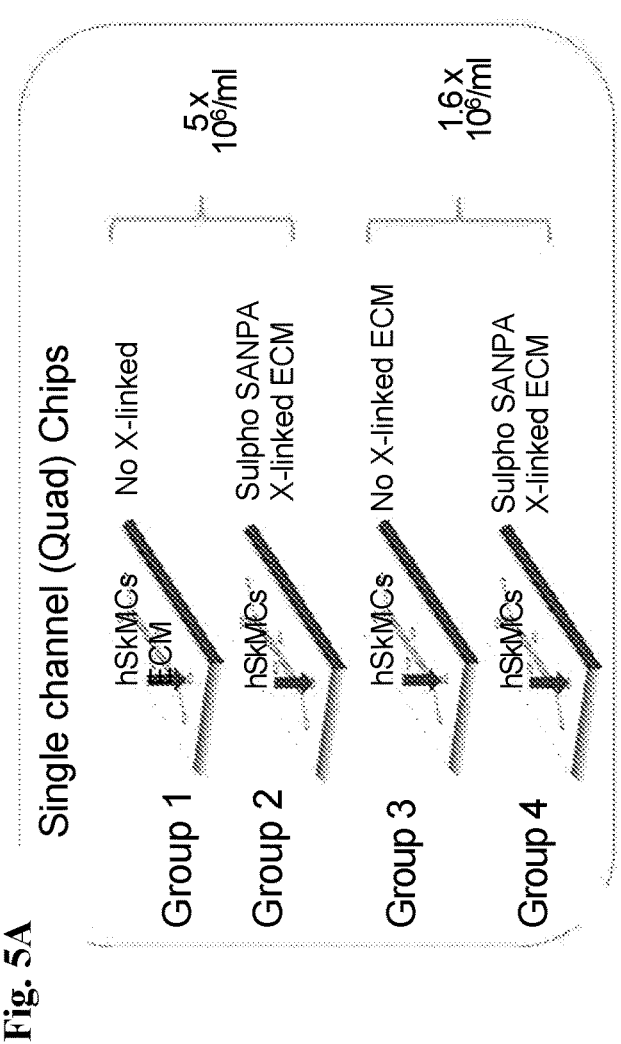
Fig. 5A
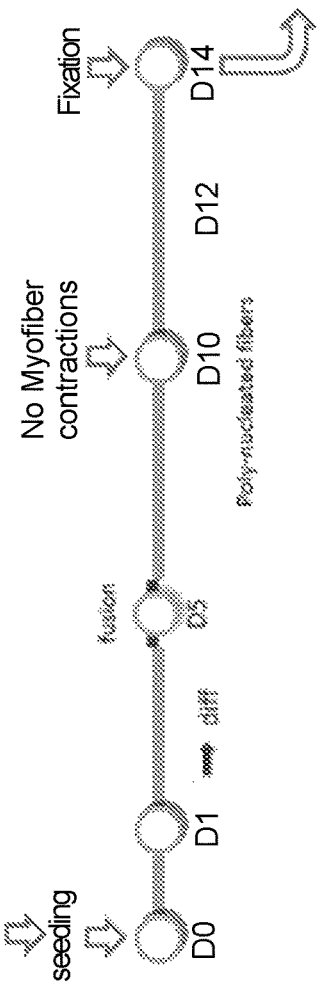
Fig. 5D
Fig. 5B

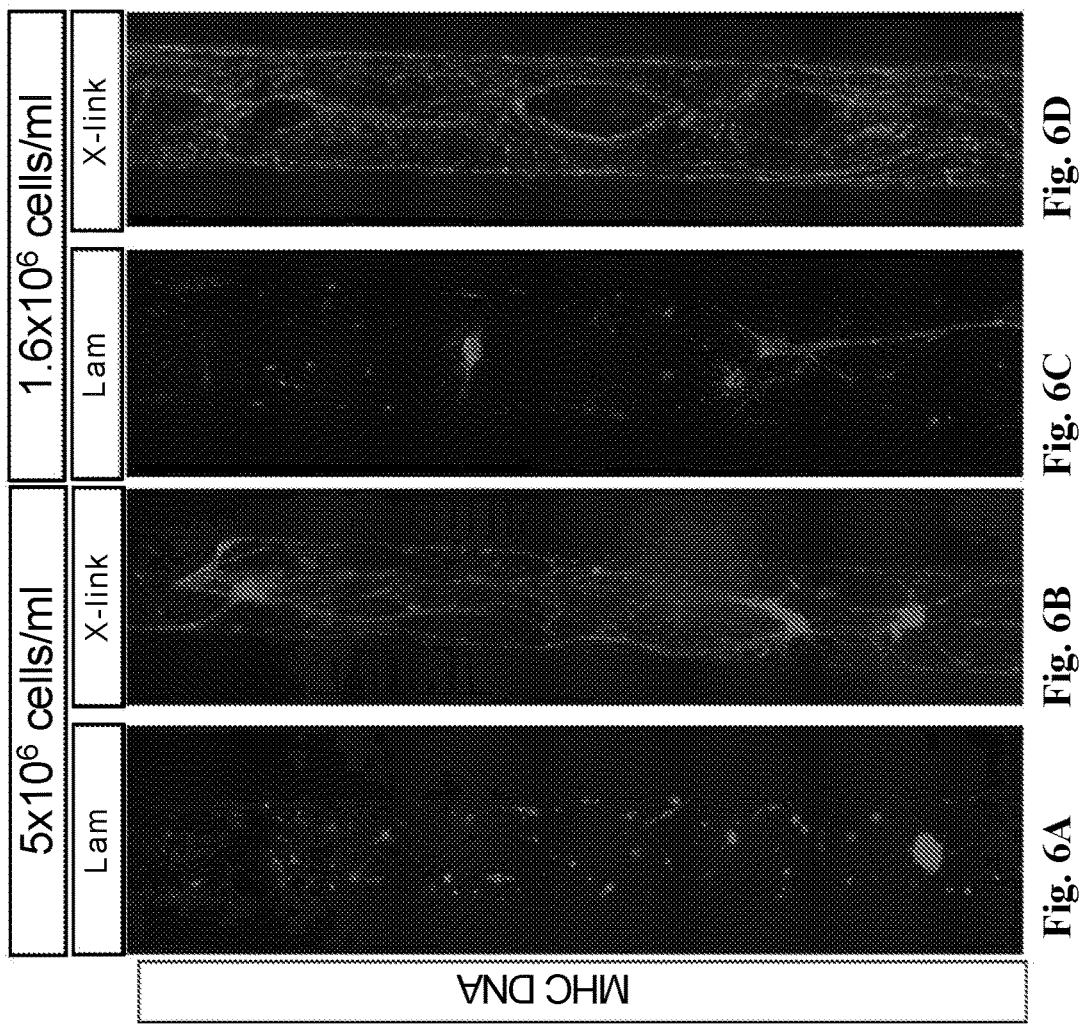
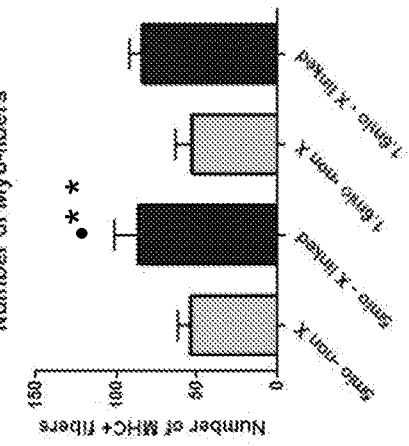

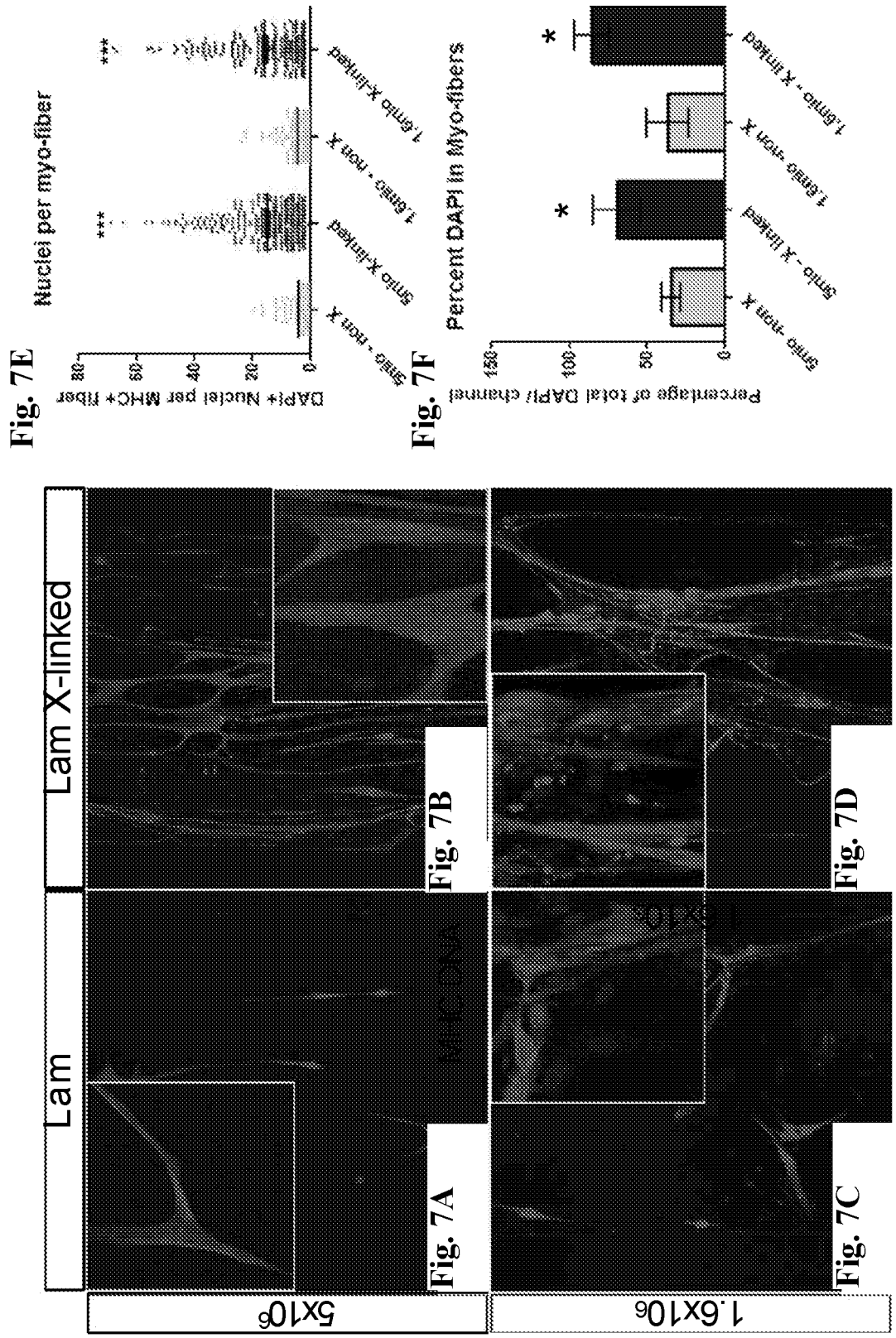

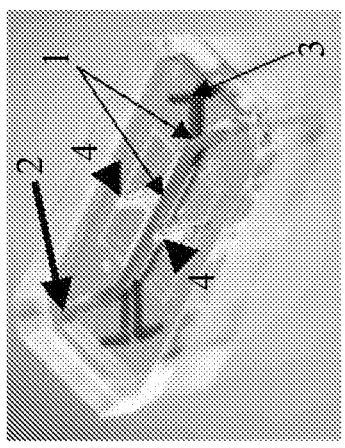
Fig. 8A
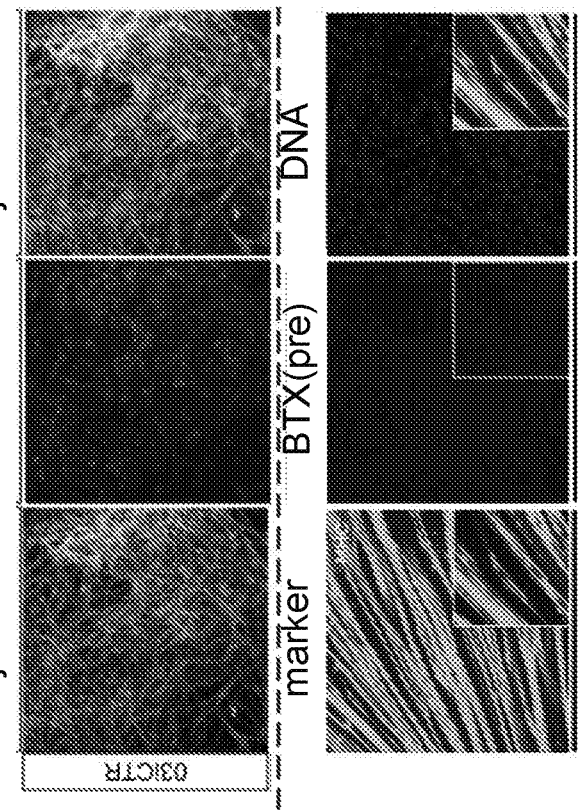
Fig. 8B
Fig. 8C
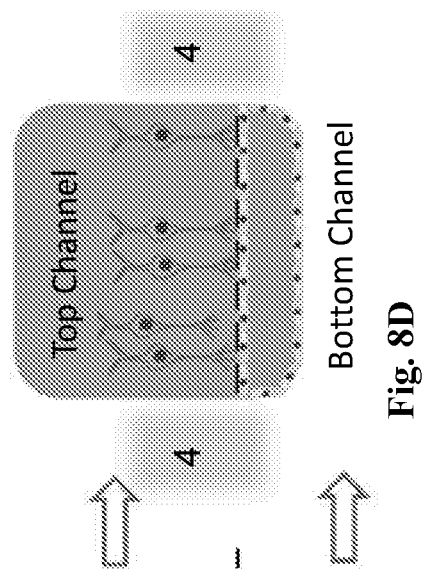
Fig. 8D

Fig. 9A
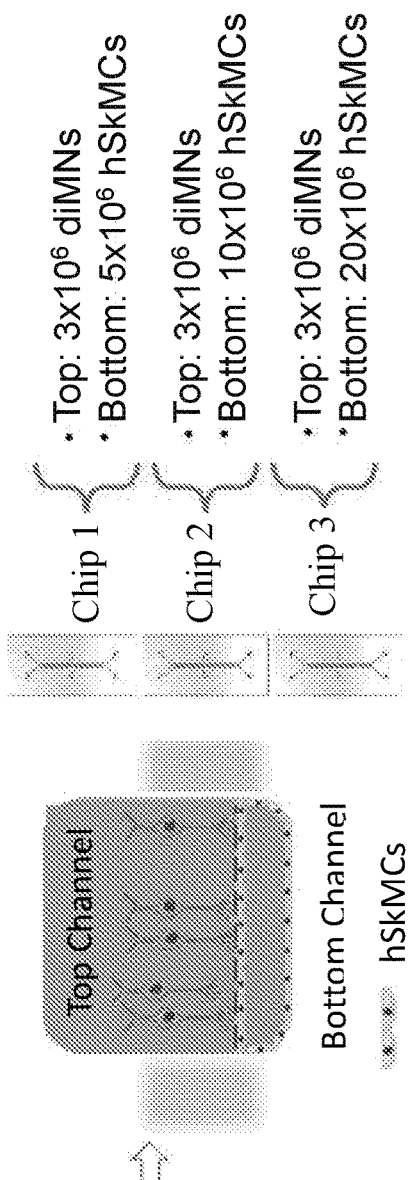
Fig. 9B
Fig. 9C
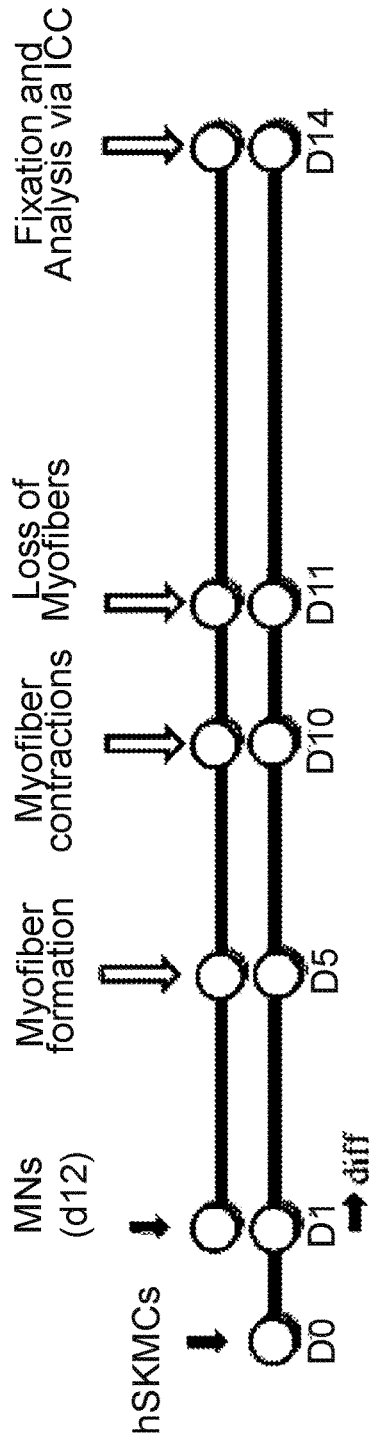

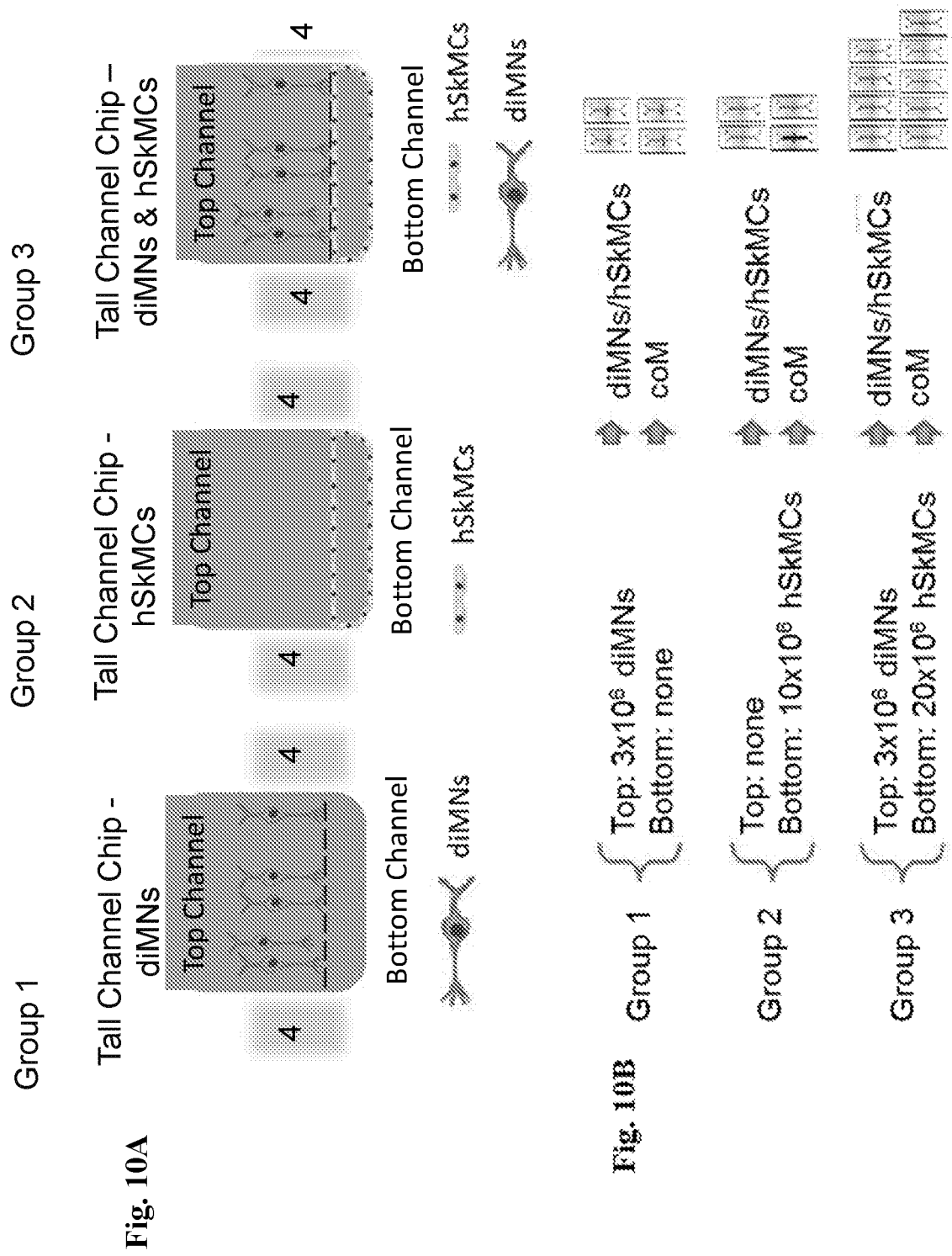

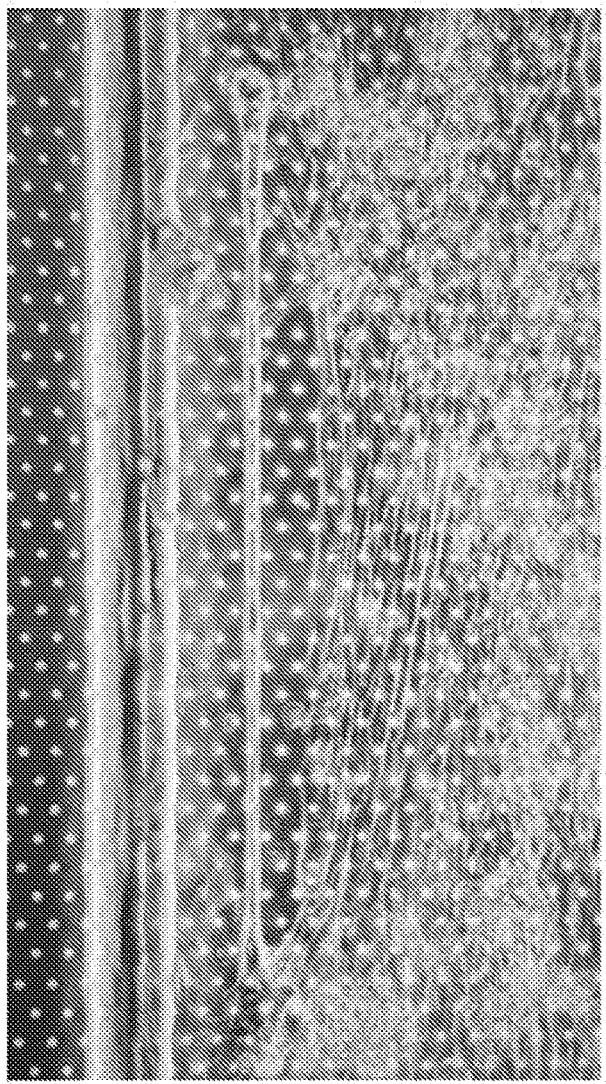
Fig. 12A
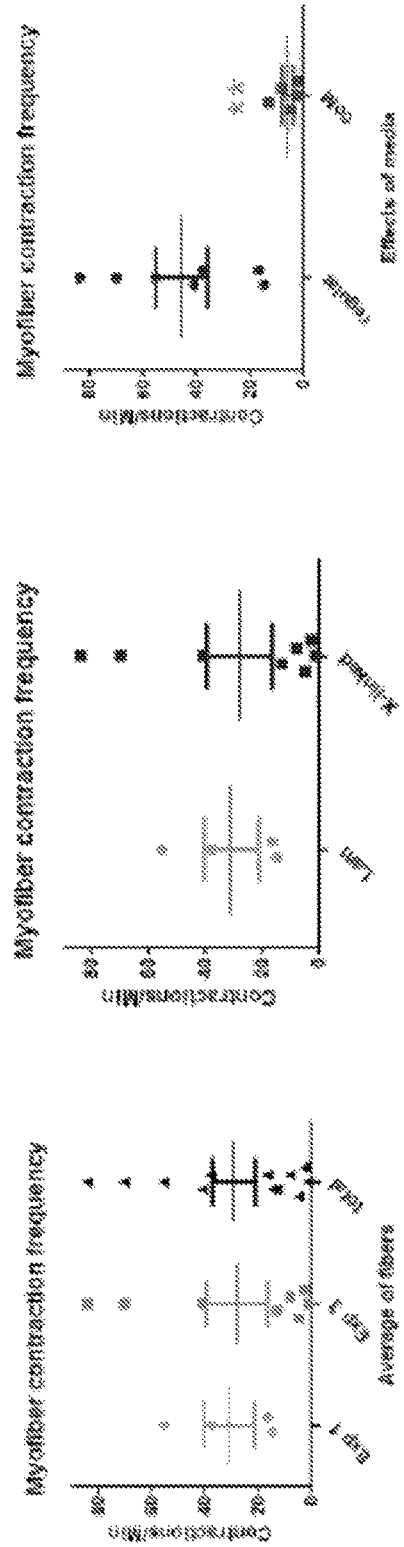
Fig. 12B
Fig. 12C
Fig. 12D

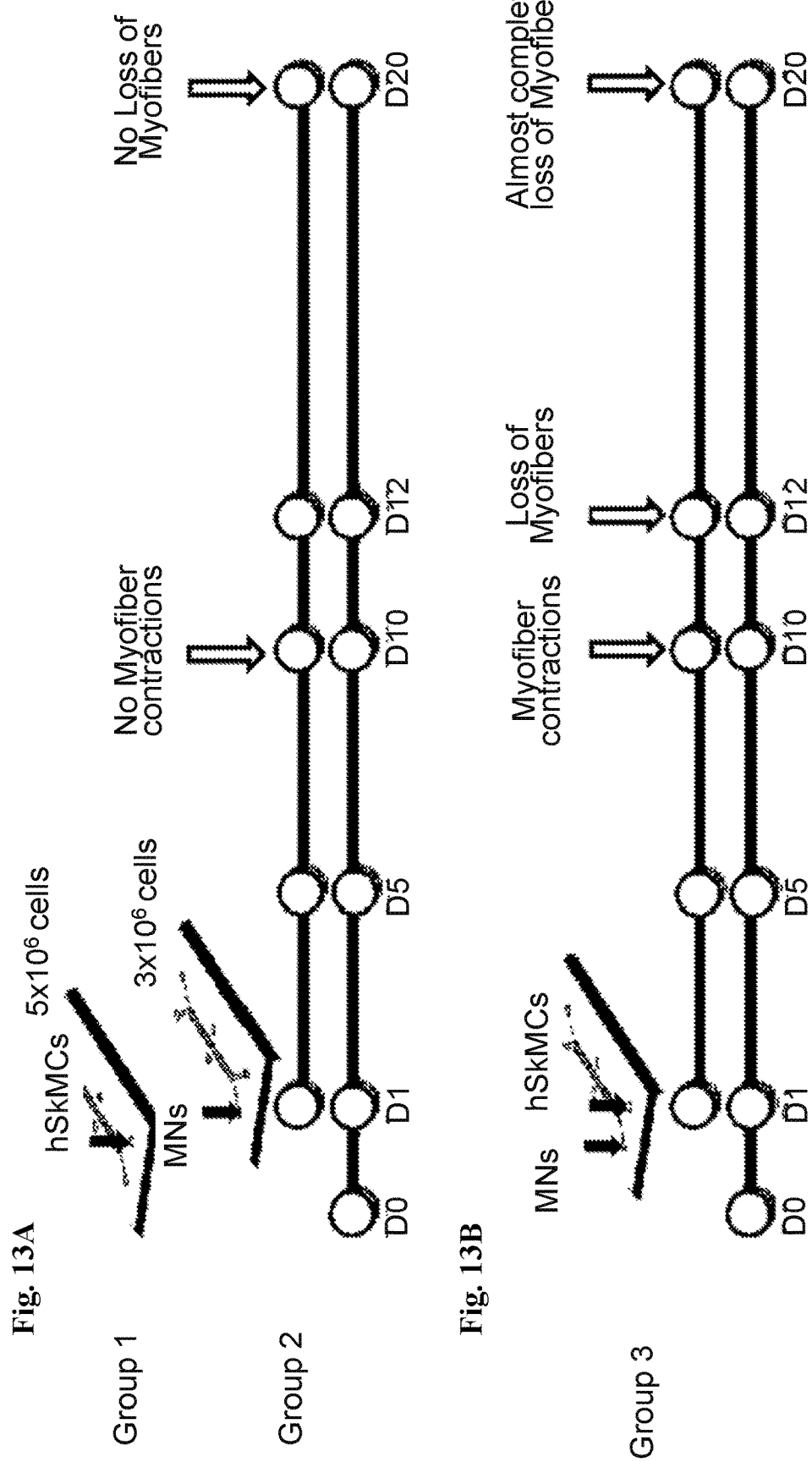

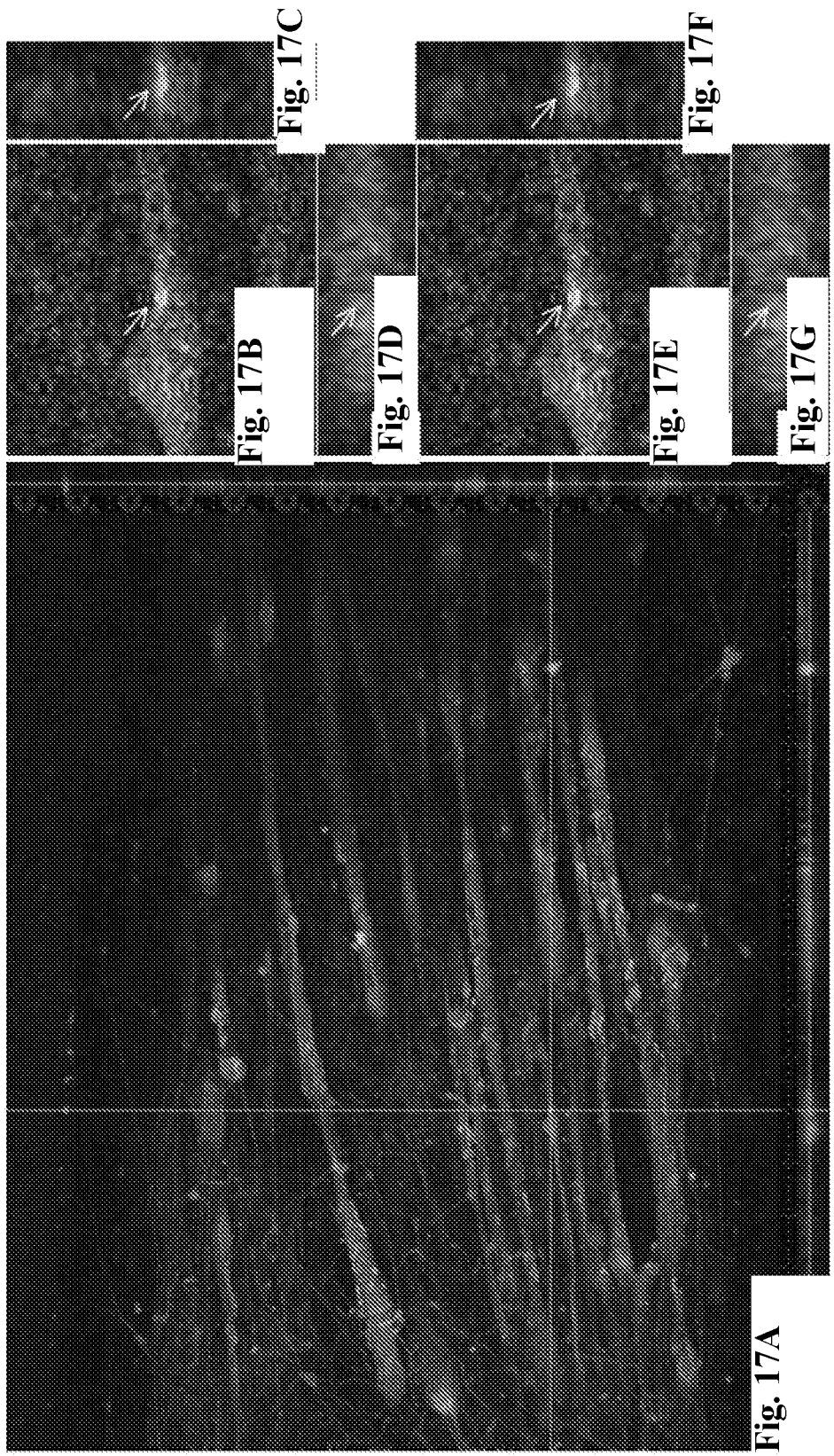

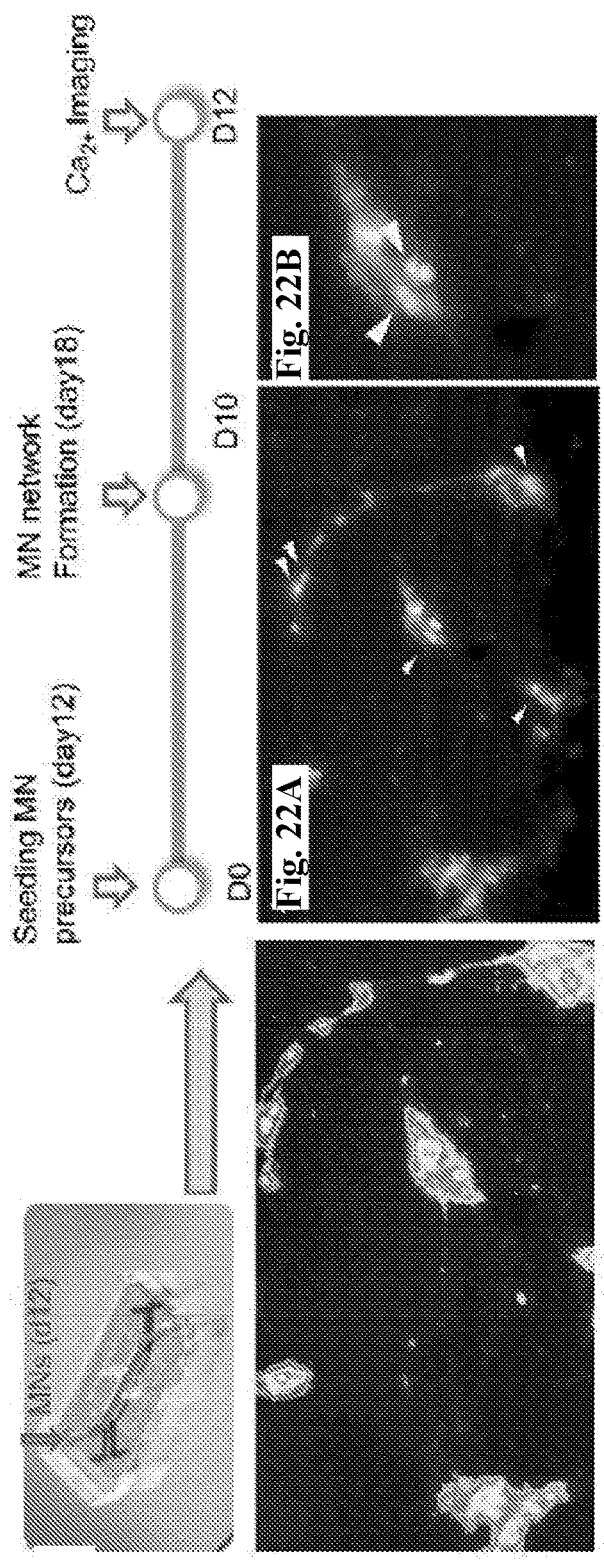
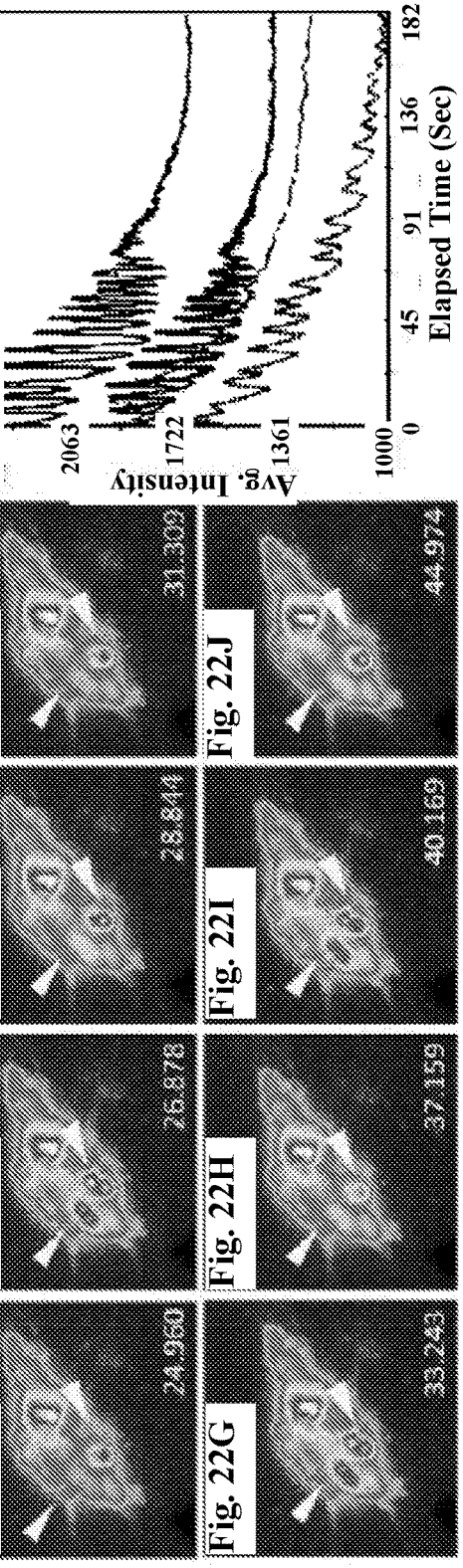
Fig. 22AA
Fig. 22BB
Fig. 22CC

Figure 23.
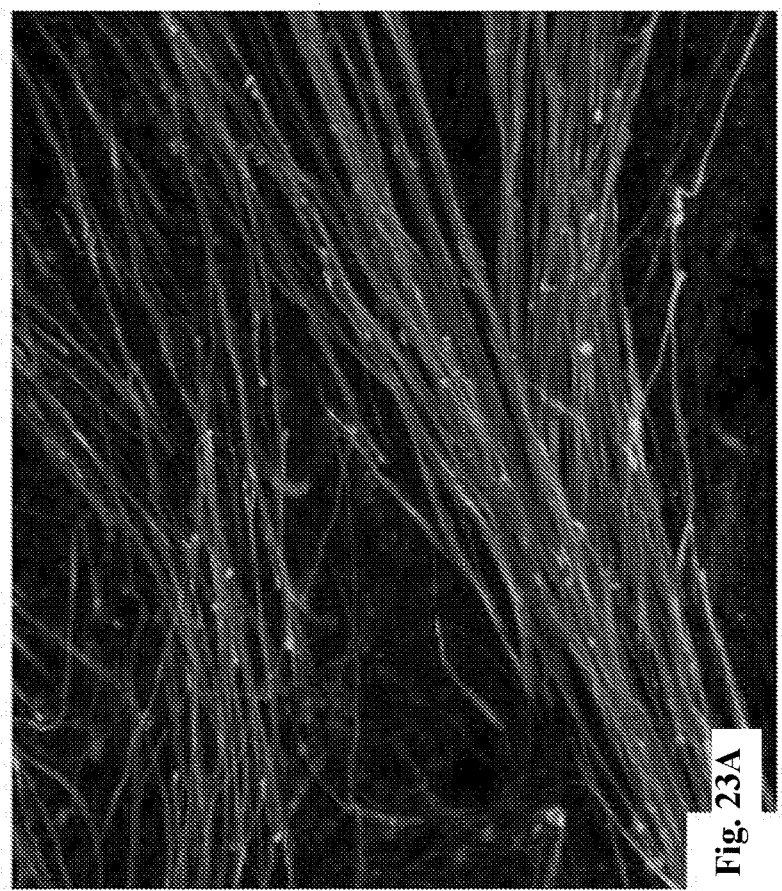
Fig. 23A
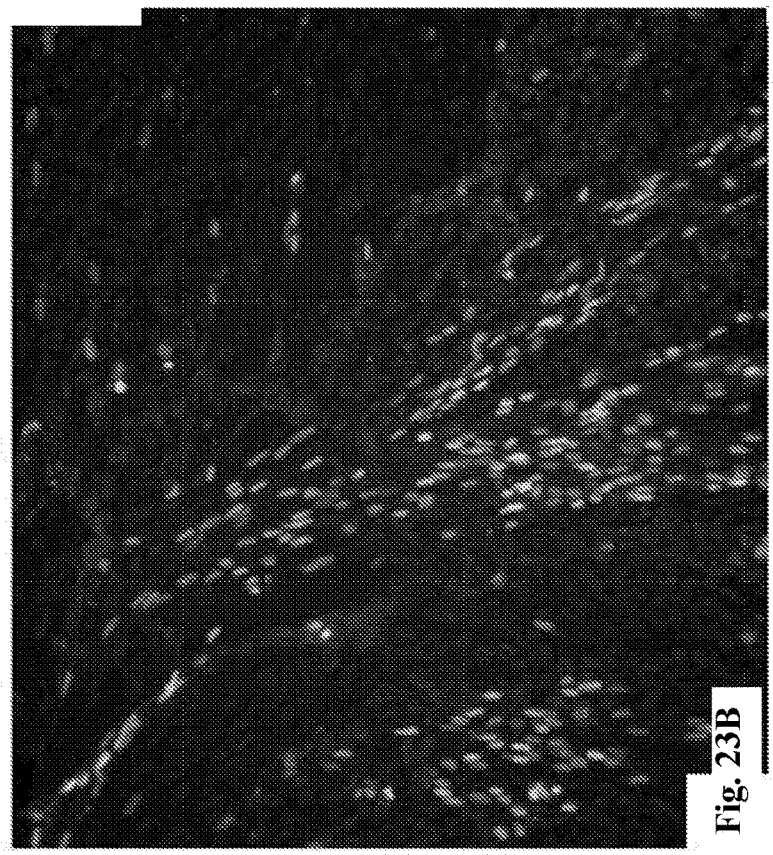
Fig. 23B

US 11,767,513 B2

NEUROMUSCULAR JUNCTION

CROSS-REFERENCE TO RELATED APPLICATIONS

This application is the national phase of International Application No. PCT/US2018/022511, filed Mar. 14, 2018, which designated the U.S. and that International Application was published under PCT Article 21(2) in English. This application claims priority under 35 U.S.C. § 119(e) to U.S. Provisional Application No. 62/471,273, filed Mar. 14, 2017, the contents of which are herein incorporated by reference in their entirety.

FIELD OF THE INVENTION

The invention relates to culturing motor neuron cells together with skeletal muscle cells in a microfluidic device under conditions whereby the interaction of these cells mimic the structure and function of the neuromuscular junction (NMJ) providing a NMJ-on-chip. Good viability, formation of myo-fibers and function of skeletal muscle cells on fluidic chips allow for measurements of muscle cell contractions. Embodiments of motor neurons co-cultures with contractile myo-fibers are contemplated for use with modeling diseases affecting NMJ's, e.g. Amyotrophic lateral sclerosis (ALS).

BACKGROUND OF THE INVENTION

The neuromuscular junction (NMJ) is of major clinical relevance. First, dysfunction of the NMJ leads to degeneration of motor neuron-skeletal muscle unit. Secondly, drugs that are supposed to treat neurological disorders often fail to restore the end plate potential to activate the muscle fibers.

Amyotrophic lateral sclerosis (ALS) is most common neurodegenerative disease affecting 2.5 in 100,000 per year but the cause of the disease is unknown.

Because of its importance in disease and medical treatment, it would be highly advantageous to have a predictive model of the NMJ that recapitulates aspects of the motoneuronal-muscle cell microenvironment in a controlled way.

SUMMARY OF THE INVENTION

Described herein is a method of generating myotubes, including providing a quantity of induced pluripotent stem cells (iPSCs), culturing the iPSCs in the presence of a first induction media to generate mesoderm cells, further culturing mesoderm cells in the presence of a second induction media to generate myoblasts, and maturing the myoblasts into myotybes by culturing in the presence of a maturation media. In other embodiments, the first induction media includes CHIR99021 and/or LDN193189. In other embodiments, the first induction media includes bFGF (basic fibroblast growth factor). In other embodiments, culturing the iPSCs in the presence of a first induction media includes about 6, 7, 8, or 9 days. In other embodiments, the second induction media includes CHIR99021 and/or LDN193189. In other embodiments, the second induction media includes bFGF, HGF (hepatocyte growth factor) and/or IGF (insulin-like growth factor). In other embodiments, further culturing mesoderm cells in the presence of a second induction media includes about 2, 3, 4, or 5 days. In other embodiments, the maturation media includes serum replacement. In other embodiments, the maturation media includes HGF and/or IGF. In other embodiments, maturing the myoblasts by culturing in the presence of a maturation media includes about 25, 26, 27, 28, 29, 30, 31, 32, or 33 days. In other embodiments, the myotubes form contractile tissue. In other embodiments, the myotubes form polynucleated myo-fibers. In other embodiments, culturing the iPSCS, further culturing mesoderm cells, and/or maturing the myoblasts is on a coated substrate. In other embodiments, the coated substrate includes one or more extracellular matrix proteins. In other embodiments, the one or more extracellular matrix proteins includes Matrigel. In other embodiments, the one or more extracellular matrix proteins includes laminin. In other embodiments, the iPSCS are derived from a human. In other embodiments, the human is diagnosed with a neuron disease and/or condition. In other embodiments, the human is diagnosed with a muscle disease and/or condition.

Also described herein is a neuromuscular junction including one or more neurons, and one or more muscle cells, wherein the one or more neurons and one or more muscle are fixed on a substrate, and the one or more neurons are capable of generating activation potential and/or inducing contraction in the one or more muscle cells. In other embodiments, the substrate includes a surface of a microfluidic device. In other embodiments, the one or more neurons are differentiated from induced pluripotent stem cells (iPSCs). In other embodiments, the human is diagnosed with a neuron disease and/or condition. In other embodiments, the one or more muscle cells are differentiated from induced pluripotent stem cells (iPSCs). In other embodiments, the human is diagnosed with a muscle disease and/or condition.

Described herein is culturing motor neuron cells together with skeletal muscle cells in a fluidic device under conditions whereby the interaction of these cells mimic the structure and function of the neuromuscular junction (NMJ). Good viability, formation of myo-fibers and function of skeletal muscle cells on fluidic chips allow for measurements of muscle cell contractions. Embodiments of motor neurons co-cultures with contractile myo-fibers are contemplated for use with modeling diseases affecting NMJ's, e.g. Amyotrophic lateral sclerosis (ALS).

In one embodiment, the present invention contemplates a method of culturing cells, including: a) providing a microfluidic device including a membrane, said membrane including a top surface and a bottom surface; b) seeding induced motor neuron cells on said top surface and skeletal muscle cells on said bottom surface so as to create seeded cells; c) exposing said seeded cells to a flow of culture media for a period of time; and d) culturing said seeded cells under conditions such that a neuromuscular junction forms within said microfluidic device. The formation of the neuromuscular junction can be detected in a number of ways. It is not intended that the present invention be limited to how the neuromuscular junction is detected or measured. In one embodiment, the NMJ detected by measurement and/or detection of the binding of α-bungarotoxin (BTX), Tubulin beta-3 chain (Tubb3) and/or muscle myosin heavy chain (MHC), and in a preferred embodiment, where co-localization of these markers is detected. In a preferred embodiment, a color label (e.g. fluorescent label) is used for each marker with combined multi-channel reading as a measurement of co-localization. However, the present invention contemplates additional approaches including but not limited to functional measurement/detection of the NMJ. Such functional embodiments include measuring and/or detecting the formation of the NMJ as demonstrated by measuring and/or detecting nerve action potential, neurotransmitter release, muscle cell membrane activation potential and/or myofiber contraction. In one embodiment, these events occur in sequence and are synchronized (e.g. with synchronization comparable to an in vivo neuromuscular junction response as understood to one of ordinary skill). In one embodiment, said skeletal muscle cells are induced to differentiate. In one embodiment, said skeletal muscle cells form contractile tissue. In one embodiment, said skeletal muscle cells form polynucleated myo-fibers. In one embodiment, said seeded cells are cultured for more than ten days. In one embodiment, said induced motor neuron cells are derived from induced pluripotent stem cells from a human. In one embodiment, said human is diagnosed with a CNS disorder. In one embodiment, the present invention contemplates that the method further includes the step of e) assessing the health and/or integrity of the neuromuscular junction. This can be done a number of ways. For example, this can be done by measurement and/or detection of the binding of α-bungarotoxin (BTX), Tubulin beta-3 chain (Tubb3) and/or muscle myosin heavy chain (MHC), and in a preferred embodiment, where co-localization of these markers is detected. This can also be done by measuring and/or detecting nerve action potential, neurotransmitter release, muscle cell membrane activation potential and/or myofiber contraction. The present invention also contemplates and embodiment where the method further includes the step of e) electrically stimulating said motor neurons and/or said skeletal muscle cells.

It is not intended that the present invention be limited to situations where both neurons and skeletal muscle cells are seeded together. In one embodiment, the present invention contemplates a method of culturing cells, including: a) providing a microfluidic device including a channel; b) seeding skeletal muscle cells into said channel; c) inducing said skeletal muscle cells to differentiate; and d) detecting myo-fiber formation. Motor neurons can be (optionally) added before or after the muscle cells (or not at all). In one embodiment, said detecting of myo-fiber formation includes detecting myo-fiber contractions. In one embodiment, said seeded cells are exposed to a flow of culture media for a period of time. In a preferred embodiment, the cells are seeded onto covalently attached ECM protein(s).

The present invention also contemplates seeding on both patterned surfaces and/or gels. In one embodiment, the present invention contemplates a method of culturing cells, including: a) providing a microfluidic device including a patterned surface and a gel, b) seeding induced motor neuron cells on said patterned surface and skeletal muscle cells on said gel. In one embodiment, the present invention contemplates that the method further includes c) detecting myo-fiber formation by said skeletal muscle cells. In one embodiment, said detecting of myo-fiber formation includes detecting myo-fiber contractions. In one embodiment, said skeletal muscle cells and/or said motor neurons are exposed to a flow of culture media for a period of time.

The present invention also contemplates microfluidic devices with cells. In one embodiment, the present invention contemplates a microfluidic device including a) a membrane, said membrane including a top surface and a bottom surface; and b) induced motor neuron cells on said top surface and skeletal muscle cells on said bottom surface. In one embodiment, said induced motor neuron cells are derived from induced pluripotent stem cells from a human. In one embodiment, said human is diagnosed with a CNS disorder. In one embodiment, said CNS disorder is ALS. In one embodiment, said membrane includes covalently attached ECM protein(s).

The present invention also contemplates systems including microfluidic devices with cells under flow conditions. In one embodiment, the present invention contemplates a system including a microfluidic device, said microfluidic device including a) a membrane, said membrane including a top surface and a bottom surface; and b) induced motor neuron cells on said top surface and skeletal muscle cells on said bottom surface, wherein either one of said cell types or both are exposed to culture media at a flow rate. In one embodiment, said induced motor neuron cells are derived from induced pluripotent stem cells from a human. In one embodiment, said human is diagnosed with a CNS disorder. In one embodiment, said CNS disorder is ALS. In one embodiment, said membrane includes covalently attached ECM protein(s). In one embodiment, the membrane is in a channel, said channel is in fluidic communication with a reservoir including culture media.

Definitions

Some abbreviations are used herein.

For example, "MN" refers to motor neurons. The letter "i" indicates "induced." Thus, "iMN" indicates induced motor neurons, i.e. motor neurons that were induced or generated from other cells, e.g. stem cells. "diMN" indicates direct induced motor neurons. "iMNP" indicates induced motor neuron progenitor cells, which are not fully differentiated into mature neurons.

The term "microfluidic" as used herein relates to components where moving fluid is constrained in or directed through one or more channels wherein one or more dimensions are 10 mm or smaller (microscale). Microfluidic channels may be larger than microscale in one or more directions, though the channel(s) may be on the microscale in at least one direction. In some instances the geometry of a microfluidic channel may be configured to control the fluid flow rate through the channel. Microfluidic channels can be formed of various geometries to facilitate a wide range of flow rates through the channels. However, it is important to note that while the present disclosure makes frequent reference to "microfluidic" devices, much of what is taught applies similarly or equally to larger fluidic devices. Larger devices may be especially relevant if the "NMJ-on-chip" is intended for therapeutic application. Examples of applications that may make advantage of larger fluidic devices include the use of the device for the generation of highly differentiated cells (e.g. the device can used to drive cell differentiation and/or maturation, whereupon the cells are extracted for downstream use, which may include implantation, use in an extracorporeal device, or research use), or use of the device for implantation or extracorporeal use, for example, as an artificial NMJ. Unlike conventional static cultures, the present invention contemplates microfluidic devices where the cells are exposed to a constant flow of media providing nutrients and removing waste.

As used herein, the phrases "connected to," "coupled to," and "in communication with" refer to any form of interaction between two or more entities, including mechanical, electrical, magnetic, electromagnetic, fluidic, and thermal interaction. For example, in one embodiment, first and second channels in a microfluidic device are in fluidic communication with a fluid reservoir. Two components may be coupled to each other even though they are not in direct contact with each other. For example, two components may be coupled to each other through an intermediate component (e.g. tubing or other conduit).

BRIEF DESCRIPTION OF THE DRAWINGS

FIG. 1: shows schematics of neuromuscular junctions (NMJs) as interfaces between spinal motor neurons and skeletal muscle cells.

FIG. 1A: shows a schematic illustration of the exterior of neuromuscular junctions where the yellow axon of a motor nerve at the motor junction has non-myelinated terminal nerve branches forming neuromuscular junctions (one example of an NMJ is outlined by a square). The neuronal terminal nerve branches have synaptic end bulbs or buttons (see FIG. 1B) located opposite of a muscular fiber end plate (see FIG. 1B). FIG. 1A also shows a schematic of an interior view of a muscle fiber composed of numerous myo-fibers interspersed with mitochondria (blue), sarcoplasmic reticulum (yellow tubes) within the sarcoplasm of a muscle fiber cell (myocyte).

FIG. 1B: shows a cut-out schematic illustration of the interface between spinal motor neurons and skeletal muscle cells, e.g., a NMJ, for demonstrating the steps of normal motor neuronal activation of muscle fibers. Step 1) An action potential of a myelinated axon reaches the non-myelinated axon terminal branch. Step 2) Voltage-dependent calcium gates open allow Ca++ to enter the end bulb which in Step 3) induces the movement of neurotransmitter containing vesicles to merge with the cell membrane at the end of the synaptic bulb opposite muscle cell acetylcholine (ACh) receptors located in the motor end plates. Neurotransmitter vesicles containing acetylcholine (ACh) are emptied (by exocytosis) into the synaptic cleft. Step 4) Freed ACh from the vesicles then diffuses across the cleft to bind to postsynaptic receptors on the sarcolemma of the muscle fiber in the motor end plate area. Step 5) This ACh binding causes ion channel pumps to open which allows sodium ions to flow across the membrane into the muscle cell while fewer K+ ions are transported out of the cell i.e. (3) Na+ ions enter the cell cytoplasm while (2) K+ ions are transported out, thus triggering a post synaptic action potential (end plate potential) in the NMJ, i.e. the end plate of the muscle sarcolemma. Step 6) the postsynaptic action potential (AP) generated at the end plate, Step 7) AP wave, i.e., sarcolemma membrane depolarization, travels across the muscle cell membrane.

FIG. 1C: shows a schematic illustration of a muscle cell (myocyte) depicting how the postsynaptic action potential (AP), triggered by the NMJ, in the sarcolemma of the motor end plate, in Step 6) travels to nearby areas of the T-tubules (i.e. a wave of ion pump activation that travels along the membrane whereby (3) Na+ ions enter the cell cytoplasm while (2) K+ ions are transported out of the cell cytoplasm. Further in Step 7) When the AP reaches areas of the T-tubule portion of the sarcolemma, destabilizing this area of the membrane, the AP in the sarcolemma of the T-tubule area causes the T-tubule to induce the release of Ca++ from the sarcoplasmic reticulum. Step 8) The destabilized sarcolemma then triggers a wave of Ca++ release across the sarcoplasmic reticulum membrane inside of the myocyte. Step 9) The rise in intracellular Ca++ activates contraction of myofibrils, i.e. myosin-actin interactions.

FIG. 2: shows 2-Dimensional (2D) motor neurons (MN) and muscle cell co-cultures grown in static plates, on day 37 of culture.

FIG. 2A: shows a micrograph of healthy human muscle skeletal cells (hSkMCs);

FIG. 2B: shows a higher magnification of cells in FIG. 2A, where the green arrow points to one exemplary multinucleated myotube;

FIG. 2C: shows a micrograph of a co-culture of direct induced motor neurons (diMNs) on top of hSkMCs where white arrows point to rounded cell bodies, a green arrow points to an exemplary myotube and a red arrow points to an exemplary neuron on top of said myotube; and FIG. 2D: shows a higher magnification of cells in FIG. 2C where the red arrow points to neuronal branches on top of a myotube identified by a green arrow. White boxes outline the areas shown in higher magnification.

FIG. 3: shows exemplary phase contrast images for embodiments of neuronal growth.

FIG. 4: Shows one embodiment of a human skeletal muscle cell culture hSkMC-In-Chip: Extracellular Matrix for fluidic hSkMCs-In-Chip. In one embodiment, the chip is a Quad chip.

FIG. 5: shows one embodiment of a human muscle cell culture in-chip: Set Up and Time Course for producing multinucleated myofibers that are not contracting.

FIG. 5A: Single channels of Quad Chips were seeded with human skeletal muscle cells (hSKMCs). Group 1 and Group 2: $5 \times 10^6$/ml cells; Group 3 and Group 4: $1.6 \times 10^6$/ml cells. Groups 1 and 3 do not have cross (X)-linked ECM while Groups 2 and 4 have exemplary Sulpho SANPA X-linked ECM.

FIG. 5B: shows a schematic experimental timeline: Seeding cells on Day (D) 0. D1: Inducing differentiation. D5 observing fusion of myoblast cells. D10: Screening for myo-fiber contraction in cultures that were not stained for analysis; observing polynucleated fibers but no myofiber contractions. D14 Fixing cells and fusion-index-analysis.

FIG. 5C: Day 14: Fixation and fusion-index-analysis based upon staining for myosin heavy chain (MHC) (red) and nuclei (DNA) (shown in blue).

FIG. 5D: Shows a schematic illustration of multinucleated myofibers in WIC (red) and nuclei (DNA) (blue).

FIG. 6: shows Human Skeletal Myoblast-Derived Poly-Nucleated Fibers growing in microfluidic chips where Sulfo-SANPAH cross-linked ECM enables formation of almost 2-fold more MHC positive multinucleated fibers.

FIG. 6A, FIG. 6B, FIG. 6C, FIG. 6D: show fluorescent micrographs of immunostained myosin heavy chain (MHC) (red) myo-fibers and DAPI stained nuclei (DNA) (shown in blue) comparing cultures started at the 2 different densities (FIGS. 6A-B: $5 \times 10^6$/ml cells and FIGS. 6C-6D: $1.6 \times 10^6$/ml cells) with and without cross-lined (X-link) ECM-Laminin (Lam).

FIGS. 6E-6F: show phase contrast micrographs of Day 14 cells grown on Laminin (Lam) and cross-linked (X-Link) ECM-Laminin (Lam), respectively. More WIC positive multinucleated fibers are observed with X-Linked Laminin after 14 days. White arrows point to 2 exemplary multinucleated myotubes FIG. 6G: shows a graph comparing number MHC+ myo-fibers to the treatments shown in FIGS. 6A-6D where at both cell densities the number of myofibers growing on x-Linked ECM is almost 2-fold more than fibers grown on regular, non-cross-linked, ECM.

FIG. 7: shows Human Skeletal Myoblast-Derived Poly-Nucleated Fibers growing in microfluidic chips comparing non-cross-linked to cross-linked ECM (Laminin) where more nuclei per myo-tubes are observed growing on cross-linked ECM.

FIG. 7A, FIG. 7B, FIG. 7C, FIG. 7D: show fluorescent micrographs of immunostained myosin heavy chain (MHC) (red) myo-fibers and DAPI stained nuclei (DNA) (shown in blue) comparing cultures started at the 2 different densities with inserts showing higher magnifications of presumptive myo-fibers for each treatment.

FIGS. 7A-7B: $5 \times 10^6$/ml cells and FIGS. 6C-D: $1.6 \times 10^6$/ml cells) with Laminin (Lam) and with cross-linked (X-linked) Laminin-ECM.

FIGS. 7E-7F: Show a 3-fold higher number of nuclei in MHC myo-fibers seeded on exemplary Sulfo-SANPAH cross-linked ECM by graphical comparisons.

FIG. 7E: shows a graph comparing DAPI+ nuclei per MHC+ fiber for determining myo-fiber at the 4 treatments shown.

FIG. 7F: shows a graph comparing percentage of total DAPI+ per channel, i.e. percentage of DAPI in myo-fibers at the 4 treatments shown in FIG. 7A-D.

FIG. 8: shows one embodiment of a Human iPS-Derived MN and Muscle Cell Co-Culture in-a Tall Channel Microfluidic Chip.

FIG. 8A: shows a picture of a tall channel microfluidic chip (16) in one embodiment seeded with MNs at day 12 of culture into the port (2) of the upper (blue) channel (thick arrow) (1) and human skeletal muscle cells into the port (3) of the lower (red) channel (1) at the end of the other channel (thin arrow). The arrowhead points to a vacuum chamber (4), for optional use.

FIG. 8B: shows iPSC-derived MNs seeded into the upper channel forming a neural network stained with TUJ1 (green); Islet1 (ISL1) (blue); indicating early motor neurons, and Islet1 (ISL1) (blue); HoxB9 (red); indicating more mature motor neurons, while the third frame is a superimposed image showing both early and more mature motor neurons.

FIG. 8C: shows skeletal muscle cells seeded into the lower channel stained with myosin heavy chain (MHC) (green) with an insert showing myofibers at a higher magnification; α-bungarotoxin BTX (pre-BTX) (red), for identifying AchR in the motor end plate, with an insert showing stained cells at a higher magnification; and DNA in nuclei stained then fluoresced in the blue range, with an insert showing myofibers (green) at a higher magnification with unstained regions that likely correspond to multinuclear areas in the myofibers; and FIG. 8D: shows a schematic illustration of a vertical cross section of a tall channel microfluidic chip where MNs from a Day 12 culture seeded onto the chip develop cell bodies containing nuclei (purple circles), axons and terminal areas next to the membrane separating the top from the bottom channel containing human skeletal muscle cells growing around the edge of the channel.

FIG. 9: Shows one embodiment of a Human iPS-Derived MN and Muscle Cell Co-Culture in-a microfluidic Chip.

FIG. 9A is a picture of an exemplary microfluidic chip where day 12 MNs are seeded into the top (upper-blue) channel and hSkMCs are in the bottom (lower-red) channel;

FIG. 9B shows a schematic illustration of an exemplary cross section of NMJ microfluidic chip with day 12 MNs in the top channel and hSkMCs in the bottom channel with 3 sets of Experimental Chips for comparing cell densities at the time of seeding: Chip 1: top: $3 \times 10^6$/ml diMN cells and bottom: $5 \times 10^6$/ml hSkMC cells; Chip 2: top: $3 \times 10^6$/ml diMN cells and bottom: $10 \times 10^6$/ml hSKMC cells; and Chip 3: top: $3 \times 10^6$/ml diMN cells and bottom: $20 \times 10^6$/ml hSKMC cells.

FIG. 9C: shows a schematic illustration of a timeline showing co-culture of hSkMCs seeded Day (D) 0 with differentiation (diff) initiated on D1, Day 12 MNs seeded D1, Myofiber formation on D5, myofiber contractions observed D10, a loss of myofibers observed on D11, with fixation and analysis by ICC on D14.

FIG. 10: shows one embodiment of an experimental system (Experiment 1) as a schematic illustration for testing medium to reduce spontaneous contractions of cells in the microfluidic tall channel chip. Experimental Groups 1-3 directly compare medium harvested from diMNs/hSkMC cultures with coM media in chips containing induced motor neurons (diMNs: Motor-neuron-on Chip) and human Skeletal Muscle Cells (hSkMCs-on-Chip), each cell type growing alone on chips then combined in the same chip in the same media (upper and lower channel) for providing a neuronal-muscular-junction (NMJ-on-Chip).

FIG. 10A: Group 1: shows a schematic illustration of the tall channel chip, with vacuum chambers (4), diMNs in the top channel but no cells in the bottom channel. Group 2: shows a schematic illustration of the tall channel chip with no cells in the top channel but with hSkMCs in the bottom channel. Group 3: shows a schematic illustration of the tall channel chip with diMNs in the top channel and hSkMCs in the bottom channel for providing a NMJ-on-Chip.

FIG. 10B: shows a schematic illustration of cells numbers and media used for growing cells: Group 1: Top: $3 \times 10^6$ diMNs Bottom: none. Group 2: Top: none. Bottom: $10 \times 10^6$ hSkMCs. Group 3: Top: $3 \times 10^6$ diMNs. Bottom: $20 \times 10^6$ hSkMCs.

FIG. 11: Shows human skeletal muscle cells (hSkMCs) forming myofibers within 8 days post seeding (co-cultures) having spontaneous myo-tube contractions at Day (D) 10 culture that are reduced by using conM culture medium in a microfluidic chip.

Inserts show higher magnified areas of cells outlined in the white box for each micrograph.

FIG. 12: Shows human skeletal muscle cells (hSkMCs) as myofibers with spontaneous myotube contractions at Day (D) 10 (Experiment 3).

FIG. 12A: shows a micrograph of hSkMCs as myotubes growing on top of a membrane of the microfluidic chip in coM media.

FIG. 12B: shows a graph comparing contractions per minute for a myofiber contraction frequency with an average of fibers in two experiments (Experiment 1 and 3) that were combined for a total estimation of myofiber contraction frequency.

FIG. 12C: shows a graph comparing contractions per minute for myofibers having an increased myofiber contraction frequency of myotubes grown on cross linked Laminin ECM over non-cross-linked Laminin covered surfaces.

FIG. 12D: shows a graph comparing contractions per minute for myofibers grown in regular media compared to a culture grown in coM media. When cultured in coM, contraction frequency is around 25% less compared to regular medium conditions.

FIG. 13: shows schematic illustrations of experimental timelines for comparing co-cultures of hSkMCs with MNs, with and without coM media.

FIG. 13A: shows a schematic illustration of a timeline and cell densities for Group 1 and Group 2 in coM: hSkMCs seeded at $5\times10^6$/ml cells and MNs seeded at $3\times10^6$/ml cells. hSkMCs seeded Day (D) 0 with differentiation (diff) initiated on D1, Day 12 MNs seeded D1 (as one example 18h later), D5 formation of myotubes & medium switch to coM, no myofiber contractions observed D10, no loss of myofibers observed on D12, fixation and analysis by ICC on D14, duplicate chips on D20 showed no loss of myofibers.

FIG. 13B: shows a schematic illustration of a timeline and cell densities for Group3: hSKMCs seeded with MNs: Day 0: seeding hSKMCs; Day 1: (18 h later) seeded diMNs (d12); Day 5: formation of myotubes, no medium switch; Day 10: observation of myofiber contraction; Day 11: observing progressive loss of myofibers; Day 14: fixation and analysis by ICC; in chip cultures left to D20, there is almost a complete loss of myofibers.

FIG. 14: Shows schematic illustrations of embodiments of a microfluidic device.

Figure 14B:
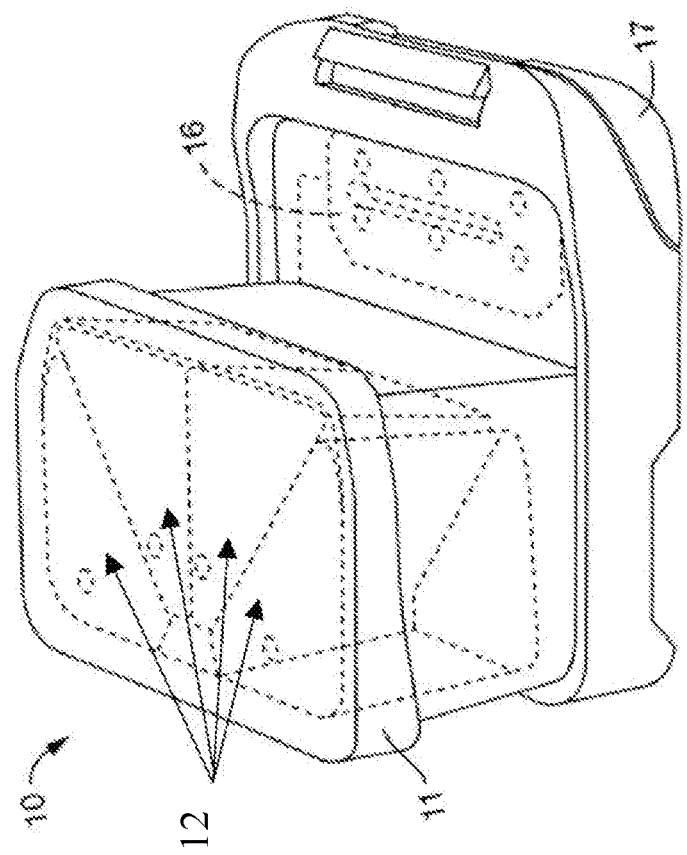
Figure 14A:
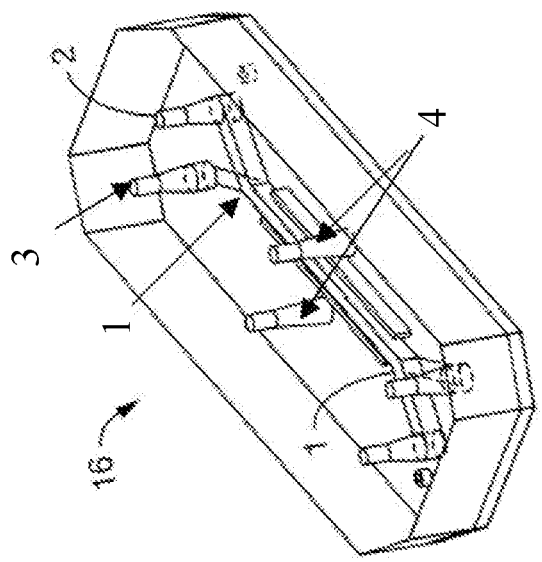

FIG. 14A: is a schematic illustration showing one embodiment of the microfluidic device or chip (16), including two microchannels (1), each with an inlet and outlet port for the upper channel (2) and lower channel (3), as well as (optional) vacuum ports (4).

FIG. 14B: is a topside schematic of an embodiment of the perfusion disposable or "pod" (10) featuring the transparent (or translucent) cover (11) over the reservoirs (12), with the chip (16) inserted in the carrier (17). The chip can be seeded with cells and then placed in a carrier for insertion into the perfusion disposable or pod, whereupon culture media in the reservoirs flows into the microchannels and perfuses the cells (e.g. both MNs and hSMCs).

FIG. 15: Shows schematic illustrations showing one embodiment of microfluidic devices, including for providing an "air dam" for isolating one channel.

Figure 15A:
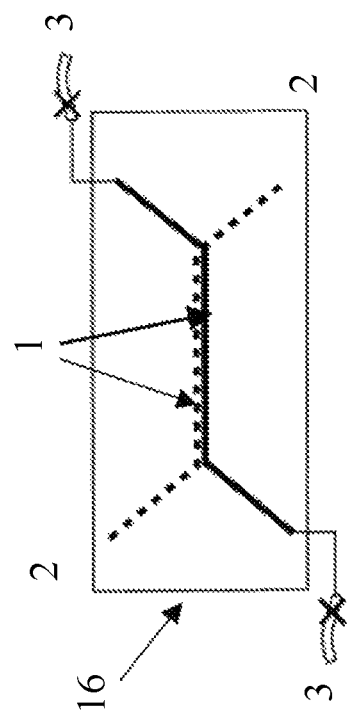

FIG. 15A: is a schematic illustration showing one embodiment of a microfluidic device or chip (16) (viewed from above), the device includes top (apical; dotted line) and bottom (basal; solid line) channels. As an example, motor neurons are seeded into the upper (apical) channel and human skeletal muscle cells are seeded into the lower (basal) channel. In one embodiment, an "air dam" is created for part of a protocol, described below, where the two Xs are indicating that channels are blocked during at least part of the protocol.

Figure 15B:
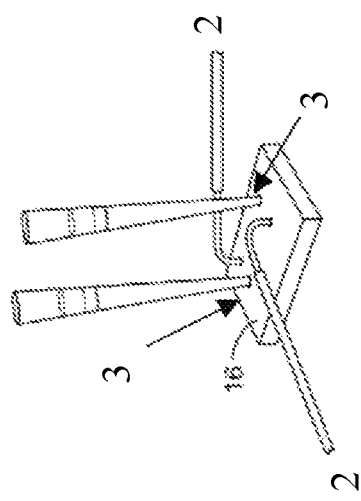

FIG. 15B: is a schematic illustration showing one embodiment of how ports, upper (2) and lower (3) of a microfluidic device or chip (16) can be utilized to deposit fluids carrying surface coatings (e.g. dissolved proteins) and/or seed the cells using pipette tips. This image, in part, shows one embodiment of a modification to the typical chip ECM coating protocol based on the need in some embodiments to coat the top and/or bottom channels with different ECM solutions in wet and/or dry conditions.

FIG. 16: shows schematic illustrations of tall channel microfluidic NMJ-on-chip with one embodiment of an experimental timeline (Experiment 4) set up and time course for comparing co-cultures of hSkMCs with MNs under flow for longer culture times.

Figure 16A:
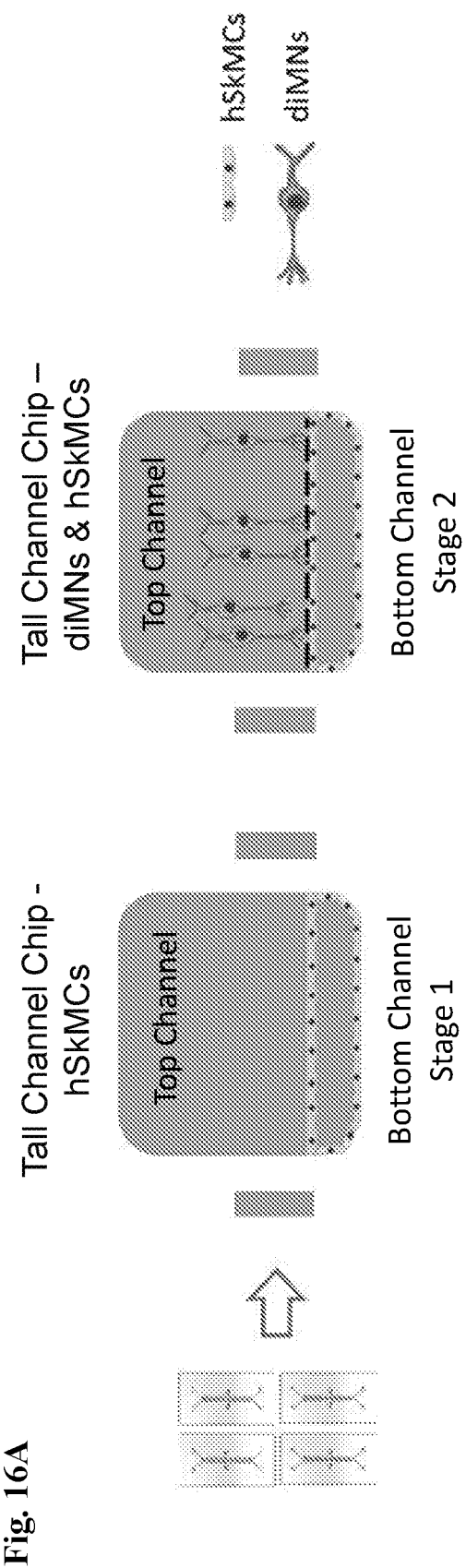

FIG. 16A: shows a schematic illustration of a tall channel microfluidic chip, from left to right, view of vertical 2-channel chip (i.e. the top channel is above the bottom channel as shown in Stage 1, with hSkMCs covering the entire surface of the bottom channel, and Stage 2 with diMNs seeded into the top channel.

Figure 16B:
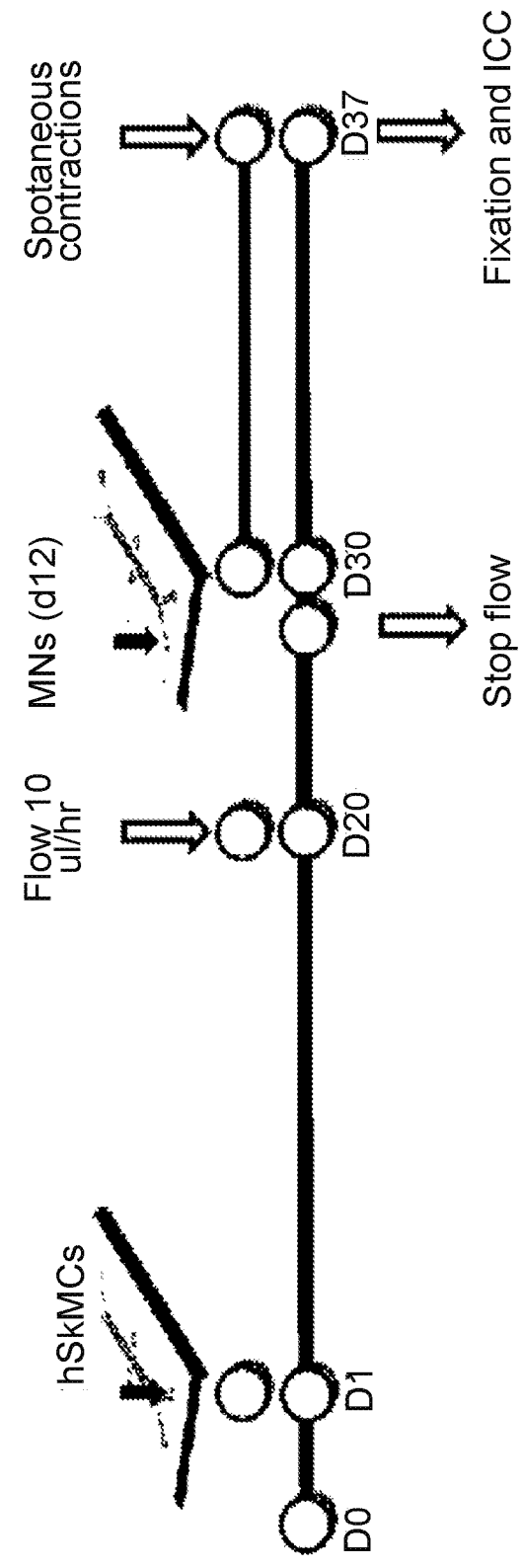

FIG. 16B: shows a schematic illustration of one embodiment of a timeline where hSkMCs are seeded Day (D) 0 with differentiation (diff) initiated on D1, D5: formation of myotubes & medium switch to coM media, then Day 7-10: no myofiber contraction, on Day 20 start muscle cells under flow at 10 ul/hour, continued to D29 when flow is stopped. Day 30: seed diMNs (d12) (not in coM media for observing baseline contractions). Day 37: myotubes are spontaneously contracting: fixation and analysis (including ICC).

FIG. 17: shows an exemplary co-localization study of iPS-Derived MNs and Muscle Cells showing formation of NMJs between diMNs and hSkMCs (Experiment 4). Cells were stained with α-bungarotoxin (BTX) for identifying suggestive NMJ areas where motor end plate (green), neurons are stained with Tubulin beta-3 chain (Tubb3) (red) and muscle myosin heavy chain (MHC) (blue) were fluorescently imaged on individual channels then merged. The blue channel of MHC staining is not shown in FIG. 17A-17D.

FIG. 17A: shows a low power fluorescent micrograph where Tubb3 (red) neuronal staining shows neurite extension along myotubes with oval areas (green) suggestive of lower motor nerve termini whose distribution over a myotube suggests motor end plates.

FIG. 17B, FIG. 17C, FIG. 17D, FIG. 17E, FIG. 17F, FIG. 17G: shows higher power fluorescent micrographs of the suggestive NMJ areas (white arrows) are identified by superimposed staining i.e. co-localization, where the red stained nerve terminal neuron bulb is co-localized with BTX green staining of motor end plates producing a yellow NMJ.

FIG. 17E-17G: The blue channel of MHC staining is shown showing a MHC containing muscle fiber at the yellow stained NMJ.

FIG. 18: shows florescent micrographs of stained cells in a microfluidic chip. Co-Localization Study of iPS-Derived MNs and Muscle Cells. Both diMNs and hSkMCs are in close proximity to each other as determined from initial ICC analysis and 3D reconstruction of confocal microscope images (i.e. combined z-stacks). A partial loss of myotubes were observed due to lack of ECM stability FIG. 18A and FIG. 18B: α-bungarotoxin (BTX) for identifying the motor end plate (green), skeletal muscle marker, desmin, (red) and DNA (DAPI) (shown in blue). The red muscle fiber is multinucleated with numerous green motor end plates.

Figure 18A:
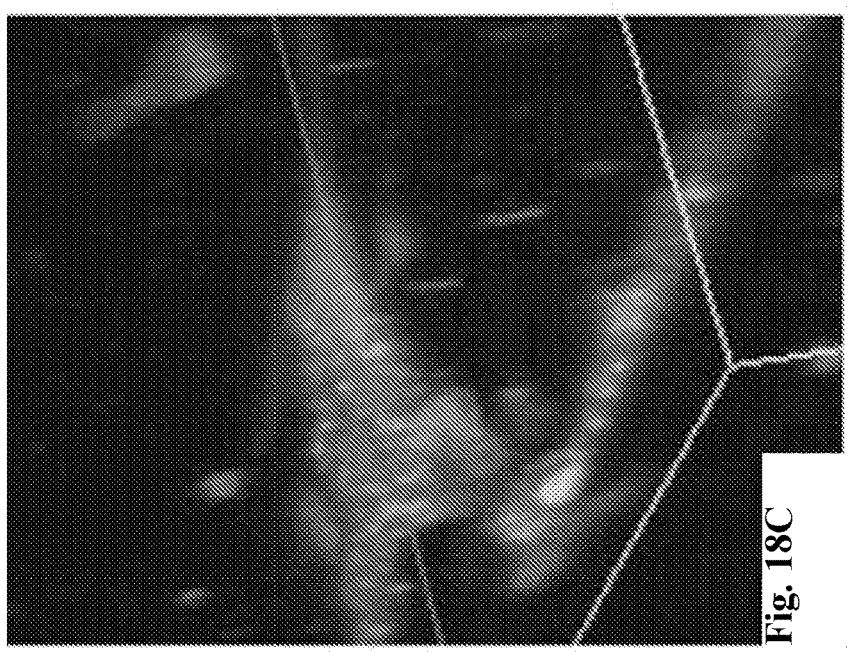
Figure 18B:
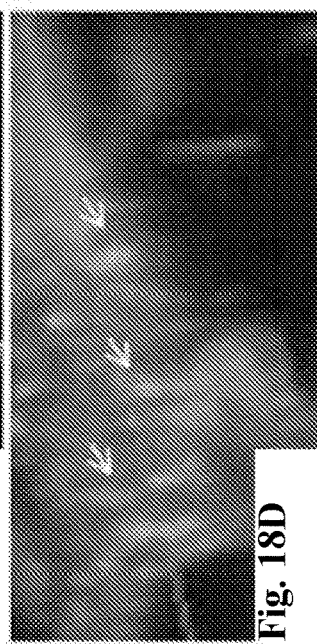

FIG. 18B: a higher magnification of FIG. 18A, 3 white arrows point to co-localization of α-bungarotoxin (BTX) for identifying the motor end plate (green) and skeletal muscle marker, desmin, (red) as olive, white dark orange areas depending upon concentration of stain.

Figure 18C:
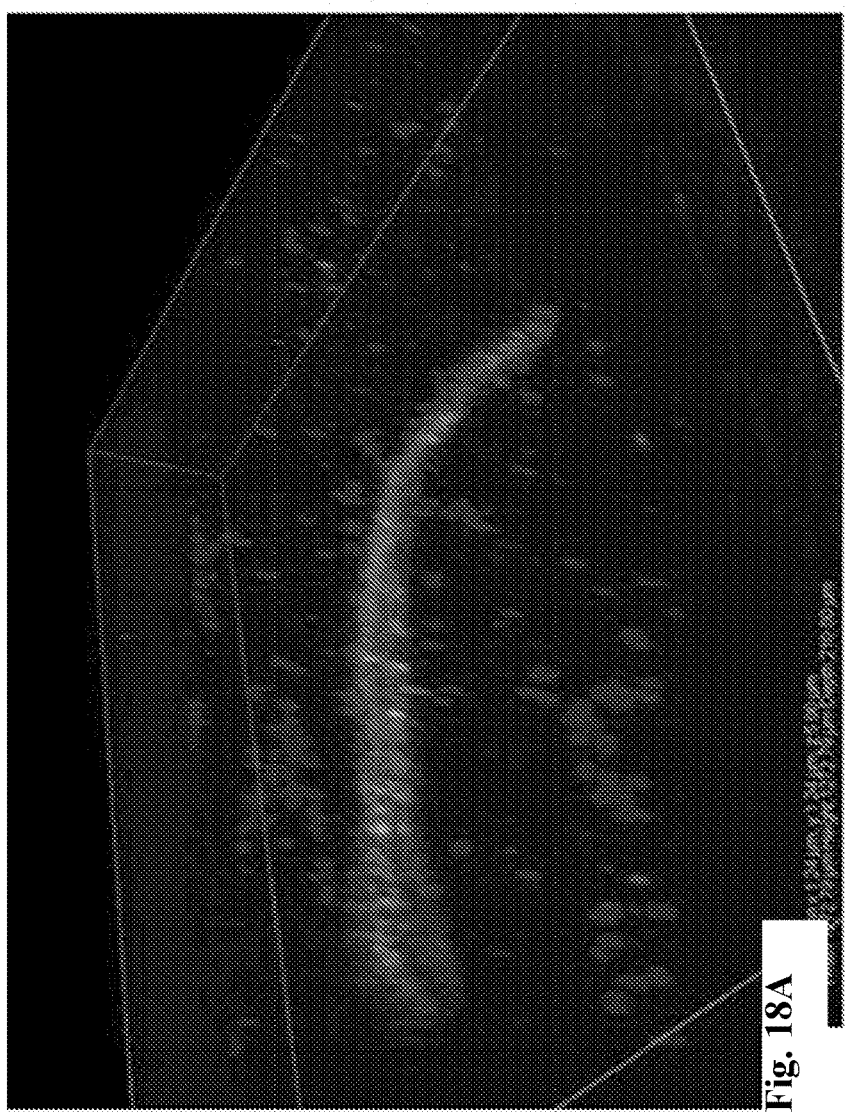
Figure 18D:
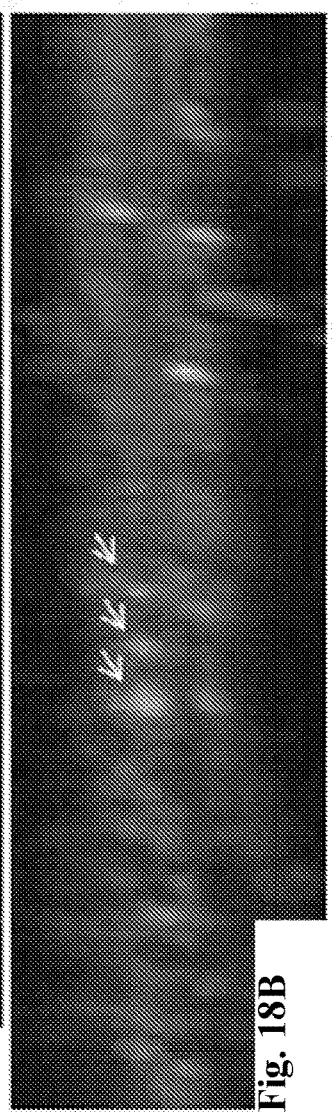

FIG. 18C and FIG. 18D: motor end plate (green) BTX and neurofilament H non-phosphorylated (SMI 32) (red) and DNA (DAPI) (shown in blue).

FIG. 18D: a higher magnification of FIG. 18C, 3 white arrows point to co-localization of a motor end plate (green)

BTX, neurofilament H non-phosphorylated (SMI 32) (red) as olive—white areas depending upon concentration of stain.

FIG. 19: shows schematic illustrations of one embodiment of experimental timelines for using NMJ-on-chips (Experiment 5) as a set up and time course for using co-cultures of hSKMCs with MNs for live imaging and pharmacology studies.

Figure 19A:
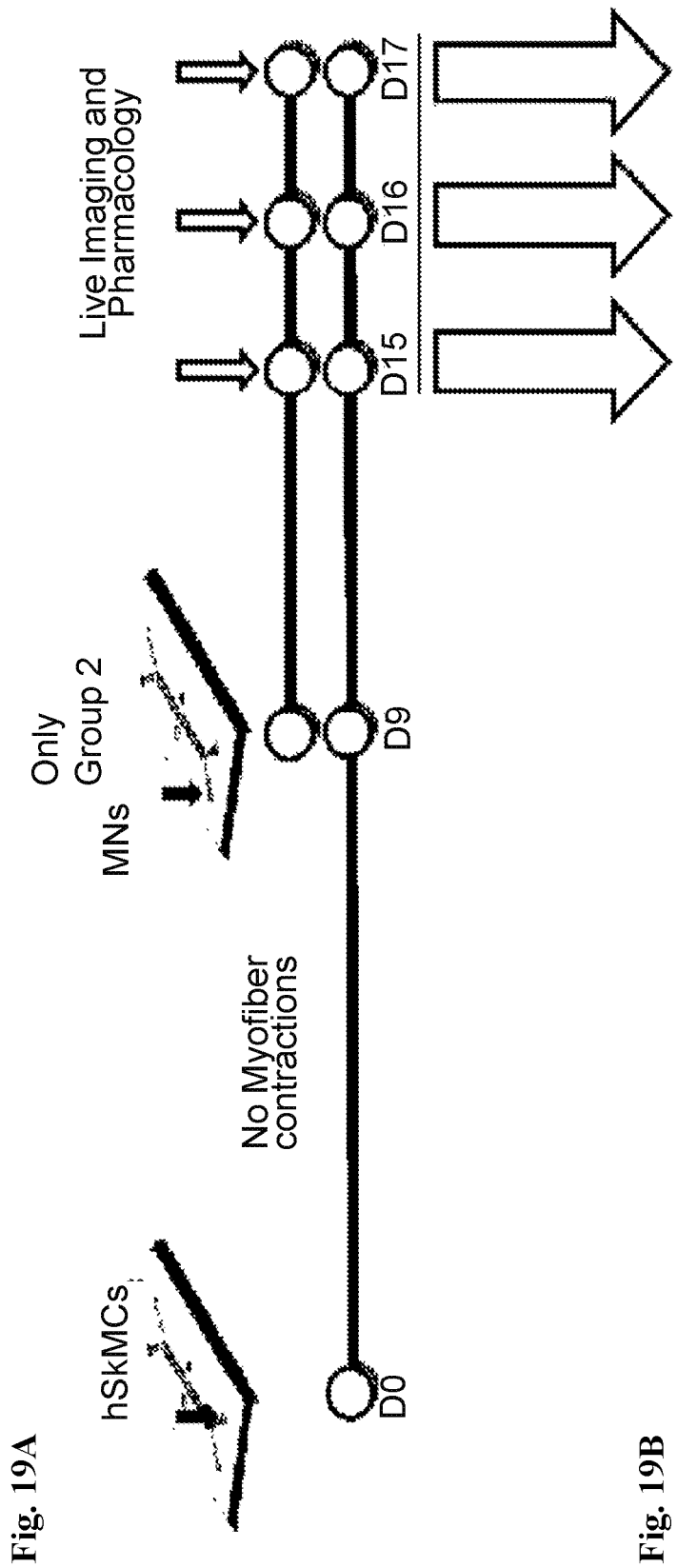

FIG. 19A: shows a schematic illustration of a tall channel microfluidic chip, seeded with hSKMCs at Day 0 (D0) in the bottom channel, culting up to D9, without observing muscle contractions, then D9 seeding diMNs (d12). In one embodiment only in Group 2. In some embodiments, more than one group of hSKMCs receive MNs. On days 15, 16 and/or 17, live imaging of pharmacology assays are done as shown schematically, for one example, in FIG. 19B.

Figure 19B:
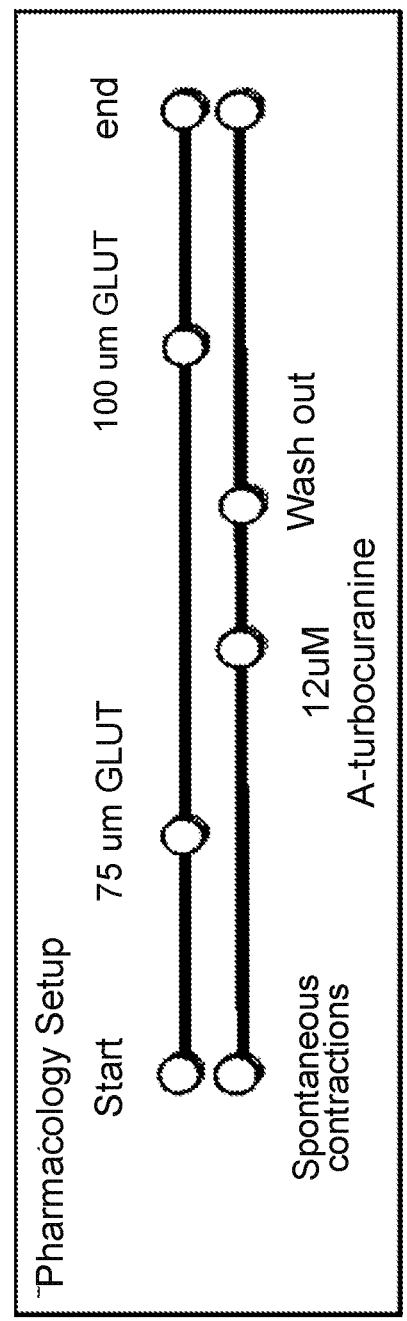

FIG. 19B: shows a schematic illustration of one embodiment of a timeline where a NMJ-On-Chip with spontaneous contracting muscle fibers is used for a pharmacology study, i.e. testing agents for inducing or reducing muscle contractions on a baseline chip with or without spontaneously contracting myofibers, in one embodiment, treating NMJ chip with 75 uM Glutamine (Glut) in the NM (upper) channel), in one embodiment, treating NMJ chip with 12 uM alpha-turbocurarine in the hSKMC (lower) channel), in one embodiment, washing out alpha-turbocurarine, in one embodiment, treating NMJ chip with 100 uM Glutamine (Glut) in the NM (upper) channel).

FIG. 20: Shows exemplary High Content Imaging as immunohistochemistry of iPSC derived Myo-fibers, on fixed cells (Experiment 5).

Figure 20A:
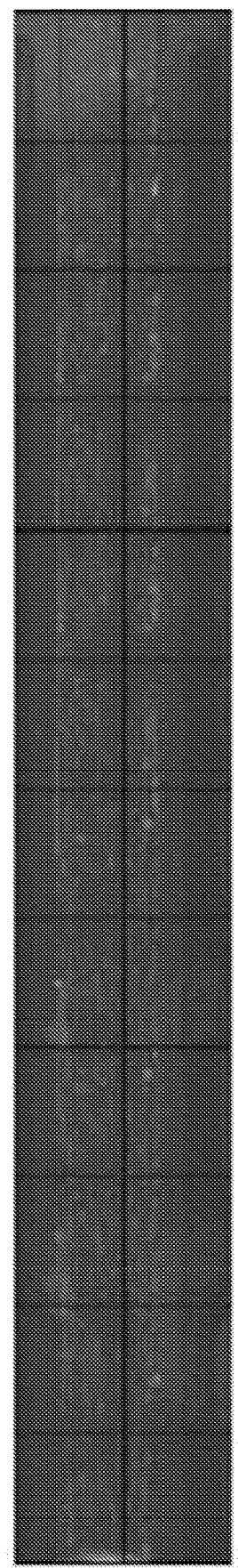

FIG. 20A: shows a fluorescent micrograph of the entire width and length of immunostained cells in a microfluidic NMJ chip. α-bungarotoxin BTX (green), Neuron-specific Class III β-tubulin (TuJ1) (red) and myosin heavy chain (MHC) (blue).

Figure 20B:

FIG. 20B: shows a higher power fluorescent micrograph of the channel in the chip shown in FIG. 20A.

FIG. 21: shows micrographs of cells grown as shown in Experiment 5 for pharmacology and in-chip imaging for NMJ-On-Chip.

Figure 21B:
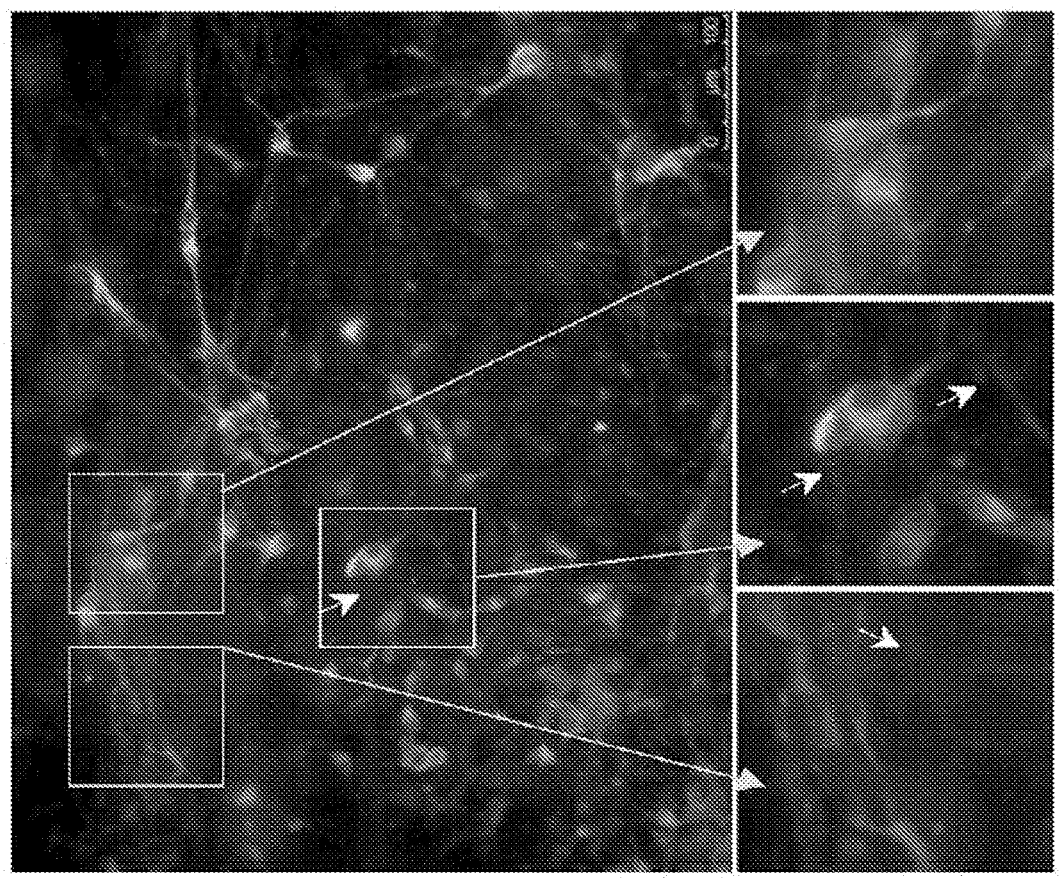
Figure 21A:
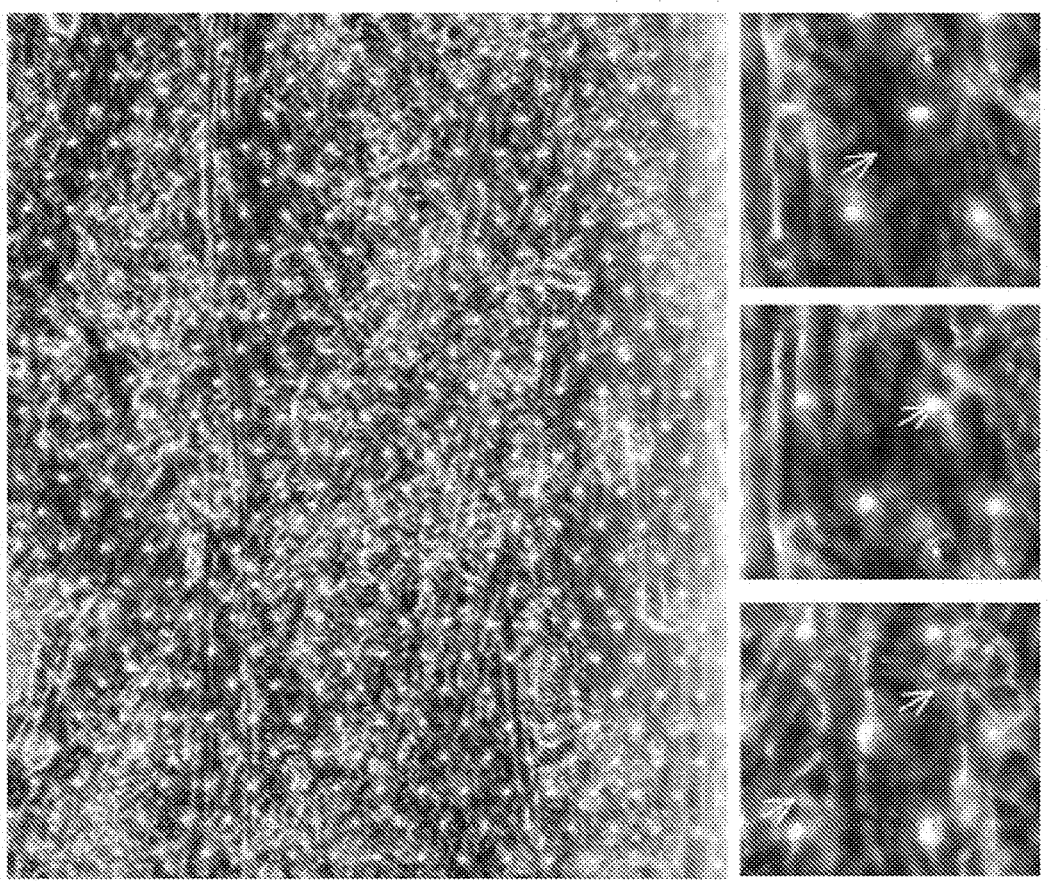

FIG. 21A: shows phase contrast micrographs of myotubes and neurons in chips, higher magnified areas are shown below the larger micrograph white arrows point to potential NMJs where myotubes are adjacent to neurons.

FIG. 21B: shows fluorescent micrographs of superimposed (co-localized images) of neurons stained with a neuronal microtubule marker, Tau, (green) a microtubule stabilization protein, for identifying neurons and motor end plates with BTX (red) (labeling AChRs) for identifying NMJs, where neuronal braches co-localize with end plates. Smaller micrographs show higher magnified areas outlined by corresponding white boxes. White arrows point to motor end plates of myotubes, some of which are in close proximity to neuronal axons.

FIG. 22: shows an exemplary method of growing motor neurons in a microfluidic chip where the MN cells of neural networks have spontaneous calcium bursts.

FIG. 22AA: shows a microfluidic chip seeded with MNs at day 12 of culture.

FIG. 22BB: shows an exemplary timeline where MN precursor cells from Day 12 cultures are seeded at Day 0 in the microfluidic chip, MN network formation is observed a Day 10 on the chip (Day 18 overall from the start of the original MN culture).

FIG. 22CC: shows exemplary images produced by high content life imaging of cells in chips showing Ca++ imaging of diMN cells on Day 12 after seeding onto the microfluidic chip; at high magnification (20×). diMNs show repetitive calcium bursts as visualized via Flou4 labeling in color within the cellular areas, e.g. cell bodies, axons and terminal bulbs, in neuronal networks, where the concentrations of Ca++ are shown by yellow-lower levels, red-higher than yellow areas and highest levels in white areas within the red areas, as shown in the neuron cell bodies.

FIG. 22A: shows exemplary Ca++ imaging of FIG. 22CC in black and white, where the highest amounts of Ca++ are white areas in black and white micrographs, white arrowheads point to cellular areas with concentrated Ca++.

FIG. 22B: shows a higher magnification of a cell in the center of the micrograph in FIG. 22CC/FIG. 22A with two white arrowhead markers used to identify the same area through the different planes of focus.

FIG. 22D, FIG. 22E, FIG. 22F, FIG. 22G, FIG. 22H, FIG. 22I, and FIG. 22J: shows exemplary Ca++ imaging in color from confocal high content micrograph z-stack layers through the cell (shown in FIG. 22B) where higher concentrations of Ca++ are shown by yellow/red/white areas in the neuronal cytoplasm, which discharge and recharge then discharge over time. White arrowheads mark the same location of the cell shown in FIG. 22B-FIG. 22J.

FIG. 22K: shows a graph of average intensity of Ca++ vs. elapsed time (seconds).

FIG. 23: shows exemplary fluorescent micrographs of NMJ-On-Chips using iPSC derived Myo-fibers (iSKMCs) as superimposed (co-localized images) of neurons and myotubes.

FIG. 23A: shows a fluorescent micrograph of nerve axons (red) parallel to multinucleated (blue) muscle heavy chains within muscle myofibers (green) showing separation between internal myosin and external nerve fibers. Myosin (MHC: myosin heavy chain) (green), neuronal nerve fibers TuJ1 (red) and DNA (DAPI) (shown in blue) FIG. 23B: shows a fluorescent micrograph view on end (as compared to the orientation in FIG. 23A) for a different view, i.e. x-z image, of muscle Myogenin (green), nerve TuJ1 (red) and DNA (DAPI) (shown in blue) where nuclei superimposed on the muscle staining shows light blue, see example at the white arrow.

Figure 24:
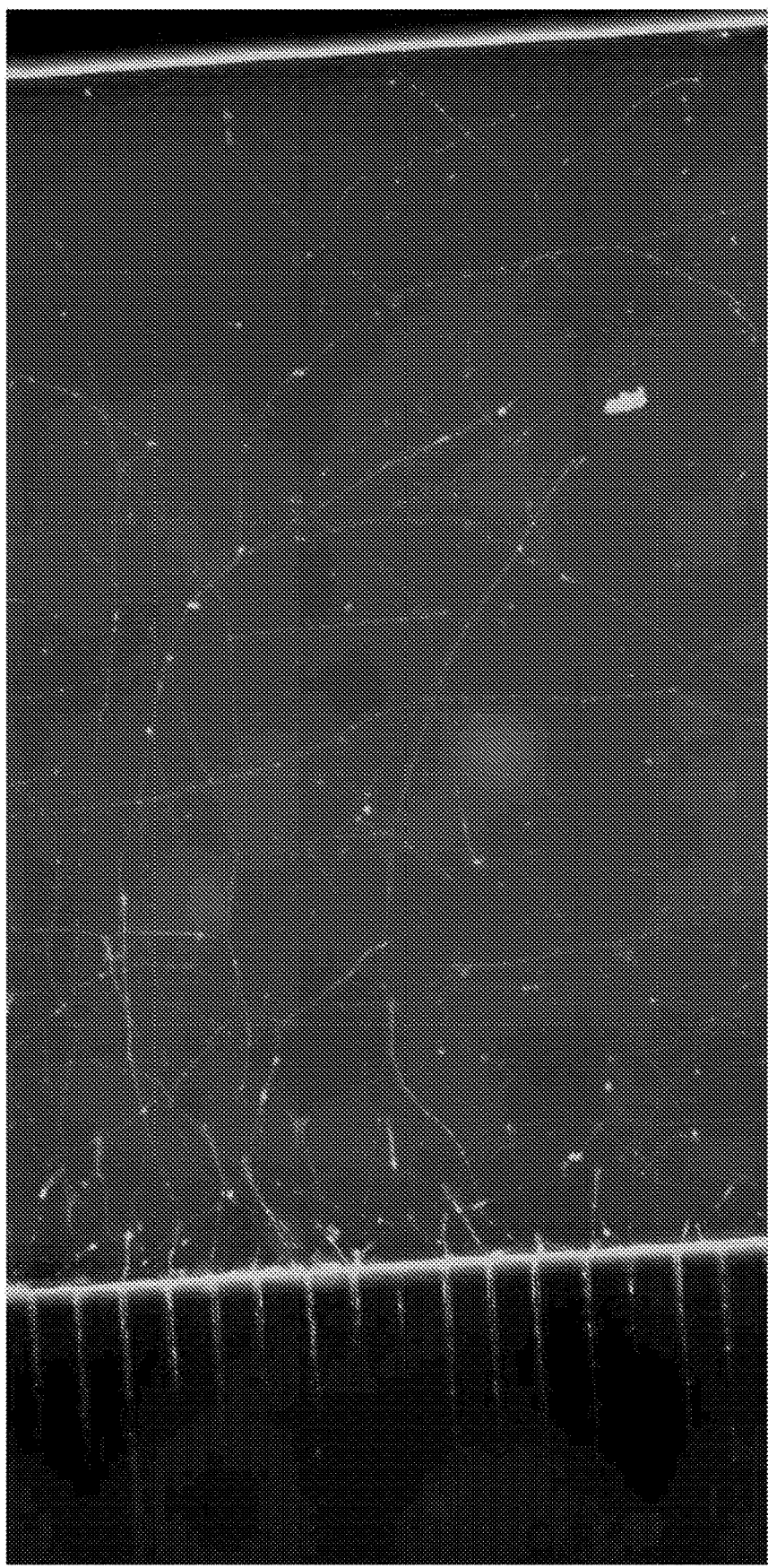

FIG. 24: iPSC derived motor neurons on XONA microfluidic device. Cells were labeled using MitoTracker green.

Figure 25:
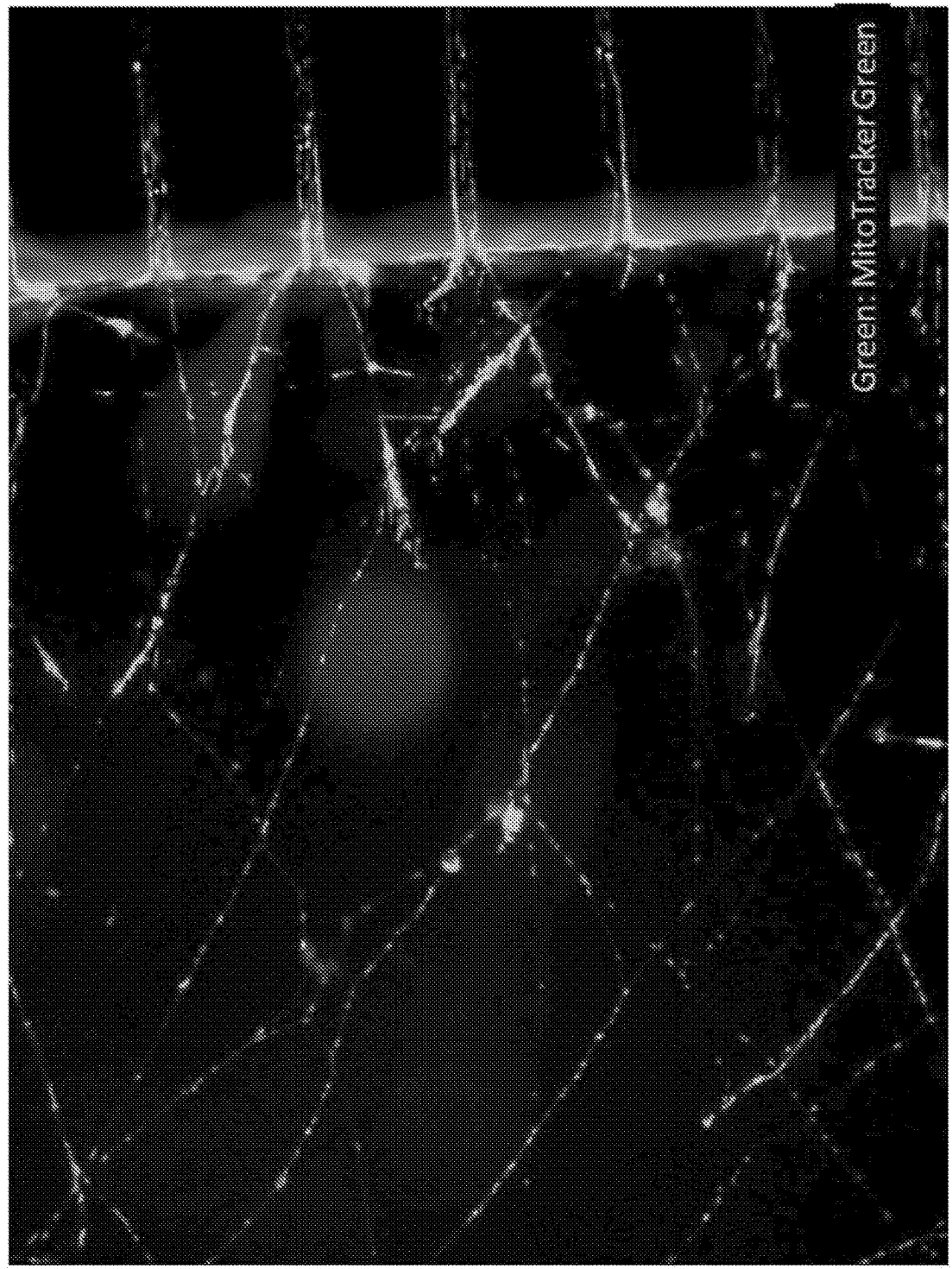

FIG. 25: iPSC derived motor neurons on XONA microfluidic device. Cells were labeled using MitoTracker green.

Figure 26:
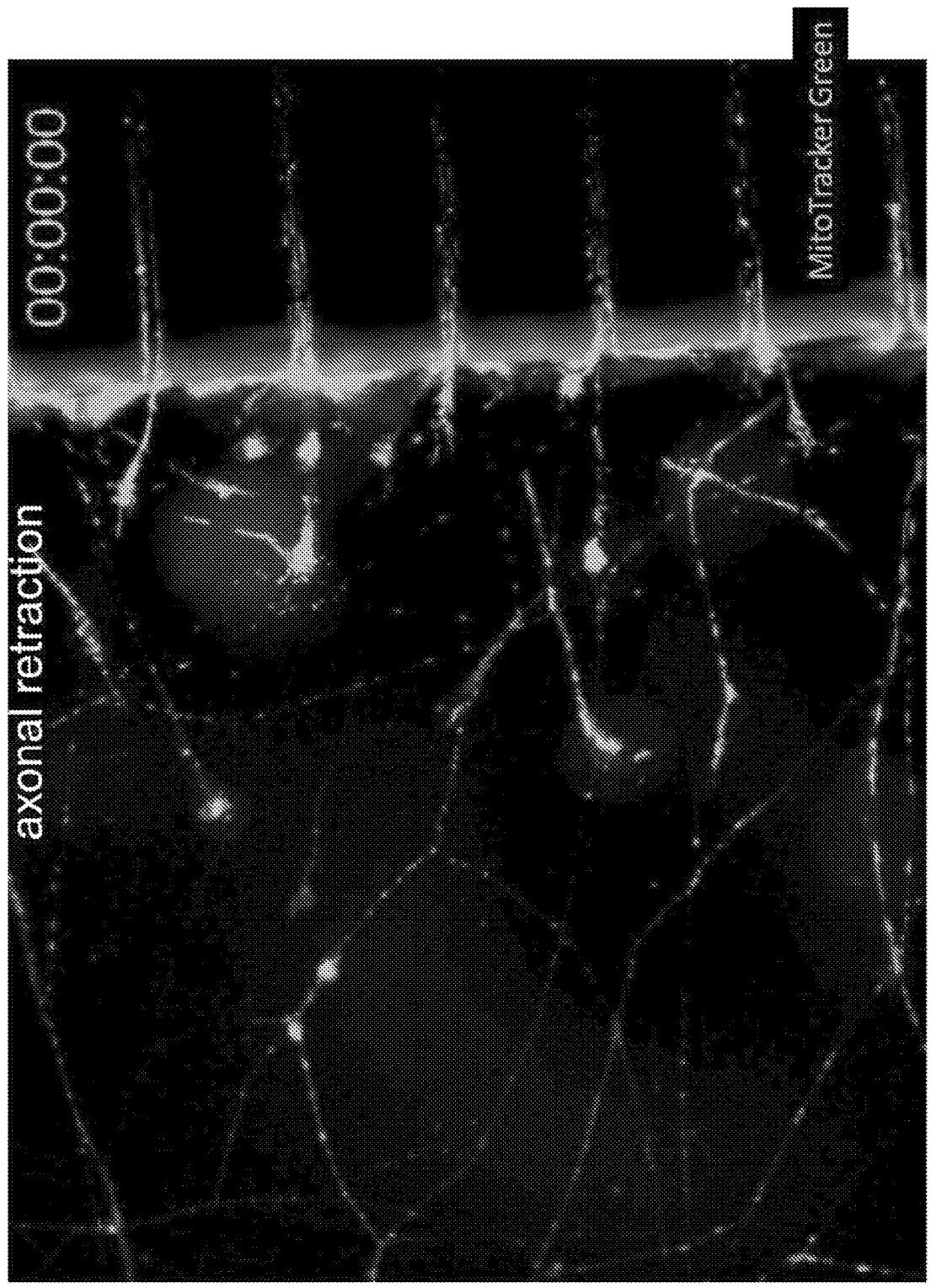

FIG. 26: iPSC derived motor neurons on XONA microfluidic device. Cells were exhibited capacity for axonal retraction.

Figure 27:
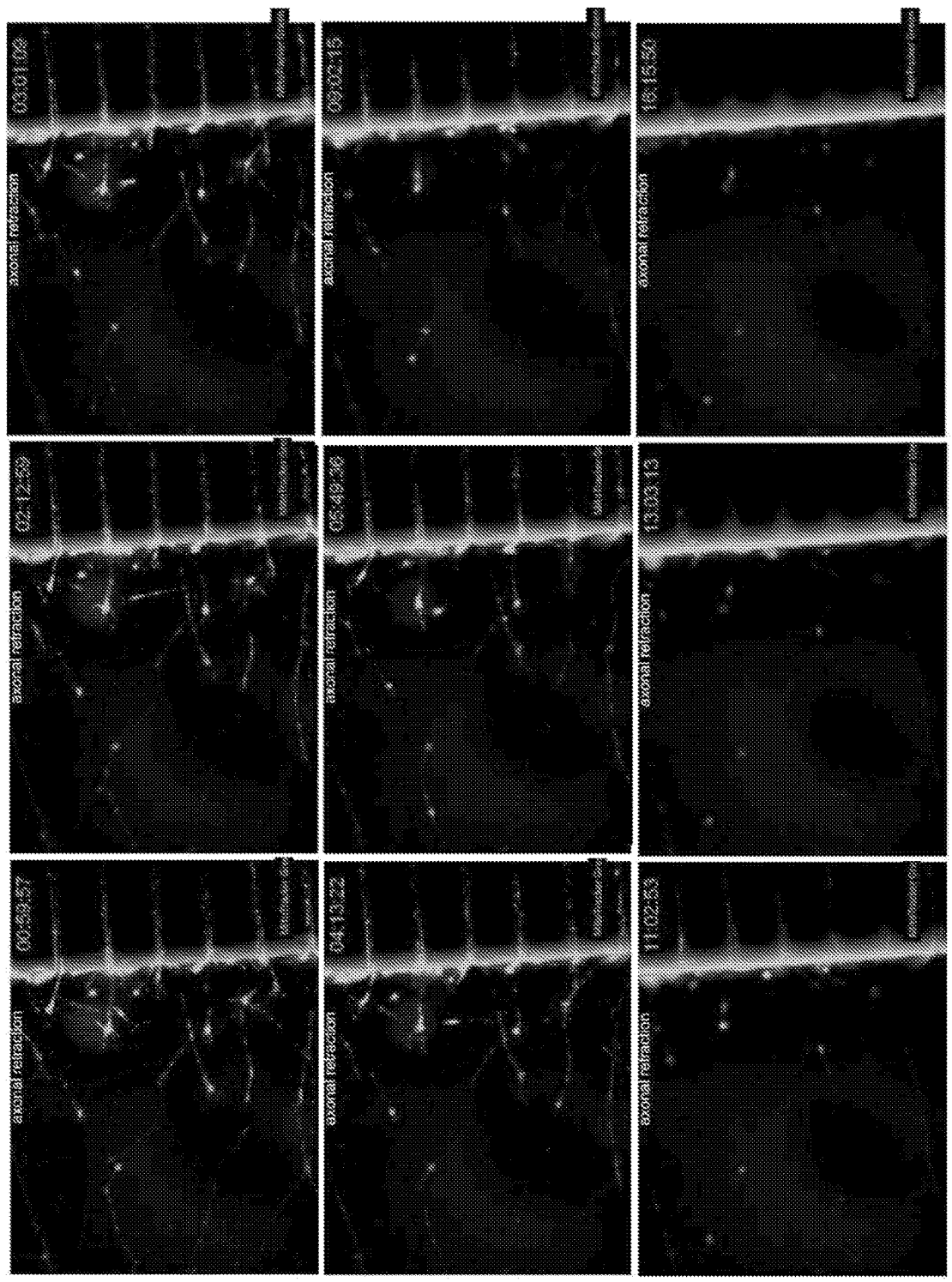

FIG. 27: Timelapse of axonal retraction at approximately 1, 2, 3, 4, 6, 9, 11, 13 and 16 hour timepoints as indicated.

Figure 28:
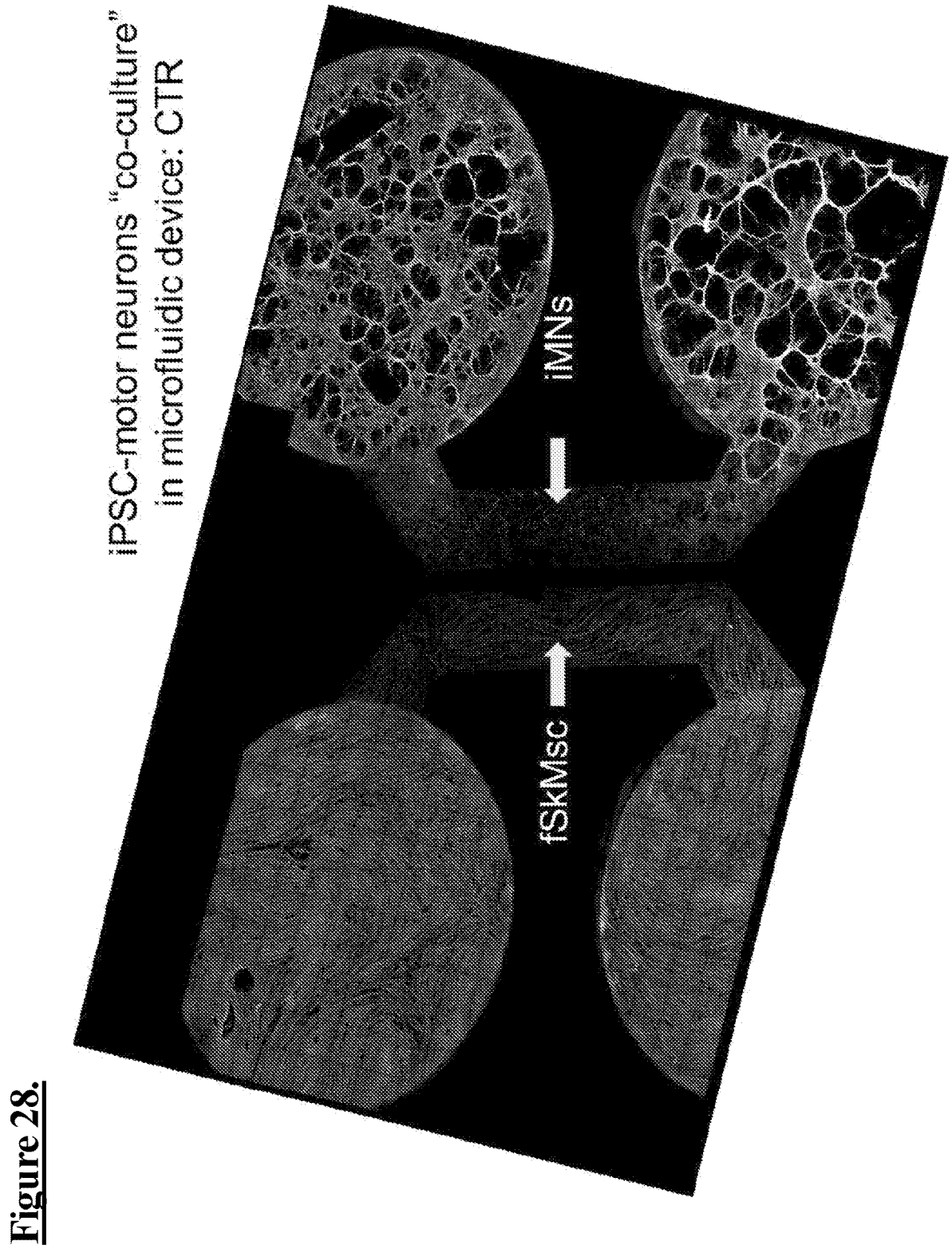

FIG. 28: iPSC-motor neurons "co-culture" in microfluidic device: control (CTR). Microfluidic device, such as optically transparent and biologically inert Polydimethylsiloxane (PDMS) possesses multiple chambers connected by microgrooves. The chamber allows fluidic communication with different cell types. Hydrostatic pressure between the two chambers separated by the microgrooves can allow one to fluidically isolate each chamber by keeping the volumes in the wells on one side of the device higher than the other side of the device. The difference in volume creates hydrostatic pressure, thus fluidically isolating each compartment. Control cells are seeded here for illustration.

Figure 29:
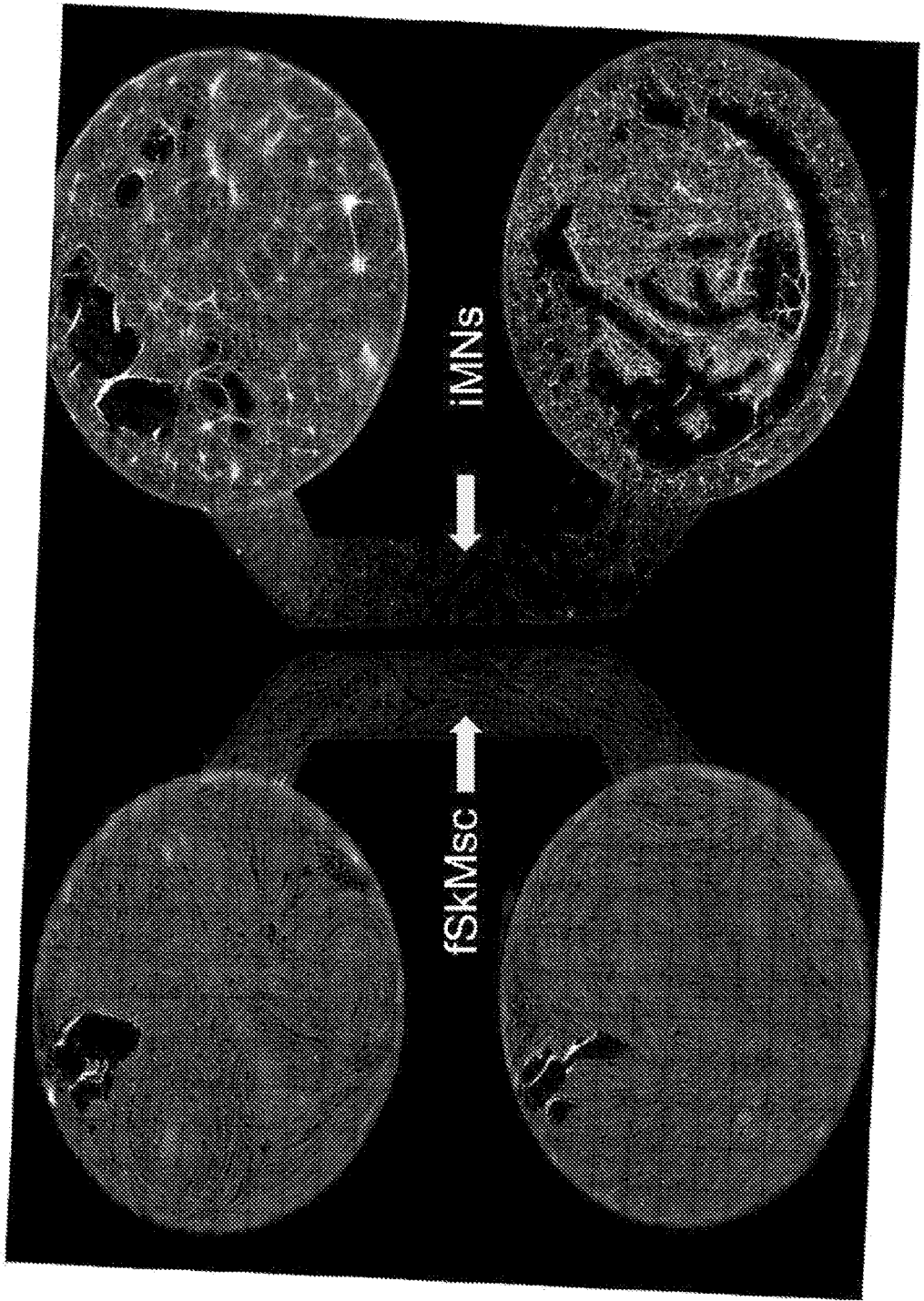

FIG. 29: iPSC-motor neurons "co-culture" in microfluidic device: spinal muscular atrophy (SMA).

Figure 30:
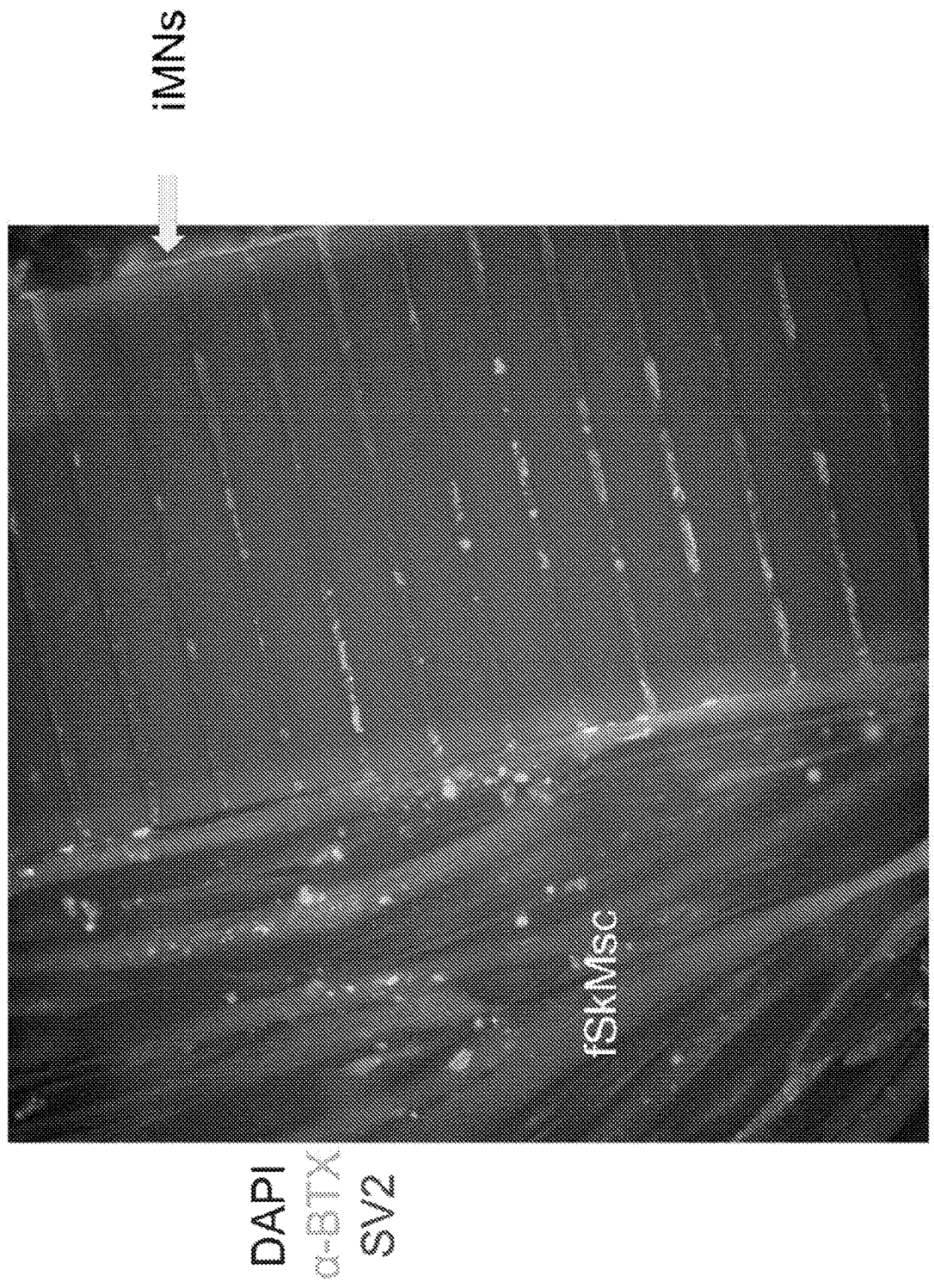

FIG. 30: iPSC-motor neurons "co-culture" in microfluidic device: control (CTR). Various labeling agents, including α-bungarotoxin (BTX), synaptic vesicle 2 (SV2) can aid visualization of the neuromuscular junction including co-localization of these markers as depicted.

Figure 31:
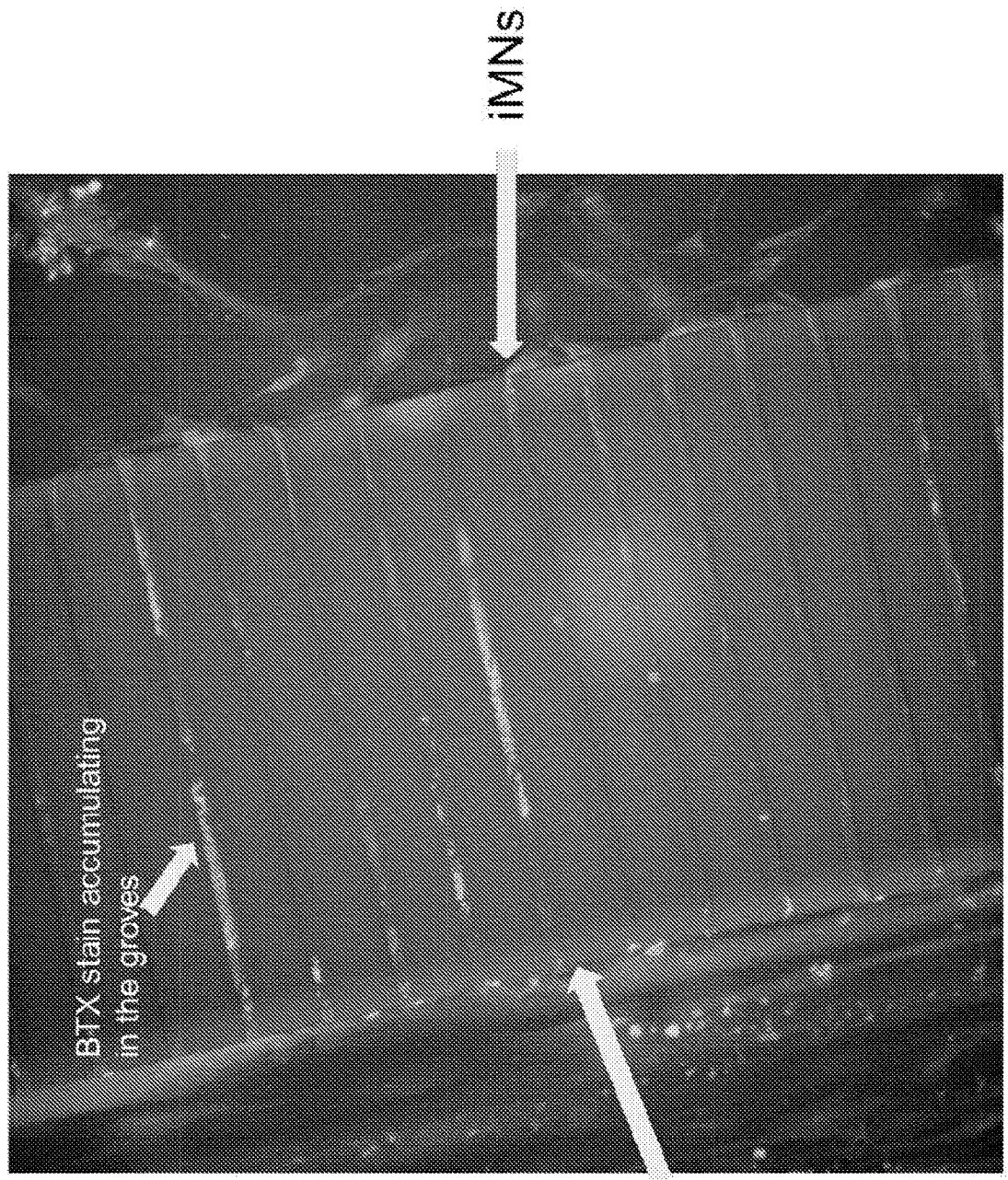

FIG. 31: iPSC-motor neurons "co-culture" in microfluidic device: control (CTR).

Figure 32:
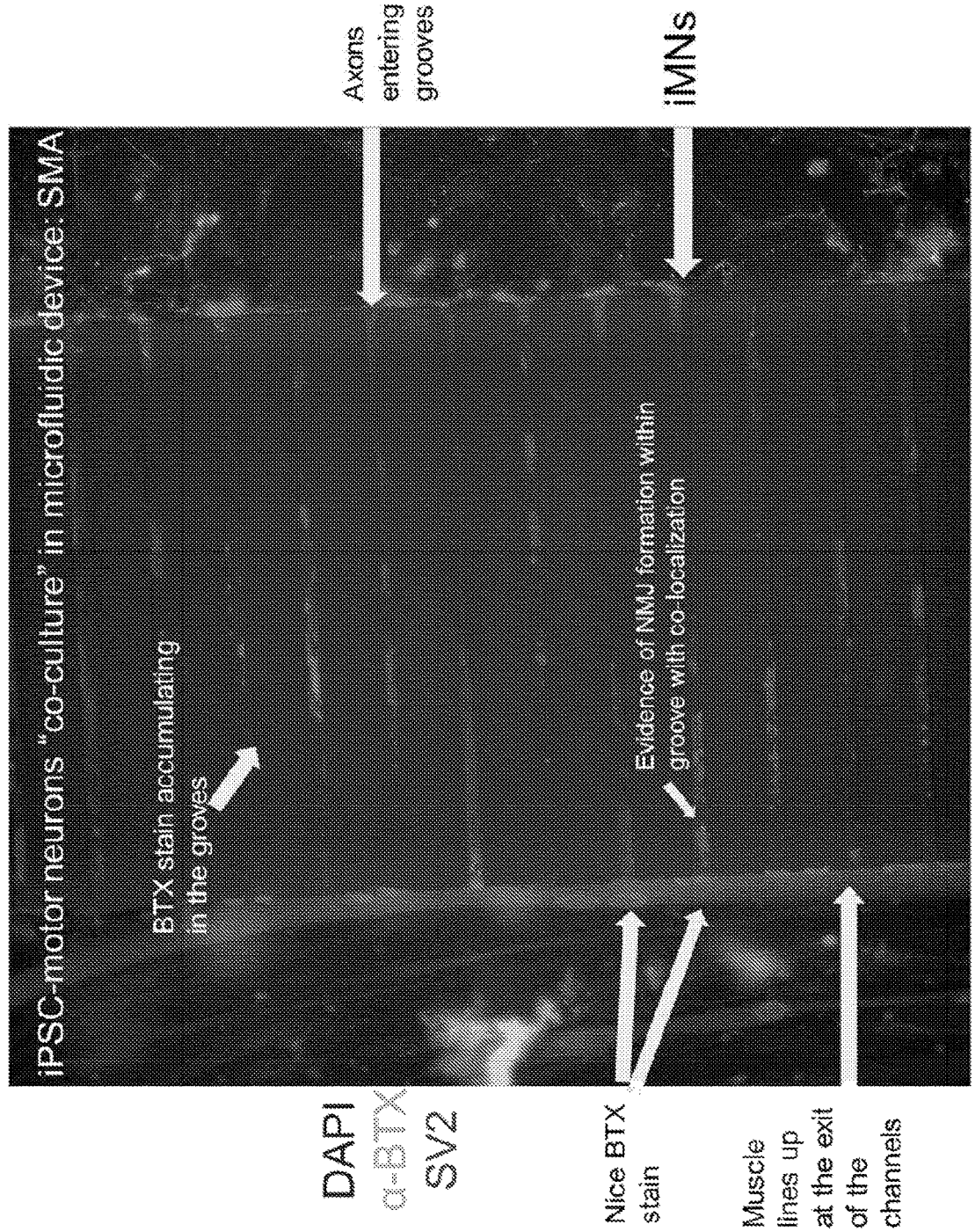

FIG. 32: iPSC-motor neurons "co-culture" in microfluidic device: spinal muscular atrophy (SMA). As shown, muscle cells are observed as aggregating at the exist of channels in fluidic connection with motor neuron cells.

Figure 33:
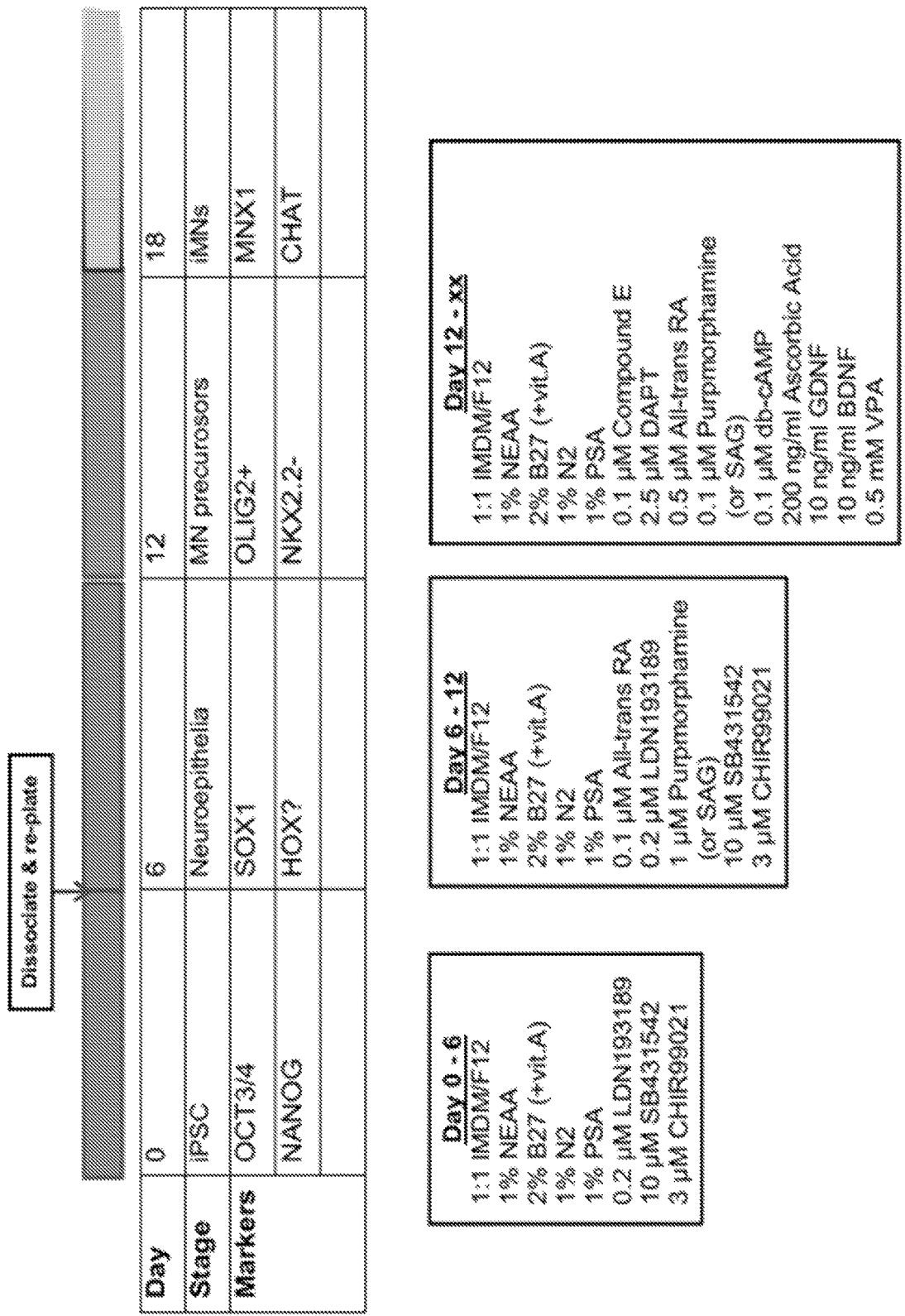

FIG. 33: Exemplary factors and a timeline for differentiation used herein for the generation of motor neurons are provided (using iPSCs as the starting material).

Figure 34:
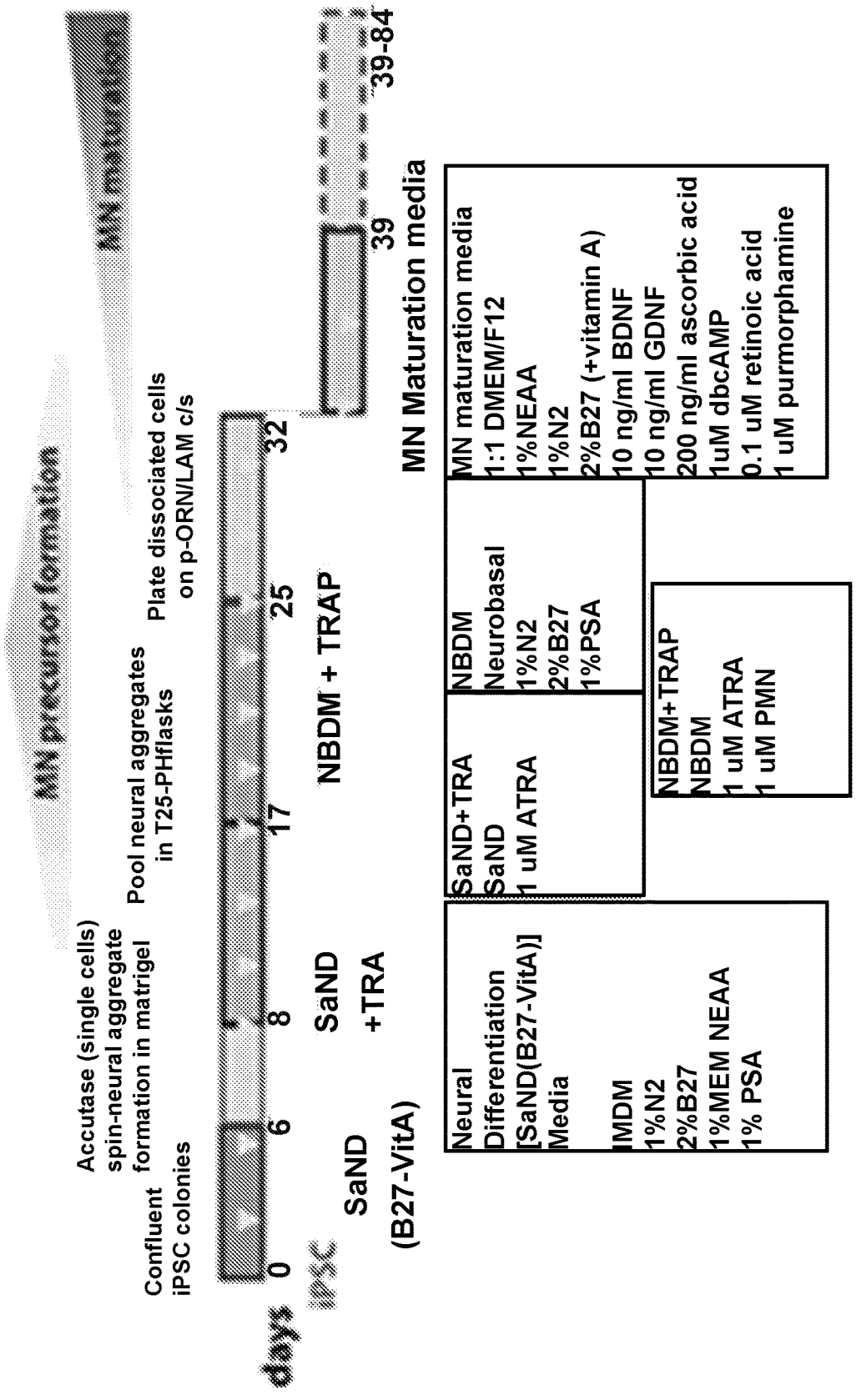

FIG. 34: Induced pluripotent stem cells (iPSCs) differentiated into motor neurons.

DETAILED DESCRIPTION OF THE INVENTION

The invention relates to culturing motor neuron cells together with skeletal muscle cells in a fluidic device under conditions whereby the interaction of these cells mimic the structure and function of the neuromuscular junction (NMJ) providing a NMJ-on-chip. Good viability, formation of myo-fibers and function of skeletal muscle cells on fluidic chips allow for measurements of muscle cell contractions. Embodiments of motor neurons co-cultures with contractile myo-fibers are contemplated for use with modeling diseases affecting NMJ's, e.g. Amyotrophic lateral sclerosis (ALS).

In one embodiment, the present invention contemplates a NMJ-on-chip where at least one population of cells is derived from a patient diagnosed with a disorder of the nervous system. While it is not intended that the present invention be limited to a particular CNS disorder, in one embodiment, the disorder is ALS. Amyotrophic lateral sclerosis (ALS) is a severe neurodegenerative condition characterized by loss of motor neurons in the brain and spinal cord. In one embodiment, the present invention contemplates generating induced pluripotent stem cells (iPSCs) from patients with ALS and differentiating them into motor neurons progenitors nd/or skeletal cell progenitors for seeding on a microfluidic device. Patients with ALS have progressive deterioration of the neurons, alterations of skeletal muscle fibres are observed in patients with ALS, including but not limited to accumulation of abnormal protein inclusions, mitochondrial changes, skeletal muscle atrophy, etc.. There are currently no effective treatments for ALS. In one embodiment, the present invention contemplates the NMJ-on-chip as a model system for testing drugs so as to predict success in subsequent clinical trials.

In other embodiments, diseases where skeletal muscle abnormalities are found include multiple system atrophy.

It is contemplated that iPSC technology can be used together with microfluidic chips to mimic patient-specific phenotypes in disease states. Thus, in one embodiment, iMNs are derived from a patient diagnosed with or at risk for a disease. In one embodiment, ihSKMCs are derived from a patient diagnosed with or at risk for a disease. In yet another embodiment, the iMNs and ihSKMCs are generated from the same patient line, e.g. the same patient stem cells. In one embodiment, the patient has symptoms of a CNS disorder, and more specifically, a neurodegenerative disease. In one embodiment, the neurodegenerative disease is ALS.

More specifically, the embodiments described herein show that functional NMJ-on-Chip, i.e. NMJ-on-chip (diMNs/hSKMCs) with reduced spontaneous muscle contractions, are superior over co-cultures (2D) of MN and muscle cells. Further, hSKMCs (human skeletal muscle cells) grown on microfluidic chips as described herein, i.e. SkMCs-on-chip, are superior over plate cultures of muscle cells.

In particular, NMJ-on-Chip, in one embodiment, includes a motor neuron-on-chip, e.g. patient iPSC-derived MNs, expressing neuronal markers, are combined with a human skeletal muscle-on-chip: containing contractile tissue. Although co-culture of muscle and neuronal cells on a tall channel microfluidic chip was successful, it was determined that to provide a more robust and functional NMJ-on-chip there was an apparent need to inhibit spontaneous muscle fiber contractions induced by co-culture with MNs. In part, because by adding medium, or blockers to the culture medium, for reducing generation of an action potential (AP) in the NMJ, there was a lower loss of myotubes over time. In other words, human skeletal cells co-cultured with human MNs showed spontaneous muscle fiber contractions resulting in a loss of myotube structure beginning within 24-48 hours. By switching to a medium that reduces spontaneous contractions the myotubes remain viable longer over time. Further, reduction of spontaneous contractions allows the controlled addition of pharmacology agents on older co-cultures. In contrast, in cultures of muscle cells without neurons there was little spontaneous twitching, i.e. contractions, and these cultures remained viable over longer time periods.

In summary, a Human Muscle Cell Culture in-Chip was first developed in a single channel (Quad) chips. HSkMCs were seeded into an upper channel at 2 different cell densities; differentiation was induced then muscle cells were screened for myo-fiber contraction. It was observed that human skeletal myoblast (hSkMCs) differentiate into polynucleated myofibers (d5) with spontaneous myofiber contractions (d10). Secondly, hSkMCs were seeded into the lower channel of a 2-channel microfluidic chip, including a tall chip.

A NMJ-on-chip was provided by combining the 2 chips, i.e. human iPS-derived MN and skeletal muscle cell-on-chip. hSkMCs were seeded into the lower channel of a tall channel chip, then diMNs (day 12) were added to the upper channel. Medium optimization was done in order to reduce spontaneous contractions in chips with diMNs & hSkMCs.

Thus, exemplary steps for providing a functional NMJ-on-Chip by combining motor-neurons on a chip (upper blue channel) with skeletal muscle cells on a chip (lower-red) channel include: Seeding the bottom (lower-blue) channel as a skeletal muscle-on-chip capable of producing contractile muscle tissue expressing markers myosin heavy chain (MHC) (green), pre-BTX (α-bungarotoxin) (red) identified by immunohistochemistry and stained for DNA (blue) shown by fluorescent microscopy. Seeding the upper channel of the microfluidic chip with patient iPSC-derived MNs that under chip culture conditions will express neuronal expressing markers Neuron-specific Class III β-tubulin (TuJ1) (red), selectivity/selective factor 1 complex (for RNA polymerase) (SL1) (blue), homeobox B9 (HOXB9) (red), identified by immunohistochemistry (IHC) as shown by fluorescent microscopy. In some embodiments, spontaneous contractions may be stopped by adding calcium channel blockers or sodium channel blockers to the culture media.

Several embodiments for experiments were provided, along with exemplary results. For examples, Experiment (Exp) 1 showed that hSkMC seeding density at $3 \times 10^6$ cells/ml, but loss of cells 24 h after contracting activity. Experiment 2 showed that Sulfo-SANPAH cross-linked ECM provides more stability to hSkMCs. Experiment 3 showed improved hSkMCs in-chip integrity. However, this was lost 48 h after contraction activity. Experiment 4 showed that hSkMC integrity in chip is expandable over time (in monoculture). Experiment 5 showed that pharmacology and imaging was possible for measuring functional NMJ interactions. Thus, in some embodiments, pharmacological testing of agents for treating diseases, such as ALS NMJs, is contemplated. Including using cells derived from ALS patients.

Additionally, contemplative embodiments include, but are not limited to increasing cell in-chip longevity; anchoring hSkMCs; further reducing spontaneous activity of neurons and/or NMJs; changing cell separation, for example, increasing and/or decreasing pore size of the membrane.

I. The Neuromuscular Junction.

The Neuromuscular Junction (NMJ) refers to the interface between spinal motor neurons and skeletal muscle cells. As each myelinated motor axon reaches its target muscle, it may divide into 20-100 unmyelinated terminal fibers where each terminal fiber innervates a single muscle fiber. The combination of the terminal fibers from a motor axon and the muscle fibers they serve is called a motor unit. The terminal fibers contain both potassium (K+) and sodium (Na+) channels, which control the duration and amplitude of the action potential. In contrast, the nerve terminals, i.e. multiple synaptic end bulbs of each terminal fiber, have a paucity of Na+ channels and the action potential continues passively into this area. The nerve terminal contains synaptic vesicles (SVs), each of which contains approximately 5000-10,000 molecules of the neurotransmitter acetylcholine (ACh).

The mature NMJ can be divided into presynaptic, synaptic, and postsynaptic phases. The following sections describe components and function of NMJs for reference.

A. In Vivo Components of the NMJ.

FIG. 1A: shows a schematic illustration of the exterior of neuromuscular junctions where the yellow axon of a motor nerve at the motor junction has non-myelinated terminal nerve branches forming neuromuscular junctions (one example of an NMJ is outlined by a square). The neuronal terminal nerve branches have synaptic end bulbs (see FIG. 1B) located opposite of a muscular fiber end plate (see FIG. 1B). FIG. 1A also shows a schematic of an interior view of a muscle fiber composed of numerous myo-fibers interspersed with mitochondria (blue), sarcoplasmic reticulum (yellow tubes) within the sarcoplasm of a muscle fiber cell (myocyte).

B. In Vivo Neuronal Induction of an Action Potential (AP).

FIG. 1B: shows a cut-out schematic illustration of the interface between spinal motor neurons and skeletal muscle cells, e.g., a NMJ, for demonstrating the steps of normal motor neuronal activation of muscle fibers. Step 1) An action potential of a myelinated axon reaches the non-myelinated axon terminal branch. Step 2) Voltage-dependent calcium gates open allow Ca++ to enter the end bulb which in Step 3) induces the movement of neurotransmitter containing vesicles to merge with the cell membrane at the end of the synaptic bulb opposite muscle cell acetylcholine (ACh) receptors located in the motor end plates. Neurotransmitter vesicles containing acetylcholine (ACh) are emptied (by exocytosis) into the synaptic cleft. Step 4) Freed ACh from the vesicles then diffuses across the cleft to bind to post-synaptic receptors on the sarcolemma of the muscle fiber in the motor end plate area. Step 5) This ACh binding causes ion channel pumps to open which allows sodium ions to flow across the membrane into the muscle cell while fewer K+ ions are transported out of the cell i.e. (3) Na+ ions enter the cell cytoplasm while (2) K+ ions are transported out, thus triggering a post synaptic action potential (end plate potential) in the NMJ, i.e. the end plate of the muscle sarcolemma. Step 6) the postsynaptic action potential (AP) generated at the end plate, Step 7) AP wave, i.e., sarcolemma membrane depolarization, travels across the muscle cell membrane.

Not shown in FIG. 1, neuron-neuron activations occur when 1N) The axon action potential across an axon reaches the axon terminal. Step 2N) Voltage-dependent calcium gates in the synaptic end bulb open allowing Ca++ to enter the terminal branch which induces the movement of neurotransmitter containing vesicles to merge with the cell membrane at the end of the synaptic bulb opposite the dendrites of an adjacent neuron. Step 3N) Neurotransmitter vesicles containing acetylcholine (ACh) are emptied (by exocytosis) into the synaptic cleft, i.e. the fluidic space in between the cells. Step 4N) Freed ACh from the vesicles then diffuses across the cleft to bind to postsynaptic receptors on the dendrites. Step 5N) This ACh binding causes ion channel pumps to open which allows sodium ions to flow across the membrane into the neuronal cell while fewer K+ ions are transported out of the cell, thus triggering a postsynaptic action potential in the dendrites of the receiving neuron which travels to across the cell membrane to the opposite axon terminal end for triggering an AP in the next cell, starting a Step N1.

C. In Vivo Neuronal Induction of Skeletal Muscle Contraction as a Myofiber (Myotube) Contraction.

FIG. 1C: shows a schematic illustration of a muscle cell (myocyte) depicting how the postsynaptic action potential (AP), triggered by the NMJ, in the sarcolemma of the motor end plate, in Step 6) travels to nearby areas of the T-tubules (i.e. a wave of ion pump activation that travels along the membrane whereby (3) Na+ ions enter the cell cytoplasm while (2) K+ ions are transported out of the cell cytoplasm. Further in Step 7) When the AP reaches areas of the T-tubule portion of the sarcolemma, destabilizing this area of the membrane, the AP in the sarcolemma of the T-tubule area causes the T-tubule to induce the release of Ca++ from the sarcoplasmic reticulum. Step 8) The destabilized sarcolemma then triggers a wave of Ca++ release across the sarcoplasmic reticulum membrane inside of the myocyte. Step 9) The rise in intracellular Ca++ activates contraction of myofibrils, i.e. myosin-actin interactions.

After Ach activates the ion pump, it diffuses away to be broken down by endogenous Acetylcholinesterase (ACHE), i.e. inactivates Ach.

D. Plate Co-Cultures of Motor Neurons with Skeletal Muscle Cells.

Attempts were made to provide NMJs by co-culturing Motor Neurons (diMN) with human Skeletal Muscle Cells (hSKMCs) in 2 dimensional (2D) plate cultures. Individual cultures of muscle cells showed formation of some multi-nucleated myotubes (see, FIG. 2A and FIG. 2B), and co-cultures of hSKMCs with diMNs resulted in an occasional potential NMJ where the neurons grew on top of the myotubes. However, the majority of cells appeared unhealthy and possibly dying (see, FIG. 2C and FIG. 2D). These micrographs of static co-cultures were taken on day 37.

FIG. 2: shows 2-Dimensional (2D) motor neurons (MN) and muscle cell co-cultures grown in static plates, on day 37 of culture.

FIG. 2A: shows a micrograph of healthy human muscle skeletal cells (hSKMCs);

FIG. 2B: shows a higher magnification of cells in FIG. 2A, where the green arrow points to one exemplary multi-nucleated myotube;

FIG. 2C: shows a micrograph of a co-culture of direct induced motor neurons (diMNs) on top of hSKMCs where white arrows point to rounded cell bodies, a green arrow points to an exemplary myotube and a red arrow points to an exemplary neuron on top of said myotube; and FIG. 2D: shows a higher magnification of cells in FIG. 2C where the red arrow points to neuronal branches on top of a myotube identified by a green arrow. White boxes outline the areas shown in higher magnification.

Therefore, there is a need for providing more viable co-cultures of MN and hSKMCs for providing numerous functional NMJs.

II. Generation of Motor Neurons for Providing Embodiments of a NMJ-On-Chip.

A. Neuronal Cells.

In this example, several exemplary embodiments are provided for the generation of motor neurons is provided using iPSCs as the starting material, see, FIGS. 33 and 34 for exemplary concentrations and timelines. In one embodiment, a MN-on-chip is provided with MNs seeded into the upper channel of a microfluidic chip. In another embodiment, MNs are seeded into the upper channel of a NMJ-On-Chip.

Cells are prepared either directly from cultured iPSCs or from frozen lots of pre-differentiated cells. Cells are thawed (or dissociated fresh) and seeded into the chip at day 12 (in the case of iMN differentiation) and at various points in neural differentiation. See, FIGS. 33 and 34 for one embodiment for preparing iMN cells.

As another embodiment, iPSC-derived forebrain neural progenitor cultures (dubbed EZs) were cultured in chip either dissociated or as neural spheres that attached and extended in 3 dimensions.

More specifically, MNs, for example, cells are seeded into microfluidic chips at day 12 of differentiation either from freshly differentiated cultures or directly from a thawed vial.

Conditions were tested for seeding neural (EZ spheres and iMNPs) from frozen stocks of cells on surfaces treated with different extracellular matrices (ECMs). While frozen stocks of cells can be used (particular for the neural cells), it was found that better results can be obtained when fresh cells are used for seeding chips.

As another embodiment, Schwann cells, as precursors or mature cells, may be added to provide a mylin sheath for MNs. In some embodiments, Schwann cells are derived from patient cells, such as patients having a neuromuscular disease.

Culture of these cells in a microfluidic device, such as a microfluidic chip with flow as herein described, whether alone or in combination with other cells, drives maturation and/or differentiation further than existing systems. For example, a mature electrophysiology of the neurons includes negative sodium channel current, positive potassium channel current, and/or action potential spikes of amplitude, duration and frequency similar to neurons in a physiological environment or when compared to static culture neurons, static culture neurons lack one or more of the aforementioned features.

Observed characteristics of the in vitro "NMJ-on-chip" of the present invention include: (1) neuronal networks including motor neurons; (2) optional cell-to-cell communication between neurons exemplified by contact of the neuronal dendrites with neuronal terminal bulbs; (3) optional extended neurite projections exemplified by contact of the neuronal terminal bulbs with muscle cells (e.g. terminal bulb contact by partial transmigration of the membrane separating these cells); (4) optional fluid flow that influences cell differentiation and neuronal muscular junction formation; and (5) high electrical resistance representing the maturity and integrity of the NMJ components.

With respect to skeletal muscle cells, in one embodiment, the present invention contemplates hSkMCs which form a lumen on the chip (for example, completely lining the bottom, sides and top of a flow channel, at least for a portion of its length). Among other advantage (e.g. hSkMCs layer stability) this potentially enables the use of the device with blood or blood components. With respect to selective permeability, the present invention contemplates, in one embodiment, introducing substances in a channel with the hSkMCs such that at least one substance passes through the membrane (e.g. hSkMCs on the bottom side of the membrane) and into a channel above the membrane, and detecting said at least one substance (e.g. with antibodies, mass spec, etc.).

Although there is a strong need for a model of the human neuronal muscular junction, it is also desirable to develop models of NMJs of other organisms (not limited to animals). Of particular interest are models of, for example, mouse, rat, dog, and monkey, as those are typically used in drug development. Accordingly, the neuronal muscular junction: NMJ-on-chip can make advantage of not only human-derived cells but also cells from other organisms. Moreover, although it is preferable that all cell types used originate from the same species (for example, in order to ensure that cell-cell communication is effective), it may be desirable at time to mix species (for example, if a desired cell type is scarce or possess technical challenges).

B. Optional Neuropatterns.

With respect to neurite projections, in one embodiment, the present invention contemplates seeding on nanopatterned surfaces which promote extended and direct (e.g. along a relatively linear path) neurite growth. The preferred nanopattern is linear valleys and ridges, but alternatives such as circular, curved, or any other desired shape or combination thereof are al so contemplated.

Figure 3B:
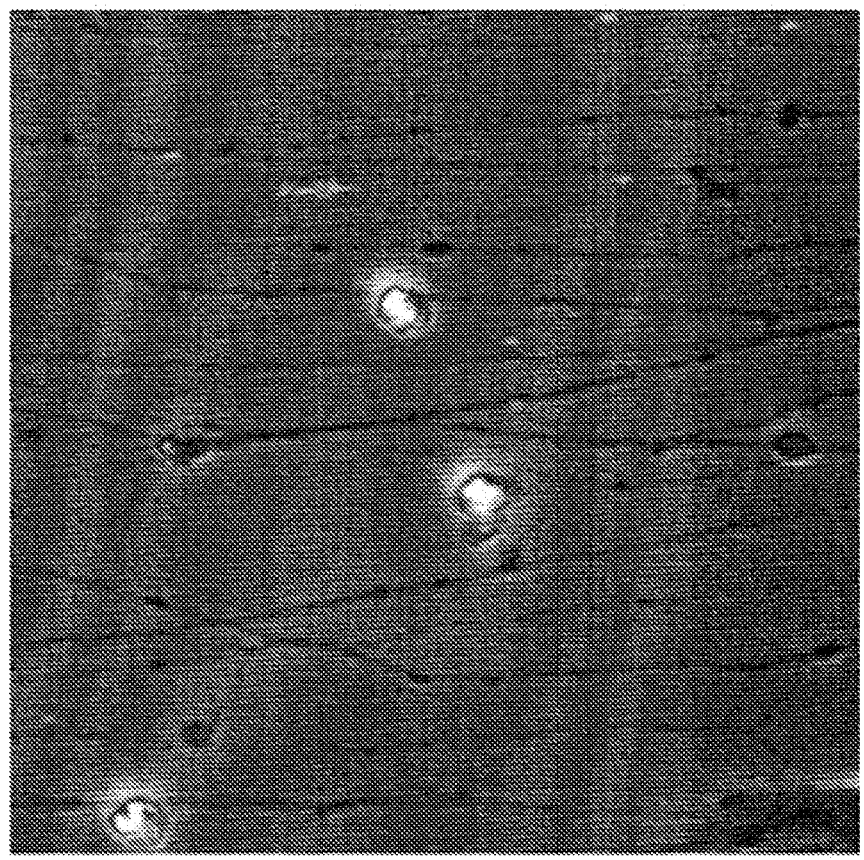
FIG. 3B: shows a duplicate sample of cells (as in FIG. 3A) that were seeded on a nanopatterned surface, resulting in directed neurite growth.
Figure 3A:
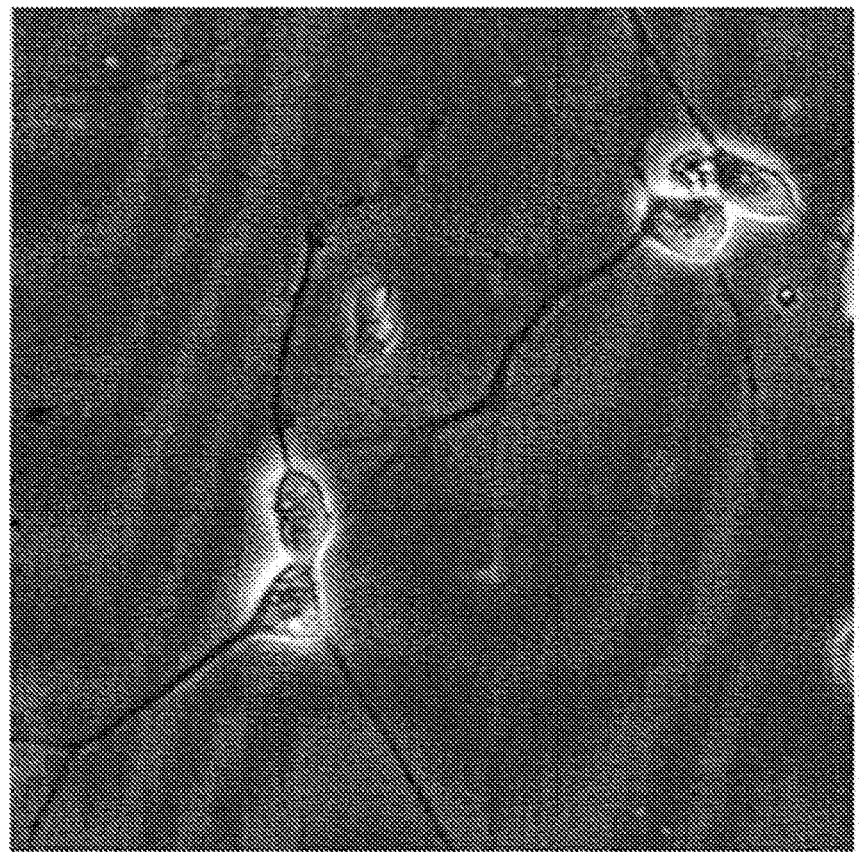
FIG. 3A: shows iMNs seeded on a plain (un-patterned) surface.

Thus, the present invention contemplates, in one embodiment, utilizing nanopatterned surfaces for seeding cells. FIG. 3 shows a first image (FIG. 3A) where iMNPs were seeded on a plain (un-patterned) surface, as well as a second image (FIG. 3B) where the same cells were seeded on a nanopatterned surface, resulting in directed neurite growth. The nanopatterned surface results in directed neurite growth (e.g. in a line pattern). FIG. 3: shows exemplary phase contrast images for embodiments of neuronal growth. FIG. 3A: shows iMNs seeded on a plain (un-patterned) surface; and FIG. 3B: shows a duplicate sample of cells (as in FIG. 3 A) that were seeded on a nanopatterned surface, resulting in directed neurite growth.

Such nanopatterning can be applied to the membrane or any surface of the NMJ-on-chip. In particular embodiments, the nanopatterning is applied to the top surface of the membrane to direct neurite growth for neuron seeded on said surface. It is desired in some uses to direct neurite growth, for example, in studying neuron biology or disease (e.g. conditions that disturb neurite growth or its directionality), as a readout of neuron or NMJ health (e.g. by monitoring neurite growth or its directionality) or in facilitating measurements (e.g. using calcium imaging, IHC or number and/or quality of NMJs, or using a multi-electrode array or patch clamping). The preferred nanopattern is linear valleys and ridges, but alternatives such as circular, curved, or any other desired shape or combination thereof are also contemplated. Linear nanopatterning can include, for example, line spacing ranging from 10 nm to 1 um, 0.5 um to 10 um or 5 um to 50 um, and line depth ranging from 10 nm to 100 nm, 50 nm to 1000 nm, 200 nm to 5 um or 2 um to 50 um.

C. Calcium Flux—High Content Imaging.

Calcium (Ca) imaging or imaging using voltage-sensitive dyes or proteins offer similar advantages to electrophysiological readouts but offers the advantage that no electrodes are necessary.

Ca imaging may occur in the presence of calcium or voltage-sensitive dyes or proteins, to allow the potential recording and optional manipulation of neuronal excitations. These measurements can be used, for example, to provide an indication of neuronal maturation or as a readout of neuron health. Accordingly, some aspects of the present invention include methods of measuring spontaneous, or induced by adding an agent, neuronal excitation.

In turn, neuronal maturation or health can be used as indicators of NMJ-on-chip quality (for example, before starting an experiment) or as an experimental endpoint indicating, for example, that an agent has affected creation of APs, a disease condition has emerged, the NMJ has been modified or compromised, or conversely, that the NMJ or neural function or health have improved. This type of imaging allows observations of neuronal function in the microfluidic chips in real-time. Thus, in one embodiment, neuronal excitation in NMJ-on-chip induced muscle contractions. In one embodiment, addition of tetrodotoxin (TTX), which is a potent blocker of voltage-gated calcium channels, ablates this activity.

In some embodiments, a photograph showing Ca++ hot spots and changes in Ca++ concentrations is a single fluorescent image from a movie of such images. For one example, a movie includes z-stacks from confocal microscopy images.

High content imaging refers to imaging fixed or live cells within a chip. In some embodiments, Ca flux assays on neurons are imaged within the cultures growing in chips.

D. Spontaneous Calcium Bursts in MN Networks in-Chip.

Negative sodium channel currents ($Na^+$) and positive potassium channel ($K^+$) are necessary for normal neuron function and become more pronounced as a neuron matures. In fact, highly complex and repetitive bursts of neuronal activity are indicative of neuronal networks being established in the chip. When induced to fire by injecting current into the neuron at day 6 in chip, more resolved action potentials are observed in these chips as compared to traditional neuronal cultures.

In a controlled study, live cell imaging was performed on diMNs that had been cultured in the chip (MN-on-Chip) (FIGS. 22BB-22J). High content imaging of neuron calcium flux was recorded and plotted with respect to time (FIG. 22K). Calcium flux events or peaks correspond to neural activity and were counted by both automated software and blinded human technician. Each event was assigned a time-stamped value and depicted for each tracked neuron with respect to time. This Calcium (Ca++) flux live cell assay showed Ca flux in relation to spontaneous neuronal activity, i.e. firing. For examples, see FIG. 22.

FIG. 22: shows an exemplary method of growing motor neurons in a microfluidic chip where the MN cells of neural networks have spontaneous calcium bursts.

FIG. 22AA: shows a microfluidic chip seeded with MNs at day 12 of culture.

FIG. 22BB: shows an exemplary timeline where MN precursor cells from Day 12 cultures are seeded at Day 0 in the microfluidic chip, MN network formation is observed a Day 10 on the chip (Day 18 overall from the start of the original MN culture).

FIG. 22CC: shows exemplary images produced by high content life imaging of cells in chips showing Ca++ imaging of diMN cells on Day 12 after seeding onto the microfluidic chip; at high magnification (20×). diMNs show repetitive calcium bursts as visualized via Flou4 labeling in color within the cellular areas, e.g. cell bodies, axons and terminal bulbs, in neuronal networks, where the concentrations of Ca++ are shown by yellow-lower levels, red-higher than yellow areas and highest levels in white areas within the red areas, as shown in the neuron cell bodies.

FIG. 22A: shows exemplary Ca++ imaging of FIG. 22CC in black and white, where the highest amounts of Ca++ are white areas in black and white micrographs, white arrowheads point to cellular areas with concentrated Ca++.

FIG. 22B: shows a higher magnification of a cell in the center of the micrograph in FIG. 22CC/FIG. 22A with two white arrowhead markers used to identify the same area through the different planes of focus.

FIGS. 22D-22J: shows exemplary Ca++ imaging in color from confocal high content micrograph z-stack layers through the cell (shown in FIG. 22B) where higher concentrations of Ca++ are shown by yellow/red/white areas in the neuronal cytoplasm, which discharge and recharge then discharge over time. White arrowheads mark the same location of the cell shown in FIG. 22B-FIG. 22J.

FIG. 22K: shows a graph of average intensity of Ca++ vs. elapsed time (seconds).

III. Generation of hSkMCs for Providing Embodiments of a NMJ-On-Chip.

In this example, several exemplary embodiments are provided for the generation of hSKMCs using iPSCs as the starting material. In one embodiment, a hSkMC-on-chip is provided where hSKMCs may be seeded on the upper or the lower channel of the chip. In some embodiments, hSKMCs are seeded and used in quadruple (Quad) single channel chips.

In some embodiments, myoblasts are derived from patient samples for seeding chips. In some embodiments, iPS cells derived from patient cells are used for seeding chips.

As another example, in one embodiment, induced skeletal muscle progenitor cells are derived from induced pluripotent stem cells, but they are not fully differentiated. In one embodiment, induced skeletal muscle progenitor cells are differentiated on-chip to generate multinucleated myotubes, and ultimately mature striated skeletal muscle myotubes.

Thus, in one embodiment, the present invention contemplates a method of culturing cells, including: a) providing a microfluidic device (optionally including a membrane, said membrane including a top surface and a bottom surface); b) seeding induced skeletal muscle progenitor cells (on said bottom surface so as to create seeded cells); c) exposing said seeded cells to a flow of culture media for a period of time (days to weeks to months) under conditions such that said at least a portion of said progenitor cells differentiate into multinucleated myotubes (and preferably wherein said hSKMCs display a mature phenotype based on testing described herein or staining).

A. Human Skeletal Muscle Cells.

Muscle tissue develops from specialized mesodermal cells called myoblasts. Several myoblasts fuse together to form a myotube. Myotubes are immature multinucleated muscle fibers. Myotubes mature into striated skeletal muscle fibers. Satellite cells are found along the outside of the fibers in vivo. Satellite cells refer to precursors to skeletal muscle cells, able to give rise to satellite cells or differentiated skeletal muscle cells. They have the potential to provide additional myonuclei to their parent muscle fiber, or return to a quiescent state.

The following describes exemplary methods, e.g. for differentiating iPSCs, providing a Muscle Cell Culture-on-Chip.

1. Skeletal Muscle Differentiation from Human iPSCS.

The starting density of cells affects the success of skeletal muscle cell differentiation. The starting iPSc density described herein is exemplary for the cell lines described herein. However, each iPSC line is different so the optimal density should be determined according to each individual cell line's growth (e.g. doubling) rate. For cell lines shown herein, an exemplary recommended cell density and volume of media: 12 or 24 wells 15,000-18000 cells/cm$^2$ and for 96 wells 5000 cells/cm$^2$. One embodiment for a method providing human induced pluripotent stem cells (iPSCs) for use in providing induced hSKMCs is described as follows.

Coat plates with ECM, e.g. Matrigel. Add appropriate volume, see e.g. below, in a sterile tissue culture hood. For a 6 well plate—1 mL/well; 24 well plate—250 μL/well; and 96 well plate—50 μL/well. Leave Matrigel in wells for at least 1 hr at room temperature for coating surfaces. Coating may also be done for more than an hour.

For deriving human iPSC (hiPSC) skeletal cell cultures from hiPSCs: Grow and expand iPSC cultures on Matrigel coated surfaces with mTeSR Media supplemented with Rock Inhibitor (Y-27632) (such as from Sigma-Aldrich, St. Louis, Mo. 63103-USA), at exemplary concentrations from 2.0 uM, 2.5 uM, 5 uM. 10 uM, up to 20 uM, for one day. Nonlimiting examples of mTeSR Media include, cGMP mTeSR™1, mTeSR™1, TeSR™2, TeSR™-E7™, TeSR™-E5, TeSR™-E6, ReproTeSR™, mTeSR™3D, etc., defined, serum-free media for culture of human ES, iPS, pluripotent stem cells, and the like). Clean iPSCs cells daily by removing differentiated cells to maintain a spontaneous differentiation free culture for optimal skeletal muscle differentiation. In one embodiment, 3 wells of a 96 well plate containing iPSCs, maintained at 70-80% confluence is suggested for use to start differentiation.

More specifically, Stage 1 skeletal muscle induction: Step 1. Dissociate iPSCs with Accutase (e.g. of a cell detachment solution) for 5 min.; Step 2. Resuspend cells in phosphate buffered saline (PBS) in a 15 mL conical tube; Step 3. Centrifuge the cells for 5 min (minutes) at 1000 RPM (revolutions per minute) for spinning cells gently to the bottom of the tube; Step 4. Aspirate media without disturbing the cell pellet in the bottom of the tube, then resuspend cells in skeletal muscle induction media 1, DMEM/F12, (see, Table 1); Step 5. Count the number of live cells (in part by exclusion staining the dead cells), e.g. using an automated cell counter: Take out 10 ul of cell suspension from the tube, mix with 10 ul of dye (1:1), e.g. in Trypan blue dye for staining dead cells, mix well, load mixture in cell counter chamber to count; Determine live cell numbers per ml, then Step 6. Plate single cells with appropriate number of cells, as suggested herein, on a Matrigel coated plate in mTeSR Media supplemented with Rock Inhibitor (Y-27632), see exemplary materials and concentrations above, for one day; Step 7. On the next day, switch the Stage 1 media to DMEM/F12 (1:1) supplemented with exemplary concentrations of 3 uM CHIR99021, 05 uM LDN193189; Step 8. Change media every day until day three; then Step 9. On Day three, supplement the existing media with an exemplary concentration of 20 ng/mL bFGF and continue feeding for additional seven days. Media should be change on a daily basis.

TABLE 1

Skeletal Muscle Induction Media 1.

| Stage 1 Media Components | Exemplary Concentration | Exemplary Catalog number | Exemplary Company (Source) |
|---|---|---|---|
| DMEM/F12 (Dulbecco's Modified Eagle Medium/Nutrient Mixture F-12 Ham) | 1:1 | NA (not available) | Sigma-Aldrich, St. Louis, MO 63103-USA |
| CHIR99021 | 3 uM | M60002 | Xcess Biosciences, Inc. (XcessBio), San Diego, CA 92130, USA |
| LDN193189 | 0.5 uM | S2618 | Selleck Chemicals, Houston, TX 77054, USA |
| bFGF (Basic fibroblast growth factor) | 20 ng/mL | NA | Sigma-Aldrich, St. Louis, MO 63103-USA; PeproTech, Rocky Hill, NJ 08553-USA |

Stage 2—Commitment to Myoblasts. 1. After 10 days of incubation (e.g. 7 days incubation in complete skeletal muscle induction media 1), the media is changed to a DMEM/F12 (1:1) supplemented with exemplary concentrations of 10 ng/ml HGF, 2 ng/ml IGF and 0.5 uM LDN193189 (Skeletal Muscle Induction Media 2) for two days of incubation, see Table 2; If cells are too confluent by day 12-14, cells should be dissociated and replated on ECM, e.g. Matrigel coated surfaces at recommended cell densities, mentioned above, for optimal results; and 2. On day 12, cells were cultured with DMEM/F12 (1:1), with exemplary concentrations of 15% KSOR supplemented with with an exemplary concentrations of 2 ng/ml IGF (incomplete Skeletal Muscle Induction Media 3) for up to four days.

TABLE 2

Skeletal Muscle Induction Media 2.

| Stage 2 Media Components | Exemplary Concentration | Exemplary Catalog number | Exemplary Company (Source) |
|---|---|---|---|
| DMEM/F12 | (1:1) | NA (not available) | Sigma-Aldrich, St. Louis, MO 63103-USA |
| CHIR99021 | 3uM | M60002 | Xcess Biosciences, Inc. (XcessBio), San Diego, CA 92130, USA |
| LDN193189 | 0.5uM | S2618 | Selleck Chemicals, Houston, TX 77054, USA |

TABLE 2-continued

Skeletal Muscle Induction Media 2.

| Stage 2 Media Components | Exemplary Concentration | Exemplary Catalog number | Exemplary Company (Source) |
|---|---|---|---|
| bFGF | 20 ng/mL (at least 1, 5, 10, 20, 30, up to 50 ng/ml) | NA | Sigma-Aldrich, St. Louis, MO 63103-USA |
| HGF (hepatocyte growth factor) | 10 ng/mL (at least 2, 4, 5, 10, 20, 30, 60, 100 up to 200 ng/ml) | NA | R&D Systems, Minneapolis, Minnesota, USA |
| IGF (insulin-like growth factor) | 2 ng/mL (at least 1.5, 2, 5, 10, 60, 100 up to 200 ng/ml) | NA | PeproTech, Rocky Hill, NJ 08553-USA |

Stage 3 Maturation: For differentiation of myoblasts into myotubes and for maintenance of Skeletal muscles: 1. On Day 12, 13 or 14, media was changed to DMEM/F12 (1:1), with exemplary concentrations of 15% KSOR supplemented with 10 ng/mL HGF and 10 ng/mL IGF-1 (complete Skeletal Muscle Induction Media 3); 2. Change Media every other Day until used, up to day 40; and 3. Optional: Fix cell samples, up to day 40 (or day used), e.g. of fixative, 4% PFA (Paraformaldehyde) to stain for skeletal muscle markers, e.g. as described herein. Other fixatives may be used for immunostaining.

TABLE 3

Skeletal Muscle Induction Media 3.

| Stage 3 Media Components | Exemplary Concentration | Exemplary Catalog number | Exemplary Company (Source) |
|---|---|---|---|
| DMEM/F12 | (1:1) | NA (not available) | Sigma-Aldrich, St. Louis, MO 63103-USA |
| KOSR (Knockout Serum Replacement) | 15% | KnockOut ™ SR 10828028 | Gibco ™ KnockOut ™ Serum Replacement |
| HGF | 10 ng/mL (at least 2, 4, 5, 10, 20, 30, 60, 100 up to 200 ng/ml) | NA | R&D Systems, Minneapolis, Minnesota, USA |
| IGF-1 (insulin-like growth factor 1) | 10 ng/mL (at least 1.5, 2, 5, 10, 60, 100 up to 200 ng/ml) | NA | PeproTech, Rocky Hill, NJ 08553-USA |

The exemplary protocol described here for differentiating hSKMCs was used on ECM coated substrates, such as plates and microfluidic channels. For examples of ECM, plates and channels were coated with Matrigel, while microfluidic channels were coated with Laminin (non-cross-linked) and cross-Linked Laminin, as described herein. Seeding densities for the chips were used as described for the experiments, where either ihSkMCs were differentiated as described here, as one example, starting myotube differentiation on D1 in Stage 1 Skeletal Muscle Induction Media (incomplete).

B. Extracellular Matrix (ECM) Cross-Linking Effects on Myotube Structure and Stability in Chips.

As one embodiment, a single channel chip (e.g. Quad chip: as a 4 single channel chip) was used initially for determining stages of muscle cell maturation on a chip and numbers of seeded cells that provide viable cultures in relation to chips coated with ECM.

In some embodiments, an extracellular matrix (ECM) layer is provided to coat (cover) the entire surface of the lower channel (bottom, sides and top) for growing human skeletal striated muscle cells. In one embodiment, Laminin was used as an exemplary ECM component for coating the surface. In another embodiment, a cross-linker chemical was used for cross-linking Laminin molecules. As an exemplary cross-linker chemical, Sulfo-SANPAH was used. Experiment 2: showed that Sulfo-SANPAH cross linked ECM provides more stability to hSKMCs. Sulfo-SANPAH cross-linked ECM enables formation of almost 2-fold more MHC positive multinucleated fibers. Further, more nuclei per myo-tubes with cross-linked ECM. In fact, a 3-fold higher number of nuclei in MHC myo-fibers seeded on Sulfo-SANPAH cross-linked ECM-Laminin was observed over Laminin alone.

1. Human Skeletal Muscle Cells: Extracellular Matrix.

a. Extracellular Matrix (ECM).

In some embodiments, an extracellular matrix (ECM) layer is provided to coat (cover) the entire surface (bottom, sides and top) of the lower channel for growing human skeletal striated muscle cells. In one embodiment, laminin was used as an exemplary ECM component for coating the surface. In another embodiment, a cross-linker chemical was used for cross-linking laminin molecules. As an exemplary cross-linker chemical, Sulfo-SANPAH was used.

Sulfo-SANPAH cross-linked ECM enables formation of almost 2-fold more MHC positive multinucleated fibers. Further, more nuclei per myo-tubes with cross-linked ECM. In fact, a 3-fold higher number of nuclei in MHC myo-fibers seeded on Sulfo-SANPAH cross-linked ECM-laminin was observed over laminin alone.

FIG. 4: Shows one embodiment of a human skeletal muscle cell culture hSkMC-In-Chip: Extracellular Matrix (ECM) use for hSkMCs-In-Chip. In one embodiment, the chip is a Quad chip.

Figure 4A:
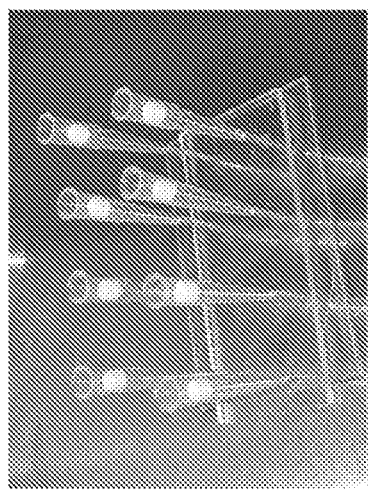
FIG. 4A: shows a picture of a single channel (Quad) Chip with pipette tips used to block channels for coating the inside surfaces with an ECM layer then seeded with human skeletal muscle cells (hSKMCs).

FIG. 4A: shows a picture of a single channel (Quad) Chip with pipette tips used to block channels for coating the inside surfaces with an ECM layer then seeded with human skeletal muscle cells (hSKMCs).

Figure 4C:
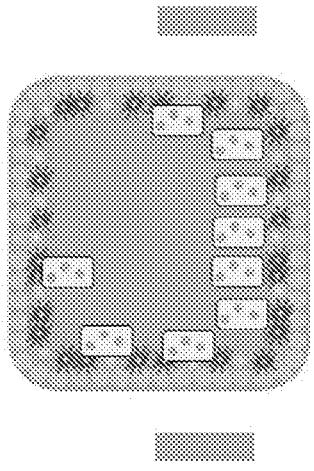
FIG. 4C: shows a schematic illustration of a cross-sectional view of the quad channel with ECM as Laminine (purple and blue stars) with hSkMCs as blue spotted yellow blocks and a representative cross linking of ECM as yellow stars, e.g. with Sulfo-SANPAH.
Figure 4B:
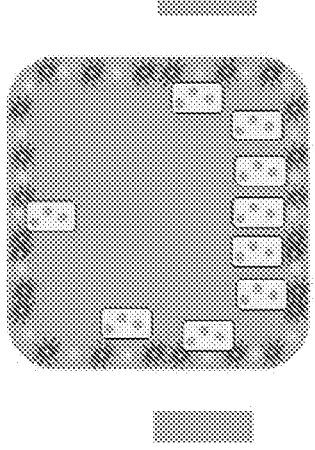
FIG. 4B: shows a schematic illustration of a cross-sectional view of the quad channel with ECM as Laminine (purple and blue stars) with hSkMCs as blue spotted yellow blocks.

FIG. 4B: shows a schematic illustration of a cross-sectional view of the quad channel with ECM as Laminine (purple and blue stars) with hSkMCs as yellow-spotted blocks.

FIG. 4C: shows a schematic illustration of a cross-sectional view of the quad channel with ECM as Laminine (purple and blue stars) with hSkMCs as yellow-spotted blocks and a representative cross linking of ECM as yellow stars, e.g. with Sulfo-SANPAH.

b. Extracellular Matrix (ECM) Cross-Linking Effects on Myotube Structure and Stability in Chips.

This example shows one embodiment of a set up and time course for culturing Human Muscle Cells in-Chip: providing non-contracting myotubes on ECM coated chips. As one embodiment, a single channel chip (e.g. Quad chip: as a 4 single channel chip) was used initially for determining stages of muscle cell maturation on a chip, effects of ECM, and numbers of seeded cells that provide viable cultures in relation to chips coated with ECM. In this embodiment, muscle cells grown without nerve cells present did not show spontaneous contractions of myotubes.

Experiment 1 Showed that hSkMC Seeding Density at $3 \times 10^6$ Cells/Ml, but Loss of Cells 24 h after Contracting Activity As one example, Sulfo-SANPAH cross-linked ECM enables formation of almost 2-fold more MHC positive multinucleated fibers. Further, more nuclei per myo-tubes with cross-linked ECM. In fact, a 3-fold higher number of nuclei in MHC myo-fibers seeded on Sulfo-SANPAH cross-linked ECM-Laminin was observed over a Laminin coating without the use of a cross-linker.

FIG. 5: shows one embodiment of a human muscle cell culture in-chip: Set Up and Time Course for producing multinucleated myofibers that are not contracting.

FIG. 5A: Single channels of Quad Chips were seeded with human skeletal muscle cells (hSKMCs). Group 1 and Group 2: $5 \times 10^6$/ml cells; Group 3 and Group 4: $1.6 \times 10^6$/ml cells. Groups 1 and 3 do not have cross (X)-linked ECM while Groups 2 and 4 have exemplary Sulpho SANPA X-linked ECM.

FIG. 5B: shows a schematic experimental timeline: Seeding cells on Day (D) 0. D1: Inducing differentiation. D5 observing fusion of myoblast cells. D10: Screening for myo-fiber contraction in cultures that were not stained for analysis; observing polynucleated fibers but no myofiber contractions. D14 Fixing cells and fusion-index-analysis.

FIG. 5C: Day 14: Fixation and fusion-index-analysis based upon staining for myosin heavy chain (MHC) (red) and nuclei (DNA) (shown in blue).

FIG. 5D: Shows a schematic illustration of multinucleated myofibers in WIC (red) and nuclei (DNA) (blue).

FIG. 6: shows Human Skeletal Myoblast-Derived Poly-Nucleated Fibers growing in microfluidic chips where Sulfo-SANPAH cross-linked ECM enables formation of almost 2-fold more MHC positive multinucleated fibers.

FIG. 6A-6D: show fluorescent micrographs of immunostained myosin heavy chain (MEW) (red) myo-fibers and DAPI stained nuclei (DNA) (shown in blue) comparing cultures started at the 2 different densities (FIGS. 6A-B: $5 \times 10^6$/ml cells and FIGS. 6C-6D: $1.6 \times 10^6$/ml cells) with and without cross-lined (X-link) ECM-Laminin (Lam).

FIGS. 6E-6F: show phase contrast micrographs of Day 14 cells grown on Laminin (Lam) and cross-linked (X-Link) ECM-Laminin (Lam), respectively. More WIC positive multinucleated fibers are observed with X-Linked Laminin after 14 days. White arrows point to 2 exemplary multinucleated myotubes FIG. 6G: shows a graph comparing number MHC+ myo-fibers to the treatments shown in FIGS. 6A-6D where at both cell densities the number of myofibers growing on x-Linked ECM is almost 2-fold more than fibers grown on regular, non-cross-linked, ECM.

FIG. 7: shows Human Skeletal Myoblast-Derived Poly-Nucleated Fibers growing in microfluidic chips comparing non-cross-linked to cross-linked ECM (Laminin) where more nuclei per myo-tubes are observed growing on cross-linked ECM.

FIG. 7A-7D: show fluorescent micrographs of immunostained myosin heavy chain (MHC) (red) myo-fibers and DAPI stained nuclei (DNA) (shown in blue) comparing cultures started at the 2 different densities with inserts showing higher magnifications of presumptive myo-fibers for each treatment.

FIGS. 7A-7B: $5 \times 10^6$/ml cells and FIGS. 6C-D: $1.6 \times 10^6$/ml cells) with Laminin (Lam) and with cross-linked (X-linked) Laminin-ECM.

FIGS. 7E-7F: Show a 3-fold higher number of nuclei in MHC myo-fibers seeded on exemplary Sulfo-SANPAH cross-linked ECM by graphical comparisons.

FIG. 7E: shows a graph comparing DAPI+ nuclei per MHC+ fiber for determining myo-fiber at the 4 treatments shown.

FIG. 7F: shows a graph comparing percentage of total DAPI+ per channel, i.e. percentage of DAPI in myo-fibers at the 4 treatments shown in FIG. 7A-D.

IV. Combining MN-On-Chip with hSkMC-On-Chip for Providing Embodiments of a NMJ-On-Chip.

In one embodiment, the starting material for generating at least one cellular component for the NMJ generated on a microfluidic device (or simply "NMJ-on-chip") includes stem cells (e.g. see the protocols in Examples, and below). In particular embodiments, these stem cells may include, for example, induced pluripotent stem cells (iPS cells) or embryonic stem cells. In one embodiment, progenitor cells (derived from stem cells) related to neural lineages or cells directly reprogrammed into motor neurons, neural lineage progenitors, and the like, are employed/seeded on the chip. In one embodiment, progenitor cells (derived from stem cells) related to skeletal muscle lineages or cells directly reprogrammed into skeletal muscle cells, skeletal muscle multinucleated myotubes, skeletal muscle lineage progenitors, and the like, are employed/seeded on the chip. It is important to note that not all cell types involved in the NMJ-on-chip must be generated from stem cells. For example, the NMJ-on-chip may employ primary skeletal muscle cells. Techniques are known in the art to reprogram, expand and characterize human iPS cells from human skin or blood tissues of healthy subjects and diseased patients. For example, a non-integrating system based on the oriP/EBNA1 (Epstein-Barr nuclear antigen-1) episomal plasmid vector system can be used to avoid potential deleterious effects of random insertion of proviral sequences into the genome. It is preferred that the iPSC lines so generated express the pluripotency markers (SSEA4, TRA-1-81, OCT3/4, SOX2) along with a normal karyotype. In the present invention, iPS cells are used to generate components of the NMJ-on-chip, e.g. neurons, etc. While in many cases, the iPS cells are from normal subjects, it is also contemplated that the iPS cells can be derived from patients exhibiting symptoms of disease. In one embodiment, the NMJ-on-chip is populated with cells derived from iPS cells from a patient diagnosed with a disorder of the nervous system, including but not limited to iPSC-derived motor neurons from Amyotrophic lateral sclerosis (ALS) patients. See D. Sareen et al., "Targeting RNA foci in iPSC-derived motor neurons from ALS patients with C9ORF72 repeat expansion" Sci Transl Med. 2013 Oct. 23; 5(208): 208ra149.

As one example, FIG. 23: shows exemplary fluorescent micrographs of NMJ-On-Chips using iPSC derived Myofibers (iSKMCs) as superimposed (co-localized images) of neurons and myotubes. (Experiment 5).

FIG. 23A: shows a fluorescent micrograph of nerve axons (red) parallel to multinucleated (blue) muscle heavy chains within muscle myofibers (green) showing separation between internal myosin and external nerve fibers. Myosin (MHC: myosin heavy chain) (green), neuronal nerve fibers TuJ1 (red) and DNA (DAPI) (shown in blue)

FIG. 23B: shows a fluorescent micrograph view on end (as compared to the orientation in FIG. 23A) for a different view, i.e. x-z image, of muscle Myogenin (green), nerve TuJ1 (red) and DNA (DAPI) (shown in blue) where nuclei superimposed on the muscle staining shows light blue, see example at the white arrow.

In one embodiment, the present invention contemplates differentiating "stem-cell derived cells" on the chip, i.e. in a microfluidic environment. The term "stem-cell derived cells" refers to cells derived from stem cells that fall on a spectrum of differentiation. For example, in one embodiment, induced motor neuron progenitor cells (including but not limited to, iPSC-derived spinal neural progenitors) are derived from induced pluripotent stem cells, but they are not fully differentiated. In one embodiment, induced motor neuron progenitor cells are differentiated on-chip to generate motor neurons, and ultimately mature motor neurons. Thus, in one embodiment, the present invention contemplates a method of culturing cells, including: a) providing a microfluidic device (optionally including a membrane, said membrane including a top surface and a bottom surface); b) seeding induced motor neuron progenitor cells (optionally on said top surface and optionally skeletal muscle cells on said bottom surface so as to create seeded cells); c) exposing said seeded cells to a flow of culture media for a period of time (days to weeks to months) under conditions such that said at least a portion of said progenitor cells differentiate into motor neurons (and preferably wherein said motor neurons display a mature phenotype based on testing described herein or staining). Further, at least a portion of said progenitor cells differentiate into skeletal muscle cells (and preferably wherein said skeletal muscle cells display a mature phenotype based on testing described herein or staining). In a preferred embodiment, at least a portion of the skeletal muscle cells form multinucleated myotubes. In yet another embodiment, at least a portion of the multinucleated myotubes are striated. In one embodiment, the method (optionally) further includes e) culturing said seeded cells under conditions such that said skeletal muscle cells on said bottom surface form neural muscular junctions.

In some embodiments of a NMJ-on-a-chip, neural cell cultures were seeded into chips following the seeding of hSMCs, described above, either on the same day, 18 hours later, the following day, or up to 9 days after hSMCs had been seeded onto the chip. The chips were cultured for 14 days and fixed and stained for relevant markers. In some embodiments, confocal microscope imaging shows proximity of cells in a z-stack image.

Thus in some embodiments, neural cells in the top channel of the microfluidic device and hSMCs on the bottom channel of the microfluidic device are shown in close proximity.

The attached cells were then tested for markers to confirm their identity, e.g. ICC. ICC overlay data: By overlaying images taken after staining the cells, specific cell identification can be combined with original activity traces (e.g. calcium flux images, etc) to determine specific activities of individual cell types in the chip.

In some figures shown herein, images from a microfluidic chip wherein at least a portion of a MN (i.e. the terminal bulb) has transmigrated the membrane and contacted the hSMCs on the other side. In some examples, MN are shown in red against the green stained hSMCs.

Thus in one embodiment a vertical 2D projection of a 3D confocal stack of images slices is imaged, which allows for visualization of the neurons and hSMCs together, even though they are not in the same imaginary plane on the microfluidic device. hSMCs display a MHC marker, while the neurons are positive for TUJ1, for example. DAPI (4',6-diamidino-2-phenylindole) is used as a fluorescent stain for DNA (deoxyribonucleic acid) in nuclei.

As one example, FIG. 8: shows one embodiment of a Human iPS-Derived MN and Muscle Cell Co-Culture in-a Tall Channel Microfluidic Chip.

FIG. 8A: shows a picture of a tall channel microfluidic chip (16) in one embodiment seeded with MNs at day 12 of culture into the port (2) of the upper (blue) channel (thick arrow) (1) and human skeletal muscle cells into the port (3) of the lower (red) channel (1) at the end of the other channel (thin arrow). The arrowhead points to a vacuum chamber (4), for optional use.

FIG. 8B: shows iPSC-derived MNs seeded into the upper channel forming a neural network stained with TUJ1 (green); Islet1 (ISL1) (blue); indicating early motor neurons, and Islet1 (ISL1) (blue); HoxB9 (red); indicating more mature motor neurons, while the third frame is a superimposed image showing both early and more mature motor neurons.

FIG. 8C: shows skeletal muscle cells seeded into the lower channel stained with myosin heavy chain (MHC) (green) with an insert showing myofibers at a higher magnification; α-bungarotoxin BTX (pre-BTX) (red), for identifying AchR in the motor end plate, with an insert showing stained cells at a higher magnification; and DNA in nuclei stained then fluoresced in the blue range, with an insert showing myofibers (green) at a higher magnification with unstained regions that likely correspond to multinuclear areas in the myofibers; and FIG. 8D: shows a schematic illustration of a vertical cross section of a tall channel microfluidic chip where MNs from a Day 12 culture seeded onto the chip develop cell bodies containing nuclei (purple circles), axons and terminal areas next to the membrane separating the top from the bottom channel containing human skeletal muscle cells growing around the edge of the channel.

V. Medium Optimization to Reduce Spontaneous Contraction Rates in NMJ-On-Chip for Providing a Functional NMJ-On-Chip.

By day 10 of cultures, observations of myotubes showed high rates of spontaneous contractions. In fact, a loss of myotubes starting around 24 hours was observed after start of spontaneous contractions. Therefore, experiments were designed for identifying media that would reduce spontaneous contractions in cultures. It was determined that spontaneous contraction rates of muscle cells should be lowered in order to determine whether spontaneous contractions were effecting longer term viability, and for use in testing potential treatments, including agents, for increasing contraction rates. Therefore, the following embodiments are provided for developing medium for lowering spontaneous contraction rates. Media was tested that included at least one agent for reducing spontaneous myotube contraction rates. In part, rates were artificially reduced in order to allow testing of agents for altering muscle contractions, e.g. increasing muscle contraction rates.

Thus, in some embodiments, a media for lowering contraction rates was developed, e.g. CoM media was developed and used for perfusing NMJ-on-chips. As used herein, "COM" or "coM" or "CoM" or "co-media" refers to a culture media as formulated in FIG. 33, Day 12-xx (see above), which in addition to Iscove's Modified Dulbecco's Media/Ham's F-12 Nutrient Mixture (IMDM/F12), Non-Essential Amino Acids (NEAA), B27 supplement (B27), e.g. Gibco™ B-27 Serum Free Supplement (plus vitamin A), N-2 Supplement (N2), e.g. Gibco™ PSA, Compound E and DAPT, e.g. STEMCELL Technologies Inc., Cambridge, Mass. 02142-USA, all-trans RA, e.g. STEMCELL Technologies Inc., purmorphamine (or SAG), both available, e.g. STEMCELL Technologies Inc., Cambridge, Mass. 02142-USA, db-cAMP, Ascorbic Acid, e.g. STEMCELL Technologies Inc., Cambridge, Mass. 02142-USA, Glial cell-derived neurotrophic factor (GDNF), Promega Corporation, Brain-derived neurotrophic factor (BDNF), e.g. (Sigma-Aldrich), and VPA (valproic acid), e.g. (Sigma-Aldrich), includes 2% FBS serum, as one example of a media for reducing spontaneous skeletal muscle contractions in co-cultures of MNs and hSKMCs. Media components are listed with an example of an exemplary source.

In this example, exemplary embodiments are provided for a Human iPS-Derived MN and Muscle Cell Co-Culture in-Chip for use in testing for variable effecting longer term viability of cells and for using chips in testing pharmacology agents, i.e. for use in treating NMJ related diseases.

Experiment 1: Human iPS-Derived MN and Muscle Cell Co-Culture in-Chip.

Day 0: seeding hSKMCs; Day 1: (18 h later) seeded diMNs (d12); Day 5: observation of formation of myotubes; Day 10: observation of myofiber contraction; Day 11: observation of progressive loss of myofibers; Day 14: fixation and analysis. There was a continuous loss of myo-tubes after day 11-24 hours, after last observation of spontaneous myo-tube contractions. Further, the use of flow during culture increases loss of myo-tubes. See, FIG. 9 for a schematic illustration and numbers of cells in the different replicates for comparing effects of initial seeding densities.

Experiment 1 showed that hSKMC seeding density at $3 \times 10^6$ cells/ml, but loss of cells 24 h after contracting activity.

FIG. 9: Shows one embodiment of a Human iPS-Derived MN and Muscle Cell Co-Culture in-a microfluidic Chip.

FIG. 9A is a picture of an exemplary microfluidic chip where day 12 MNs are seeded into the top (upper-blue) channel and hSkMCs are in the bottom (lower-red) channel;

FIG. 9B shows a schematic illustration of an exemplary cross section of NMJ microfluidic chip with day 12 MNs in the top channel and hSkMCs in the bottom channel with 3 sets of Experimental Chips for comparing cell densities at the time of seeding: Chip 1: top: $3 \times 10^6$/ml diMN cells and bottom: $5 \times 10^6$/ml hSKMC cells; Chip 2: top: $3 \times 10^6$/ml diMN cells and bottom: $10 \times 10^6$/ml hSKMC cells; and Chip 3: top: $3 \times 10^6$/ml diMN cells and bottom: $20 \times 10^6$/ml hSKMC cells.

FIG. 9C: shows a schematic illustration of a timeline showing co-culture of hSkMCs seeded Day (D) 0 with differentiation (diff) initiated on D1, Day 12 MNs seeded D1, Myofiber formation on D5, myofiber contractions observed D10, a loss of myofibers observed on D11, with fixation and analysis by ICC on D14.

A. Experimental System for Testing Media to Reduce Spontaneous Muscle Contraction Rates.

The following experiments were designed for identifying media components that would lower spontaneous contraction rates.

Experiment 3: Testing media components for reducing spontaneous muscle contractions. Top: $3 \times 10^6$ diMNs and Bottom: $20 \times 10^6$ hSkMCs, as tested in 3 different groups of either cells seeded on top, bottom or both, in media harvested from diMNs/hSkMCs cultures or coM.

Experiment 3 showed improved hSkMCs in-chip integrity. However, this was lost 48 h after contraction activity occurred in diMN/hSkMC media.

FIG. 10: shows one embodiment of an experimental system (Experiment 1) as a schematic illustration for testing medium to reduce spontaneous contractions of cells in the microfluidic tall channel chip. Experimental Groups 1-3 directly compare medium harvested from diMNs/hSKMC cultures with coM media in chips containing induced motor neurons (diMNs: Motor-neuron-on Chip) and human Skeletal Muscle Cells (hSkMCs-on-Chip), each cell type growing alone on chips then combined in the same chip in the same media (upper and lower channel) for providing a neuronal-muscular-junction (NMJ-on-Chip).

FIG. 10A: Group 1: shows a schematic illustration of the tall channel chip, with vacuum chambers (4), diMNs in the top channel but no cells in the bottom channel. Group 2: shows a schematic illustration of the tall channel chip with no cells in the top channel but with hSkMCs in the bottom channel. Group 3: shows a schematic illustration of the tall channel chip with diMNs in the top channel and hSkMCs in the bottom channel for providing a NMJ-on-Chip.

FIG. 10B: shows a schematic illustration of cells numbers and media used for growing cells:

Group 1: Top: $3 \times 10^6$ diMNs Bottom: none. Group 2: Top: none. Bottom: $10 \times 10^6$ hSkMCs.

Group 3: Top: $3 \times 10^6$ diMNs. Bottom: $20 \times 10^6$ hSkMCs.

B. Reducing spontaneous Myotube Contractions at Day 10 (D10).

By day 10 of cultures, myotubes showed high rates of spontaneous contractions, see, FIG. 11. Therefore, experiments were designed for identifying media that would reduce spontaneous contractions in cultures.

FIG. 11: Shows human skeletal muscle cells (hSkMCs) forming myofibers within 8 days post seeding (co-cultures) having spontaneous myo-tube contractions at Day (D) 10 culture that are reduced by using conM culture medium in a microfluidic chip.

Figures 11A, 11B, 11C:
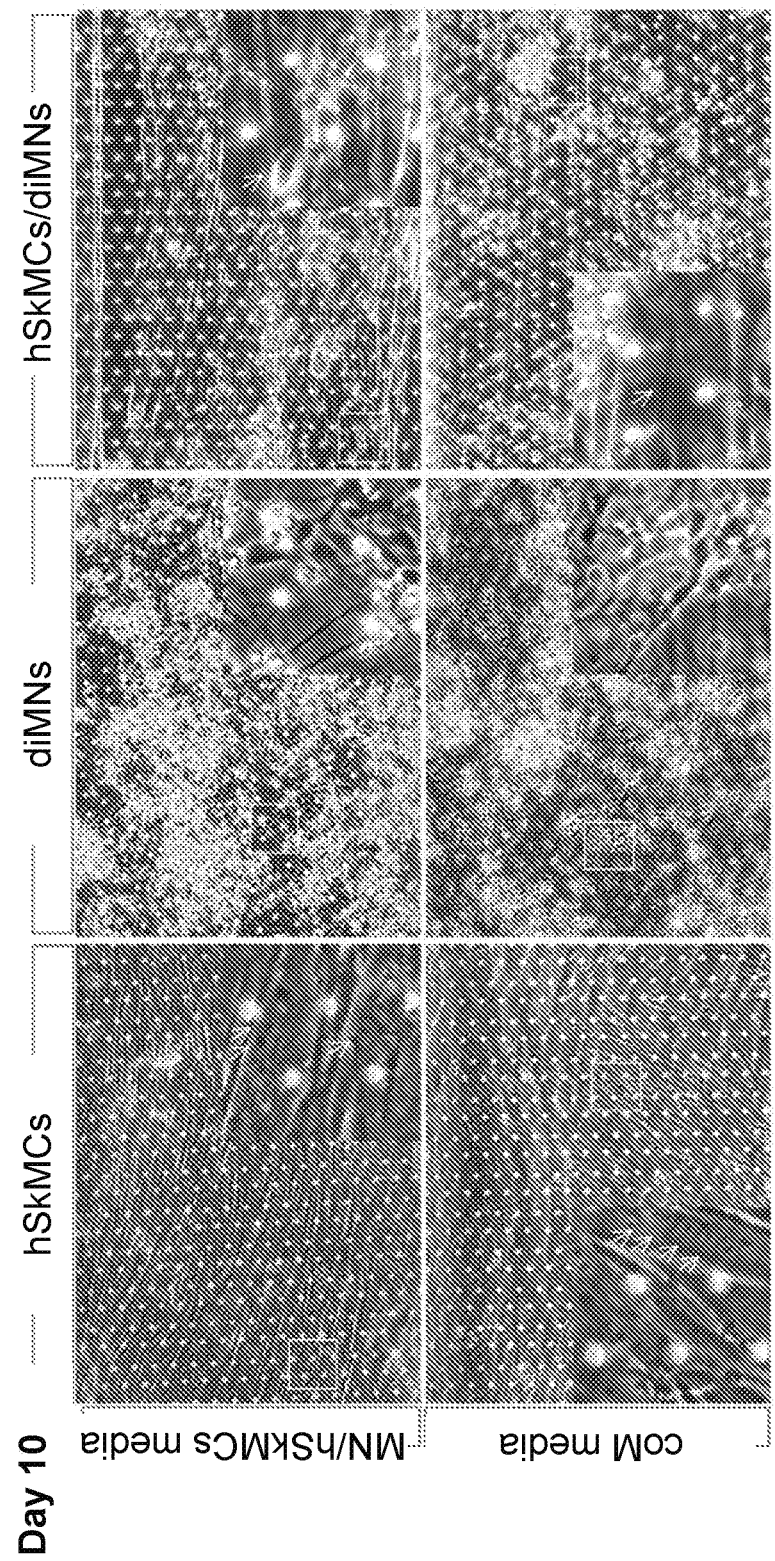
FIG. 11A: shows micrographs of hSkMCs growing in chips. White arrows in the magnified region point to multinucleated muscle cell fibers, of which there appears to be more nuclei per fiber in the coM medium.
FIG. 11B: shows micrographs of diMNs growing in chips.
FIG. 11C: shows micrographs of shSkMCs/diMNs grown in MN/hSkMCs media (upper row of micrographs) and coM medium (lower row of micrographs) growing in chips. Spontaneous myo-tube contraction was observed only in diMNs/hSKMC co-cultures. White arrows in the magnified region point to contacts of MN with a muscle cell fiber.

FIG. 11A: shows micrographs of hSkMCs growing in chips. White arrows in the magnified region point to multinucleated muscle cell fibers, of which there appears to be more nuclei per fiber in the coM medium;

FIG. 11B: shows micrographs of diMNs growing in chips; and

FIG. 11C: shows micrographs of shSkMCs/diMNs grown in MN/hSkMCs media (upper row of micrographs) and coM medium (lower row of micrographs) growing in chips. Spontaneous myo-tube contraction was observed only in diMNs/hSKMC co-cultures. White arrows in the magnified region point to contacts of MN with a muscle cell fiber.

Inserts show higher magnified areas of cells outlined in the white box for each micrograph.

FIG. 12: Shows human skeletal muscle cells (hSkMCs) as myofibers with spontaneous myotube contraction at Day (D) 10 (Experiment 3).

FIG. 12A: shows a micrograph of hSkMCs as myotubes growing on top of a membrane of the microfluidic chip in coM media.

FIG. 12B: shows a graph comparing contractions per minute for a myofiber contraction frequency with an average of fibers in two experiments (Experiment 1 and 3) that were combined for a total estimation of myofiber contraction frequency.

FIG. 12C: shows a graph comparing contractions per minute for myofibers having an increased myofiber contraction frequency between Laminin vs. cross linked Laminin ECM, at about the same frequency as shown in FIG. 12B.

FIG. 12D: shows a graph comparing contractions per minute for myofibers grown in regular media compared to a culture grown in coM media. When cultured in coM, contraction frequency is around 25% less compared to regular medium conditions.

FIG. 13: Shows schematic illustrations of experimental timelines for comparing co-cultures of hSkMCs with MNs, with and without coM media. The use of coM media allows the control of myofiber structure and function over time.

FIG. 1A3: shows a schematic illustration of a timeline and cell densities for Group 1 and Group 2 in coM: hSkMCs seeded at $5 \times 10^6$/ml cells and MNs seeded at $3 \times 10^6$/ml cells. hSkMCs seeded Day (D) 0 with differentiation (diff) initiated on D1, Day 12 MNs seeded D1 (as one example 18h later), D5 formation of myotubes & medium switch to coM, no myofiber contractions observed D10, no loss of myofibers observed on D12, fixation and analysis by ICC on D14, duplicate chips on D20 showed no loss of myofibers.

FIG. 13B: shows a schematic illustration of a timeline and cell densities for Group3: hSkMCs seeded with MNs: Day 0: seeding hSkMCs; Day 1: (18 h later) seeded diMNs (d12); Day 5: formation of myotubes, no medium switch; Day 10: observation of myofiber contraction; Day 11: observing progressive loss of myofibers; Day 14: fixation and analysis by ICC; in chip cultures left to D20, there is almost a complete loss of myofibers.

VI. Co-Localization of iPS-Derived MNs and Muscle Cells Showing Potential Formation of NMJs in Microfluidic NMJ-On-Chip.

During the development of one embodiment of a functional NMJ-on-Chip, method steps for a successful motor neuron-on-chip are as follows: obtain patient iPSC-derived MNs, grown under conditions for inducing expression of certain neuronal markers by day 12, develop a successful skeletal muscle-on-chip: containing contractile tissue (i.e. myofibers), then co-culture skeletal muscle cells and neuronal cells on microfluidic chips under conditions to stop spontaneous contraction by adding blockers, such as calcium channel blockers, sodium channel blockers, tetrodotoxin (TTX), which is a potent blocker of voltage-gated calcium channels, and the like, to the media. Use immunohistochemistry (ICH) to identify characteristics of NMJs. Chip components include membranes with a pore Dia (diameter) of 7 μm, spacing 40 μm Hex packed, Thickness: 50 μm, PDMS, Extracellular Matrix (ECM) provided is laminin (250 μg/ml).

Thus, the following embodiments are provided for identifying NMJs on functional NMJ-on-chips, e.g., using co-localization of neuronal bulb markers, e.g. BTX, e.g. Tubb3 with muscle cells e.g. MHC.

V. Using Microfluidic NMJ-On-Chip Under Flow for Longer Studies.

Experiment 4: Extended cultures up to day 37.

Experiment 4 showed that hSKMC integrity in chip is expandable over time (in monoculture).

FIG. 16: shows schematic illustrations of tall channel microfluidic NMJ-on-chip with one embodiment of an experimental timeline (Experiment 4) set up and time course for comparing co-cultures of hSKMCs with MNs under flow.

FIG. 16A: shows a schematic illustration of a tall channel microfluidic chip, from left to right, view of vertical 2-channel chip (i.e. the top channel is above the bottom channel as shown in Stage 1, with hSKMCs covering the entire surface of the bottom channel, and Stage 2 with diMNs seeded into the top channel.

FIG. 16B: shows a schematic illustration of one embodiment of a timeline where hSKMCs are seeded Day (D) 0 with differentiation (diff) initiated on D1, D5: formation of myotubes & medium switch to coM media, then Day 7-10: no myofiber contraction, on Day 20 start muscle cells under flow at 10 ul/hour, continued to D29 when flow is stopped. Day 30: seed diMNs (d12) (not in coM media for observing baseline contractions). Day 37: myotubes are spontaneously contracting: fixation and analysis (including ICC).

FIG. 17: shows an exemplary co-localization study of iPS-Derived MNs and Muscle Cells showing formation of NMJs between diMNs and hSkMCs (Experiment 4). Cells were stained with α-bungarotoxin (BTX) for identifying suggestive NMJ areas where motor end plate (green), neurons are stained with Tubulin beta-3 chain (Tubb3) (red) and muscle myosin heavy chain (MHC) (blue) were fluorescently imaged on individual channels then merged. The blue channel of MHC staining is not shown in FIG. 17A-17D.

FIG. 17A: shows a low power fluorescent micrograph where Tubb3 (red) neuronal staining shows neurite extension along myotubes with oval areas (green) suggestive of lower motor nerve termini whose distribution over a myotube suggests motor end plates.

FIG. 17B-G: shows higher power fluorescent micrographs of the suggestive NMJ areas (white arrows) are identified by superimposed staining i.e. co-localization, where the red stained nerve terminal neuron bulb is co-localized with BTX green staining of motor end plates producing a yellow NMJ.

FIG. 17E-17G: The blue channel of MHC staining is shown showing a MHC containing muscle fiber at the yellow stained NMJ.

FIG. 18: shows florescent micrographs of stained cells in a microfluidic chip. Co-Localization Study of iPS-Derived MNs and Muscle Cells. Both diMNs and hSkMCs are in close proximity to each other as determined from initial ICC analysis and 3D reconstruction of confocal microscope images (i.e. combined z-stacks). A partial loss of myotubes were observed due to lack of ECM stability FIG. 18A and FIG. 18B: α-bungarotoxin (BTX) for identifying the motor end plate (green), skeletal muscle marker, desmin, (red) and DNA (DAPI) (shown in blue). The red muscle fiber is multinucleated with numerous green motor end plates.

FIG. 18B: a higher magnification of FIG. 18A, 3 white arrows point to co-localization of α-bungarotoxin (BTX) for identifying the motor end plate (green) and skeletal muscle marker, desmin, (red) as olive, white dark orange areas depending upon concentration of stain.

FIG. 18C and FIG. 18D: motor end plate (green) BTX and neurofilament H non-phosphorylated (SMI 32) (red) and DNA (DAPI) (shown in blue).

FIG. 18D: a higher magnification of FIG. 18C, 3 white arrows point to co-localization of a motor end plate (green) BTX, neurofilament H non-phosphorylated (SMI 32) (red) as olive—white areas depending upon concentration of stain.

VI. Using Microfluidic NMJ-On-Chip for Pharmacology Studies and Live Imaging of Cells within Channels.

In this embodiment, an experimental time line (course) is described for seeding hSkMCs up to 9 days prior to seeding MNs in the upper channel. Spontaneous contractions are allowed to begin by removing CoM media at the start of the pharmacology assay.

Experiment 5 showed that pharmacology and imaging was possible for measuring functional NMJ interactions.

FIG. 19: shows schematic illustrations of one embodiment of experimental timelines for using NMJ-on-chips (Experiment 5) as a set up and time course for using co-cultures of hSKMCs with MNs for live imaging and pharmacology studies.

FIG. 19A: shows a schematic illustration of a tall channel microfluidic chip, seeded with hSKMCs at Day 0 (D0) in the bottom channel, culting up to D9, without observing muscle contractions, then D9 seeding diMNs (d12). In one embodiment only in Group 2. In some embodiments, more than one group of hSKMCs receive MNs. On days 15, 16 and/or 17, live imaging of pharmacology assays are done as shown schematically, for one example, in FIG. 19B.

FIG. 19B: shows a schematic illustration of one embodiment of a timeline where a NMJ-On-Chip with spontaneous contracting muscle fibers is used for a pharmacology study, i.e. testing agents for inducing or reducing muscle contractions on a baseline chip with or without spontaneously contracting myofibers, in one embodiment, treating NMJ chip with 75 uM Glutamine (Glut) in the NM (upper) channel), in one embodiment, treating NMJ chip with 12 uM alpha-turbocurarine in the hSKMC (lower) channel, in one embodiment, washing out alpha-turbocurarine, in one embodiment, treating NMJ chip with 100 uM Glutamine (Glut) in the NM (upper) channel).

FIG. 20: Shows exemplary High Content Imaging as immunohistochemistry of iPSC derived Myo-fibers, on fixed cells (Experiment 5).

FIG. 20A: shows a fluorescent micrograph of the entire width and length of immunostained cells in a microfluidic NMJ chip. α-bungarotoxin BTX (green), Neuron-specific Class III β-tubulin (TuJ1) (red) and myosin heavy chain (MHC) (blue).

FIG. 20B: shows a higher power fluorescent micrograph of the channel in the chip shown in FIG. 20A.

FIG. 21: shows micrographs of cells grown as shown in Experiment 5 for pharmacology and in-chip imaging for NMJ-On-Chip.

FIG. 21A: shows phase contrast micrographs of myotubes and neurons in chips, higher magnified areas are shown below the larger micrograph white arrows point to potential NMJs where myotubes are adjacent to neurons.

FIG. 21B: shows fluorescent micrographs of superimposed (co-localized images) of neurons stained with a neuronal microtubule marker, Tau, (green) a microtubule stabilization protein, for identifying neurons and motor end plates with BTX (red) (labeling AChRs) for identifying NMJs, where neuronal braches co-localize with end plates. Smaller micrographs show higher magnified areas outlined by corresponding white boxes. White arrows point to motor end plates of myotubes, some of which are in close proximity to neuronal axons.

FIG. 22: shows an exemplary method of growing motor neurons in a microfluidic chip where the MN cells of neural networks have spontaneous calcium bursts. Experiment 5.

FIG. 22AA: shows a microfluidic chip seeded with MNs at day 12 of culture.

FIG. 22BB: shows an exemplary timeline where MN precursor cells from Day 12 cultures are seeded at Day 0 in the microfluidic chip, MN network formation is observed a Day 10 on the chip (Day 18 overall from the start of the original MN culture).

FIG. 22CC: shows exemplary images produced by high content life imaging of cells in chips showing Ca++ imaging of diMN cells on Day 12 after seeding onto the microfluidic chip; at high magnification (20×). diMNs show repetitive calcium bursts as visualized via Flou4 labeling in color within the cellular areas, e.g. cell bodies, axons and terminal bulbs, in neuronal networks, where the concentrations of Ca++ are shown by yellow-lower levels, red-higher than yellow areas and highest levels in white areas within the red areas, as shown in the neuron cell bodies.

FIG. 22A: shows exemplary Ca++ imaging of FIG. 22CC in black and white, where the highest amounts of Ca++ are white areas in black and white micrographs, white arrowheads point to cellular areas with concentrated Ca++.

FIG. 22B: shows a higher magnification of a cell in the center of the micrograph in FIG. 22CC/FIG. 22A with two white arrowhead markers used to identify the same area through the different planes of focus.

FIGS. 22D-22J: shows exemplary Ca++ imaging in color from confocal high content micrograph z-stack layers through the cell (shown in FIG. 22B) where higher concentrations of Ca++ are shown by yellow/red/white areas in the neuronal cytoplasm, which discharge and recharge then discharge over time. White arrowheads mark the same location of the cell shown in FIG. 22B-FIG. 22J.

FIG. 22K: shows a graph of average intensity of Ca++ vs. elapsed time (seconds).

Description of Microfluidic Chips

It is not intended that the present invention be limited by the nature of the "microfluidic device" or "chip." However, preferred microfluidic devices and chips are described in U.S. Pat. No. 8,647,861, hereby incorporated by reference, and they are microfluidic "organ-on-chip" devices including living cells in microchannels, e.g. cells on membranes in microchannels exposed to culture fluid at a flow rate. It is important to note that the features enabling the actuation of strain or mechanical forces on the cells within the "organ-on-chip" device are optional with regards to the "NMJ-on-chip" and may be omitted.

FIG. 14: Shows schematic illustrations of embodiments of a microfluidic device.

FIG. 14A: is a schematic illustration showing one embodiment of the microfluidic device or chip (16), including two microchannels (1), each with an inlet and outlet port for the upper channel (2) and lower channel (3), as well as (optional) vacuum ports (4).

Microfluidic devices are conveniently made of polydimethylsiloxane (PDMS), polyurethane, polycarbonate, polystyrene, polymethyl methacrylate, polyimide, styrene-ethylene-butylene-styrene (SEBS), polypropylene, or any combinations thereof. The present invention contemplates treatment of such substances to promote cell adhesion, selection or differentiation or fluid wetting such as treatments selected from the group consisting of plasma treatment, ion treatment, gas-phase deposition, liquid-phase deposition, adsorption, absorption or chemical reaction with one or more agents.

FIG. 14B: is a topside schematic of an embodiment of the perfusion disposable or "pod" (10) featuring the transparent (or translucent) cover (11) over the reservoirs (12), with the chip (16) inserted in the carrier (17). The chip can be seeded with cells and then placed in a carrier for insertion into the perfusion disposable or pod, whereupon culture media in the reservoirs flows into the microchannels and perfuses the cells (e.g. both MNs and hSMCs).

In one embodiment, the microchannel includes a surface including a silicone polymer. In one embodiment, the silicone polymer is polydimethylsiloxane or "PDMS." In one embodiment, the ECM protein is covalently coupled to a PDMS surface using a crosslinker.

In one embodiment, one or more proteins (e.g. ECM proteins) or peptides (e.g. RGD) are covalently coupled to the surface of a microchannel of a microfluidic device.

It is not intended that the present invention be limited to any particular protein or peptide; a variety are contemplated, including mixtures. For example, in one embodiment, the covalently attached protein is laminin or collagen. In another embodiment, a mixture of proteins are covalently attached, e.g. a mixture of collagen type I, fibronectin and collagen type IV. In yet another embodiment, the RGD peptide is attached (or a peptide including the RGD motif is attached).

In one embodiment, the present invention contemplates a method of culturing skeletal muscle cells, including: a) providing a microfluidic device including a microchannel including a surface, said microchannel in fluidic communication with a fluid source including fluid; b) covalently attaching one or more proteins or peptides to said microchannel surface so as to create a treated surface; c) seeding viable skeletal muscle cells on said treated surface so as to create attached cells; c) flowing fluid from said fluid source through said microchannel so as to create flowing conditions; and d) culturing said attached cells under said flow conditions such that said cells remain attached and viable.

It is not intended that the present invention be limited by the manner in which the proteins or peptides are covalently attached. In one embodiment, a crosslinker is used. In another embodiment, a bifunctional crosslinker is used.

A variety of such crosslinkers are available commercially, including (but not limited to) the following compounds:

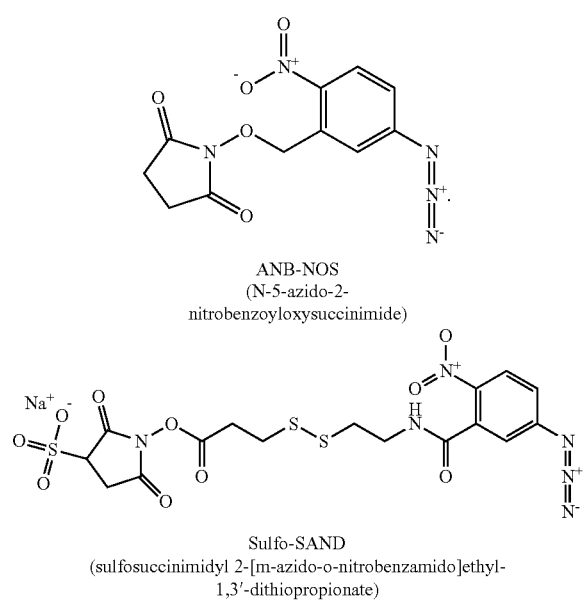

ANB-NOS
(N-5-azido-2-nitrobenzoyloxysuccinimide)

Sulfo-SAND
(sulfosuccinimidyl 2-[m-azido-o-nitrobenzamido]ethyl-1,3′-dithiopropionate)

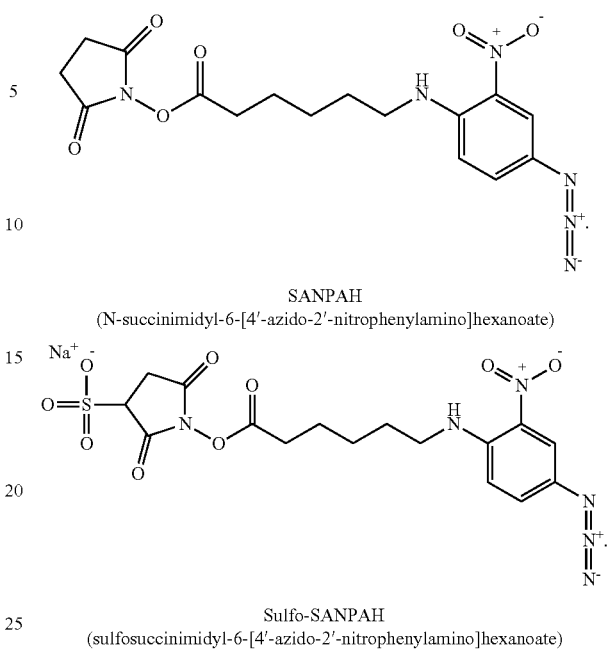

SANPAH
(N-succinimidyl-6-[4′-azido-2′-nitrophenylamino]hexanoate)

Sulfo-SANPAH
(sulfosuccinimidyl-6-[4′-azido-2′-nitrophenylamino]hexanoate)

By way of example, sulfosuccinimidyl 6-(4'-azido-2'-nitrophenyl-amino) hexanoate or "Sulfo-SANPAH" (commercially available from Pierce) is a long-arm (18.2 angstrom) crosslinker that contains an amine-reactive N-hydroxysuccinimide (NHS) ester and a photoactivatable nitrophenyl azide. NHS esters react efficiently with primary amino groups (—NH2) in pH 7-9 buffers to form stable amide bonds. The reaction results in the release of N-hydroxy-succinimide. When exposed to UV light, nitrophenyl azides form a nitrene group that can initiate addition reactions with double bonds, insertion into C—H and N—H sites, or subsequent ring expansion to react with a nucleophile (e.g., primary amines). The latter reaction path dominates when primary amines are present.

Sulfo-SANPAH should be used with non-amine-containing buffers at pH 7-9 such as 20 mM sodium phosphate, 0.15M NaCl; 20 mM HEPES; 100 mM carbonate/bicarbonate; or 50 mM borate. Tris, glycine or sulfhydryl-containing buffers should not be used. Tris and glycine will compete with the intended reaction and thiols can reduce the azido group.

For photolysis, one should use a UV lamp that irradiates at 300-460 nm. High wattage lamps are more effective and require shorter exposure times than low wattage lamps. UV lamps that emit light at 254 nm should be avoided; this wavelength causes proteins to photodestruct. Filters that remove light at wavelengths below 300 nm are ideal. Using a second filter that removes wavelengths above 370 nm could be beneficial but is not essential.

While a variety of protocols were explored, one embodiment of a method for preparing and seeding a microfluidic chip includes: first, the chip (or regions thereof) are treated to promote wetting or protein adhesion (e.g. by plasma treatment). Second, one or more channels are then plugged (see the top schematic of FIG. 15A, where an "X" indicates a channel is blocked in a microfluidic device or chip with top and bottom channels). FIG. 15B shows how the ports of a microfluidic device can be utilized to introduce fluid (e.g. with ECMs) or cells using pipette tips. Using the protocol, the ECM mixture for the bottom channel is introduced before coating the top of the membrane, with the excess removed, and the remainder dried. Thereafter, the ECM for the top channel is introduced. The hSMCs can be seeded on the bottom channel. The top channel can be washed. Finally, the neural cells can be introduced and incubated for attachment.

The surfaces of the microchannels and/or the membrane can be coated with cell adhesive, selective or promotive molecules to support the attachment of cells and promote their organization into tissues. Where a membrane is used, tissues can form on either the upper surface of the membrane, the lower surface of the membrane, any of the surfaces of the channels or cavities present on either side of the membrane or any combination thereof.

FIG. 15: Shows schematic illustrations showing one embodiment of microfluidic devices, including for providing an "air dam" for isolating one channel.

FIG. 15A: is a schematic illustration showing one embodiment of a microfluidic device or chip (16) (viewed from above), the device includes top (apical; dotted line) and bottom (basal; solid line) channels. As an example, motor neurons are seeded into the upper (apical) channel and human skeletal muscle cells are seeded into the lower (basal) channel. In one embodiment, an "air dam" is created for part of a protocol, described below, where the two Xs are indicating that channels are blocked during at least part of the protocol.

FIG. 15B: is a schematic illustration showing one embodiment of how ports, upper (2) and lower (3) of a microfluidic device or chip (16) can be utilized to deposit fluids carrying surface coatings (e.g. dissolved proteins) and/or seed the cells using pipette tips. This image, in part, shows one embodiment of a modification to the typical chip ECM coating protocol based on the need in some embodiments to coat the top and/or bottom channels with different ECM solutions in wet and/or dry conditions.

In one embodiment, the upper channel port (2) is blocked, while ECM or cells are added to the lower channel port (3).

The procedure developed involved an "air dam" by which perfusion of ECM1, for example, loaded into the top channel (apical; dotted line) was prevented from perfusing through the membrane to the bottom channel (basal; solid line) by clamping flexible tubing and trapping air in the bottom channel, FIG. 16A. The ports of a second microfluidic channel can be air-filled and plugged up using clips, for example. For covering the surface of the lower channel, the ports (2) for the top channel are plugged for preventing perfusing of ECM, such as laminin, through the membrane into the upper channel.

In one embodiment, different cells are living on the upper and lower surfaces, thereby creating one or more tissue-tissue interfaces separated by the membrane. The membrane may be porous, flexible, elastic, or a combination thereof with pores large enough to only permit exchange of gases and/or small chemicals, or large enough to permit migration and transchannel passage of large proteins, as well as whole living cells and/or portions thereof (e.g. forming neuronal terminal synapses with muscle cells). Depending on the size-scale of the pores and manufacturing preferences, the pores may be defined, for example, using lithography, molding, laser-drilling or track-etching, intrinsic to a selected material (for example, polyacrylamide gel, collagen gel, paper, cellulose) or engineered into the material (e.g. by generating an open-cell polymer or matrix).

Flow is important and stands in contrast to static 2D culture. Using a flow in the microchannel(s) allows for the perfusion of cell culture medium throughout the cell culture during in vitro studies and as such offer a more in vivo-like physical environment. In simple terms, an inlet port (2 and 3) allows injection of cell culture medium, test agents, etc. into a cell-laden microfluidic channel (1) or chamber (1), thus delivering nutrients and oxygen to cells. An outlet port (2 and 3) then permits the exit of remaining liquid as well as harmful metabolic by-products. While continuous flow is preferable due to its application of controlled shear forces, either of the device's fluidic paths could also be cultured under "stop flow" conditions, where the flow is engaged intermittently, interspersed by static culture.

It is not intended that the present invention be limited to particular "flow rates" or means for generating flow rates. In one embodiment, a flow rate of between 5 and 200 uL/hr, and more preferably between 20-100 uL/hr, and still more preferably between 10 and 60 uL/hr, and still more preferably between 20-50 uL/hr, is contemplated. In one embodiment, pressure is applied through the lid and the lid seals against the reservoir(s). For example, when one applies 1 kPa, this nominal pressure results, in one embodiment, in a flow rate of approximately 30-40 uL/hr. When one applies a pressure of between 0.5 kPa, this nominal pressure results, in one embodiment, in a flow rate of between 15 uL/hr and 30 uL/hr.

In one embodiment, a tall 2 chamber (upper and lower) PDMS microfluidic Chip has a membrane separating the two chambers having a pore diameter of 7 μm, spacing: 40 μm Hex packed, thickness: 50 μm, extracellular matrix (ECM) provided is laminin (250 m/ml).

EXAMPLES

Example 1

In this example, several exemplary embodiments are provided for the generation of motor neurons is provided using iPSCs as the starting material, see FIGS. 33 and 34. In one embodiment, a MN-on-chip is provided with MNs seeded into the upper channel of a microfluidic chip. In another embodiment, MNs are seeded into the upper channel of a NMJ-On-Chip.

Cells are prepared either directly from cultured iPSCs or from frozen lots of pre-differentiated cells. Cells are thawed (or dissociated fresh) and seeded into the chip at day 12 (in the case of iMN differentiation) and at various points in neural differentiation.

More specifically, for example, MN cells are seeded at day 12 of differentiation either from freshly differentiated cultures or directly from a thawed vial into a microfluidic chip described herein.

CALCIUM FLUX: FIG. 22 show the results of calcium flux imaging in the upper neural channel. Using a florescent calcium influx-activated dye (Fluo-4), neurons seeded in chip were imaged using a high-resolution high frame-rate camera. Florescence intensity changes of up to hundreds of neurons were analyzed simultaneously by recording average pixel intensity over time (dF/F). These values were plotted with respect to time and are analyzed for waveform properties, which correlate spontaneous neural activity and neural network formation. This is accomplished through multi-step video post-processing and signal analysis (including video compression, signal cleanup, automatic or manual ROI detection, etc. which can be implemented from open-source MATLAB software packages). The photograph (FIG. 22CC) is a single fluorescent image from a movie of such images. The colored areas (yellow, red and white within red areas) indicate areas of Ca++ hot spots, i.e. higher concentrations of Ca++. The addition of tetrodotoxin (TTX), which is a potent blocker of voltage-gated calcium channels, ablates this activity. This type of experiment is contemplated to show neuronal activity modulated by pharmacological stimulation.

In a controlled study, live cell imaging was performed on diMNs that had been cultured in the chip (MN-on-Chip) (FIGS. 22BB-22J). High content imaging of neuron calcium flux was recorded and plotted with respect to time (FIG. 22K). Calcium flux events or peaks correspond to neural activity and were counted by both automated software and blinded human technician. Each event was assigned a time-stamped value and depicted for each tracked neuron with respect to time. This Calcium (Ca++) flux live cell assay showed Ca flux in relation to spontaneous neuronal activity, i.e. firing. For examples, see FIG. 22.

Example 2

In this example, several exemplary embodiments are provided for the generation of hSKMCs on microfluidic chips for skeletal muscle cells-on-chips (and then for NMJ-On-Chips), using myoblasts and/or iPSCs as the starting material.

The following describes exemplary methods, e.g. for differentiating iPSCs, providing a Muscle Cell Culture-on-Chip.

Skeletal Muscle Differentiation from Human iPSCS.

The starting density of cells affects the success of skeletal muscle cell differentiation. The starting iPSc density described herein is exemplary for the cell lines described herein. However each iPSC line is different so the optimal density should be determined according to each individual cell line's growth (e.g. doubling) rate. For cell lines shown herein, an exemplary recommended cell density and volume of media: 12 or 24 wells 15,000-18000 cells/cm$^2$ and for 96 wells 5000 cells/cm$^2$. One embodiment for a method providing human induced pluripotent stem cells (iPSCs) for use in providing induced hSKMCs is described as follows.

Coat plates with ECM, e.g. Matrigel. Add appropriate volume, see e.g. below, in a sterile tissue culture hood. For a 6 well plate—1 mL/well; 24 well plate—250 μL/well; and 96 well plate—50 μL/well. Leave Matrigel in wells for at least 1 hr at room temperature for coating surfaces. Coating may also be done for more than an hour.

For deriving human iPSC (hiPSC) skeletal cell cultures from hiPSCs: Grow and expand iPSC cultures on Matrigel coated surfaces with mTeSR Media supplemented with Rock Inhibitor (Y-27632) (such as from Sigma-Aldrich, St. Louis, Mo. 63103-USA), at exemplary concentrations from 2.0 uM, 2.5 uM, 5 uM. 10 uM, up to 20 uM, for one day. Nonlimiting examples of mTeSR Media include, cGMP mTeSR™1, mTeSR™1, TeSR™2, TeSR™-E7™, TeSR™-E5, TeSR™-E6, ReproTeSR™, mTeSR™3D, etc., defined, serum-free media for culture of human ES, iPS, pluripotent stem cells, and the like). Clean iPSCs cells daily by removing differentiated cells to maintain a spontaneous differentiation free culture for optimal skeletal muscle differentiation. In one embodiment, 3 wells of a 96 well plate containing iPSCs, maintained at 70-80% confluence is suggested for use to start differentiation.

More specifically, Stage 1 skeletal muscle induction: Step 1. Dissociate iPSCs with Accutase (e.g. of a cell detachment solution) for 5 min.; Step 2. Resuspend cells in phosphate buffered saline (PBS) in a 15 mL conical tube; Step 3. Centrifuge the cells for 5 min (minutes) at 1000 RPM (revolutions per minute) for spinning cells gently to the bottom of the tube; Step 4. Aspirate media without disturbing the cell pellet in the bottom of the tube, then resuspend cells in skeletal muscle induction media 1, DMEM/F12, (see, Table 1); Step 5. Count the number of live cells (in part by exclusion staining the dead cells), e.g. using an automated cell counter: Take out 10 ul of cell suspension from the tube, mix with 10 ul of dye (1:1), e.g. in Trypan blue dye for staining dead cells, mix well, load mixture in cell counter chamber to count; Determine live cell numbers per ml, then Step 6. Plate single cells with appropriate number of cells, as suggested herein, on a Matrigel coated plate in mTeSR Media supplemented with Rock Inhibitor (Y-27632), see exemplary materials and concentrations above, for one day; Step 7. On the next day, switch the Stage 1 media to DMEM/F12 (1:1) supplemented with exemplary concentrations of 3 uM CHIR99021, 05 uM LDN193189; Step 8. Change media everyday until day three; then Step 9. On Day three, supplement the existing media with an exemplary concentration of 20 ng/mL bFGF and continue feeding for additional seven days. Media should be change on a daily basis.

Stage 2—Commitment to Myoblasts. 1. After 10 days of incubation (e.g. 7 days incubation in complete skeletal muscle induction media 1), the media is changed to a DMEM/F12 (1:1) supplemented with exemplary concentrations of 10 ng/ml HGF, 2 ng/ml IGF and 0.5 uM LDN193189 (Skeletal Muscle Induction Media 2) for two days of incubation, see Table 2; If cells are too confluent by day 12-14, cells should be dissociated and replated on ECM, e.g. Matrigel coated surfaces at recommended cell densities, mentioned above, for optimal results; and 2. On day 12, cells were cultured with DMEM/F12 (1:1), with exemplary concentrations of 15% KSOR supplemented with an exemplary concentrations of 2 ng/ml IGF (incomplete Skeletal Muscle Induction Media 3), see Table 3; for up to four days.

Stage 3 Maturation: For differentiation of myoblasts into myotubes and for maintenance of skeletal muscles: 1. On Day 12, 13 or 14, media was changed to DMEM/F12 (1:1), with exemplary concentrations of 15% KSOR supplemented with 10 ng/mL HGF and 10 ng/mL IGF-1 (complete Skeletal Muscle Induction Media 3), see Table 3; 2. Change Media every other Day until used, up to day 40; and 3. Optional: Fix cell samples, up to day 40 (or day used), e.g. of fixative, 4% PFA (Paraformaldehyde) to stain for skeletal muscle markers, e.g. as described herein. Other fixatives may be used for immunostaining.

The exemplary protocol described here for differentiating hSKMCs was used on ECM coated substrates, such as plates and microfluidic channels. For examples of ECM, plates and channels were coated with Matrigel, while microfluidic channels were coated with Laminin (non-cross-linked) and cross-Linked Laminin, as described herein. Seeding densities for the chips were used as described for the experiments, where either ihSkMCs were differentiated as described here, as one example, starting myotube differentiation on D1 in Stage 1 Skeletal Muscle Induction Media (incomplete).

Example 3

In this example, several exemplary embodiments are provided for the generation of hSKMCs on microfluidic chips coated with ECM for testing Extracellular Matrix effects on myotube structure and stability.

A. Extracellular Matrix (ECM).

In some embodiments, an extracellular matrix (ECM) layer is provided to coat (cover) the entire surface (bottom, sides and top) of the lower channel for growing human skeletal striated muscle cells. In one embodiment, Laminin was used as an exemplary ECM component for coating the surface. In another embodiment, a cross-linker chemical was used for cross-linking Laminin molecules. As an exemplary cross-linker chemical, Sulfo-SANPAH was used.

FIG. 4: Shows one embodiment of a human skeletal muscle cell culture hSkMC-In-Chip: Extracellular Matrix (ECM) use for hSKMCs-In-Chip. In one embodiment, the chip is a Quad chip.

FIG. 4A: shows a picture of a single channel (Quad) Chip with pipette tips used to block channels for coating the inside surfaces with an ECM layer then seeded with human skeletal muscle cells (hSKMCs).

FIG. 4B: shows a schematic illustration of a cross-sectional view of the quad channel with ECM as Laminine (purple and blue stars) with hSKMCs as yellow-spotted blocks.

FIG. 4C: shows a schematic illustration of a cross-sectional view of the quad channel with ECM as Laminine (purple and blue stars) with hSKMCs as yellow-spotted blocks and a representative cross linking of ECM as yellow stars, e.g. with Sulfo-SANPAH.

B. Extracellular Matrix (ECM) Cross-Linking Effects on Myotube Structure and Stability in Chips.

This example shows one embodiment of a set up and time course for culturing Human Muscle Cells in-Chip: providing non-contracting myotubes on ECM coated chips. As one embodiment, a single channel chip (e.g. Quad chip: as a 4 single channel chip) was used initially for determining stages of muscle cell maturation on a chip, effects of ECM, and numbers of seeded cells that provide viable cultures in relation to chips coated with ECM. In this embodiment, muscle cells grown without nerve cells present did not show spontaneous contractions of myotubes.

Experiment 2 showed that Sulfo-SANPAH cross linked ECM provides more stability to hSKMCs. As one example, Sulfo-SANPAH cross-linked ECM enables formation of almost 2-fold more MHC positive multinucleated fibers. Further, more nuclei per myo-tubes with cross-linked ECM. In fact, a 3-fold higher number of nuclei in WIC myo-fibers seeded on Sulfo-SANPAH cross-linked ECM-Laminin was observed over a Laminin coating without the use of a cross-linker.

FIG. 5: shows one embodiment of a human muscle cell culture in-chip: Set Up and Time Course for producing multinucleated myofibers that are not contracting.

FIG. 5A: Single channels of Quad Chips were seeded with human skeletal muscle cells (hSKMCs). Group 1 and Group 2: $5 \times 10^6$/ml cells; Group 3 and Group 4: $1.6 \times 10^6$/ml cells. Groups 1 and 3 do not have cross (X)-linked ECM while Groups 2 and 4 have exemplary Sulpho-SANPAH X-linked ECM.

FIG. 5B: shows a schematic experimental timeline: Seeding cells on Day (D) 0. D1: Inducing differentiation. D5 observing fusion of myoblast cells. D10: Screening for myo-fiber contraction in cultures that were not stained for analysis; observing polynucleated fibers but no myofiber contractions. D14 Fixing cells and fusion-index-analysis.

FIG. 5C: Day 14: Fixation and fusion-index-analysis based upon staining for myosin heavy chain (MHC) (red) and nuclei (DNA) (shown in blue).

FIG. 5D: Shows a schematic illustration of multinucleated myofibers in WIC (red) and nuclei (DNA) (blue).

FIG. 6: shows Human Skeletal Myoblast-Derived Poly-Nucleated Fibers growing in microfluidic chips where Sulfo-SANPAH cross-linked ECM enables formation of almost 2-fold more MHC positive multinucleated fibers.

FIG. 6A-6D: show fluorescent micrographs of immunostained myosin heavy chain (MHC) (red) myo-fibers and DAPI stained nuclei (DNA) (shown in blue) comparing cultures started at the 2 different densities (FIGS. 6A-B: $5 \times 10^6$/ml cells and FIGS. 6C-6D: $1.6 \times 10^6$/ml cells) with and without cross-lined (X-link) ECM-Laminin (Lam).

FIGS. 6E-6F: show phase contrast micrographs of Day 14 cells grown on Laminin (Lam) and cross-linked (X-Link) ECM-Laminin (Lam), respectively. More MHC positive multinucleated fibers are observed with X-Linked Laminin after 14 days. White arrows point to 2 exemplary multinucleated myotubes FIG. 6G: shows a graph comparing number MHC+ myofibers to the treatments shown in FIGS. 6A-6D where at both cell densities the number of myofibers growing on x-Linked ECM is almost 2-fold more than fibers grown on regular, non-cross-linked, ECM.

FIG. 7: shows Human Skeletal Myoblast-Derived Poly-Nucleated Fibers growing in microfluidic chips comparing non-cross-linked to cross-linked ECM (Laminin) where more nuclei per myo-tubes are observed growing on cross-linked ECM.

FIG. 7A-7D: show fluorescent micrographs of immunostained myosin heavy chain (MHC) (red) myo-fibers and DAPI stained nuclei (DNA) (shown in blue) comparing cultures started at the 2 different densities with inserts showing higher magnifications of presumptive myo-fibers for each treatment.

FIGS. 7A-7B: $5 \times 10^6$/ml cells and FIGS. 6C-D: $1.6 \times 10^6$/ml cells) with Laminin (Lam) and with cross-linked (X-linked) Laminin-ECM.

FIGS. 7E-7F: Show a 3-fold higher number of nuclei in MHC myo-fibers seeded on exemplary Sulfo-SANPAH cross-linked ECM by graphical comparisons.

FIG. 7E: shows a graph comparing DAPI+ nuclei per MHC+ fiber for determining myo-fiber at the 4 treatments shown.

FIG. 7F: shows a graph comparing percentage of total DAPI+ per channel, i.e. percentage of DAPI in myo-fibers at the 4 treatments shown in FIG. 7A-D.

Example 4

In this example, exemplary embodiments are provided for a Human iPS-Derived MN and Muscle Cell Co-Culture in-Chip showing a loss of myotubes starting around 24 hours after start of spontaneous contractions.

Experiment 1: Human iPS-Derived MN and Muscle Cell Co-Culture in-Chip.

Day 0: seeding hSkMCs; Day 1: (18 h later) seeded diMNs (d12); Day 5: observation of formation of myotubes; Day 10: observation of myofiber contraction; Day 11: observation of progressive loss of myofibers; Day 14: fixation and analysis. There was a continuous loss of myo-tubes after day 11-24 hours, after last observation of spontaneous myo-tube contractions. Further, the use of flow during culture increases loss of myo-tubes. See, FIG. 9 for a schematic illustration and numbers of cells in the different replicates for comparing effects of initial seeding densities.

Experiment 1 showed that hSKMC seeding density at $3 \times 10^6$ cells/ml, but loss of cells 24 h after contracting activity.

FIG. 9: Shows one embodiment of a Human iPS-Derived MN and Muscle Cell Co-Culture in-a microfluidic Chip.

FIG. 9A is a picture of an exemplary microfluidic chip where day 12 MNs are seeded into the top (upper-blue) channel and hSkMCs are in the bottom (lower-red) channel;

FIG. 9B shows a schematic illustration of an exemplary cross section of NMJ microfluidic chip with day 12 MNs in the top channel and hSkMCs in the bottom channel with 3 sets of Experimental Chips for comparing cell densities at the time of seeding: Chip 1: top: $3\times10^6$/ml diMN cells and bottom: $5\times10^6$/ml hSkMC cells; Chip 2: top: $3\times10^6$/ml diMN cells and bottom: $10\times10^6$/ml hSKMC cells; and Chip 3: top: $3\times10^6$/ml diMN cells and bottom: $20\times10^6$/ml hSKMC cells.

FIG. 9C: shows a schematic illustration of a timeline showing co-culture of hSkMCs seeded Day (D) 0 with differentiation (diff) initiated on D1, Day 12 MNs seeded D1, Myofiber formation on D5, myofiber contractions observed D10, a loss of myofibers observed on D11, with fixation and analysis by ICC on D14.

Example 5

This example describes one embodiment of method steps for providing a functional NMJ-on-chip with reduced spontaneous myotube contractions. The following experiments were designed for identifying media components that would lower spontaneous contraction rates.

Media was tested that included at least one agent for reducing spontaneous myotube contraction rates. In part, rates were artificially reduced in order to allow testing of agents for altering muscle contractions, e.g. increasing muscle contraction rates.

By day 10 of cultures, observations of myotubes showed high rates of spontaneous contractions. Therefore, experiments were designed for identifying media that would reduce spontaneous contractions in cultures.

FIG. 10: shows one embodiment of an experimental system (Experiment 1) as a schematic illustration for testing medium to reduce spontaneous contractions of cells in the microfluidic tall channel chip. Experimental Groups 1-3 directly compare medium harvested from diMNs/hSKMC cultures with coM media in chips containing induced motor neurons (diMNs: Motor-neuron-on Chip) and human Skeletal Muscle Cells (hSkMCs-on-Chip), each cell type growing alone on chips then combined in the same chip in the same media (upper and lower channel) for providing a neuronal-muscular-junction (NMJ-on-Chip).

FIG. 10A: Group 1: shows a schematic illustration of the tall channel chip, with vacuum chambers (4), diMNs in the top channel but no cells in the bottom channel. Group 2: shows a schematic illustration of the tall channel chip with no cells in the top channel but with hSkMCs in the bottom channel. Group 3: shows a schematic illustration of the tall channel chip with diMNs in the top channel and hSkMCs in the bottom channel for providing a NMJ-on-Chip.

FIG. 10B: shows a schematic illustration of cells numbers and media used for growing cells:

Group 1: Top: $3\times10^6$ diMNs Bottom: none. Group 2: Top: none. Bottom: $10\times10^6$ hSkMCs. Group 3: Top: $3\times10^6$ diMNs. Bottom: $20\times10^6$ hSkMCs.

FIG. 11: Shows human skeletal muscle cells (hSkMCs) forming myofibers within 8 days post seeding (co-cultures) having spontaneous myo-tube contractions at Day (D) 10 culture that are reduced by using conM culture medium in a microfluidic chip.

FIG. 11A: shows micrographs of hSkMCs growing in chips. White arrows in the magnified region point to multinucleated muscle cell fibers, of which there appears to be more nuclei per fiber in the coM medium;

FIG. 11B: shows micrographs of diMNs growing in chips; and

FIG. 11C: shows micrographs of shSkMCs/diMNs grown in MN/hSkMCs media (upper row of micrographs) and coM medium (lower row of micrographs) growing in chips. Spontaneous myo-tube contraction was observed only in diMNs/hSKMC co-cultures. White arrows in the magnified region point to contacts of MN with a muscle cell fiber.

Inserts show higher magnified areas of cells outlined in the white box for each micrograph.

FIG. 12: Shows human skeletal muscle cells (hSkMCs) as myofibers with spontaneous myotube contraction at Day (D) 10 (Experiment 3).

FIG. 12A: shows a micrograph of hSkMCs as myotubes growing on top of a membrane of the microfluidic chip in coM media.

FIG. 12B: shows a graph comparing contractions per minute for a myofiber contraction frequency with an average of fibers in two experiments (Experiment 1 and 3) that were combined for a total estimation of myofiber contraction frequency.

FIG. 12C: shows a graph comparing contractions per minute for myofibers having an increased myofiber contraction frequency between Laminin vs. cross linked Laminin ECM, at about the same frequency as shown in FIG. 12B.

FIG. 12D: shows a graph comparing contractions per minute for myofibers grown in regular media compared to a culture grown in coM media. When cultured in coM, contraction frequency is around 25% less compared to regular medium conditions.

FIG. 13: shows schematic illustrations of experimental timelines for comparing co-cultures of hSkMCs with MNs, with and without coM media.

FIG. 13A: shows a schematic illustration of a timeline and cell densities for Group 1 and Group 2 in coM: hSkMCs seeded at $5\times10^6$/ml cells and MNs seeded at $3\times10^6$/ml cells. hSkMCs seeded Day (D) 0 with differentiation (diff) initiated on D1, Day 12 MNs seeded D1 (as one example 18h later), D5 formation of myotubes & medium switch to coM, no myofiber contractions observed D10, no loss of myofibers observed on D12, fixation and analysis by ICC on D14, duplicate chips on D20 showed no loss of myofibers.

FIG. 13B: shows a schematic illustration of a timeline and cell densities for Group3: hSkMCs seeded with MNs: Day 0: seeding hSkMCs; Day 1: (18 h later) seeded diMNs (d12); Day 5: formation of myotubes, no medium switch; Day 10: observation of myofiber contraction; Day 11: observing progressive loss of myofibers; Day 14: fixation and analysis by ICC; in chip cultures left to D20, there is almost a complete loss of myofibers.

Thus, exemplary steps for providing a functional NMJ-on-Chip by combining motor-neurons on a chip (upper blue channel) with skeletal muscle cells on a chip (lower-red) channel include: Seeding the bottom (lower-blue) channel as a skeletal muscle-on-chip capable of producing contractile muscle tissue expressing markers myosin heavy chain (MHC) (green), pre-BTX (α-bungarotoxin) (red) identified by immunohistochemistry and stained for DNA (blue) shown by fluorescent microscopy. Seeding the upper channel of the microfluidic chip with patient iPSC-derived MNs that under chip culture conditions will express neuronal expressing markers Neuron-specific Class III β-tubulin (TuJ1) (red), selectivity/selective factor 1 complex (for RNA polymerase) (SL1) (blue), homeobox B9 (HOXB9) (red), identified by immunohistochemistry (IHC) as shown by fluorescent microscopy. In some embodiments, spontaneous contractions may be stopped by adding calcium channel blockers or sodium channel blockers to the culture media.

Example 6

This example shows embodiments of exemplary co-localization of MNs and muscle cells showing potential formation of NMJs in microfluidic NMJ-on-chip.

FIG. 14: shows florescent micrographs of stained cells in a microfluidic chip. Co-Localization Study of iPS-Derived MNs and Muscle Cells. Both diMNs and hSKMCs are in close proximity to each other as determined from initial ICC analysis and 3D reconstruction of confocal microscope images (i.e. combined z-stacks). A partial loss of myotubes were observed due to lack of ECM stability FIG. 14A and FIG. 14B: α-bungarotoxin (BTX) for identifying the motor end plate (green), skeletal muscle marker, desmin, (red) and DNA (DAPI) (shown in blue). The red muscle fiber is multinucleated with numerous green motor end plates.

FIG. 14B: a higher magnification of FIG. 14A, 3 white arrows point to co-localization of α-bungarotoxin (BTX) for identifying the motor end plate (green) and skeletal muscle marker, desmin, (red) as olive, white dark orange areas depending upon concentration of stain.

FIG. 14C and FIG. 14D: motor end plate (green) BTX and neurofilament H non-phosphorylated (SMI 32) (red) and DNA (DAPI) (shown in blue).

FIG. 14D: a higher magnification of FIG. 14C, 3 white arrows point to co-localization of a motor end plate (green) BTX, neurofilament H non-phosphorylated (SMI 32) (red) as olive—white areas depending upon concentration of stain.

Example 7

This example describes using Microfluidic NMJ-On-Chip Under Flow For Longer Studies.
Experiment 4: Extended cultures up to day 37.
Experiment 4 showed that hSkMC integrity in chip is expandable over time (in monoculture).
FIG. 17: shows schematic illustrations of tall channel microfluidic NMJ-on-chip with one embodiment of an experimental timeline (Experiment 4) set up and time course for comparing co-cultures of hSkMCs with MNs under flow.

FIG. 17A: shows a schematic illustration of a tall channel microfluidic chip, from left to right, view of vertical 2-channel chip (i.e. the top channel is above the bottom channel as shown in Stage 1, with hSkMCs covering the entire surface of the bottom channel, and Stage 2 with diMNs seeded into the top channel.

FIG. 17B: shows a schematic illustration of one embodiment of a timeline where hSkMCs are seeded Day (D) 0 with differentiation (diff) initiated on D1, D5: formation of myotubes & medium switch to coM media, then Day 7-10: no myofiber contraction, on Day 20 start muscle cells under flow at 10 ul/hour, continued to D29 when flow is stopped. Day 30: seed diMNs (d12) (not in coM media for observing baseline contractions). Day 37: myotubes are spontaneously contracting: fixation and analysis (including ICC).

FIG. 18: shows an exemplary co-localization study of iPS-Derived MNs and Muscle Cells showing formation of NMJs between diMNs and hSkMCs (Experiment 4). Cells were stained with α-bungarotoxin (BTX) for identifying suggestive NMJ areas where motor end plate (green), neurons are stained with Tubulin beta-3 chain (Tubb3) (red) and muscle myosin heavy chain (MHC) (blue) were fluorescently imaged on individual channels then merged. The blue channel of MHC staining is not shown in FIG. 12A-12D.

FIG. 18A: shows a low power fluorescent micrograph where Tubb3 (red) neuronal staining shows neurite extension along myotubes with oval areas (green) suggestive of lower motor nerve termini whose distribution over a myotube suggests motor end plates.

FIG. 18B-G: shows higher power fluorescent micrographs of the suggestive NMJ areas (white arrows) are identified by superimposed staining i.e. co-localization, where the red stained nerve terminal neuron bulb is co-localized with BTX green staining of motor end plates producing a yellow NMJ. FIG. 18E-18G: The blue channel of MHC staining is shown showing a MHC containing muscle fiber at the yellow stained NMJ.

Example 8

In this example a microfluidic NMJ-on-chip described for pharmacology studies and live imaging of cells within channels (Experiment 5).

In this embodiment, an experimental time line (course) is described for seeding hSkMCs up to 9 days prior to seeding MNs in the upper channel. Spontaneous contractions are allowed to begin by removing CoM media at the start of the pharmacology assay.

Experiment 5 showed that pharmacology and imaging was possible for measuring functional NMJ interactions.

FIG. 19: shows schematic illustrations of one embodiment of experimental timelines for using NMJ-on-chips (Experiment 5) as a set up and time course for using co-cultures of hSkMCs with MNs for live imaging and pharmacology studies.

FIG. 19A: shows a schematic illustration of a tall channel microfluidic chip, seeded with hSkMCs at Day 0 (D0) in the bottom channel, culting up to D9, without observing muscle contractions, then D9 seeding diMNs (d12). In one embodiment only in Group 2. In some embodiments, more than one group of hSkMCs receive MNs. On days 15, 16 and/or 17, live imaging of pharmacology assays are done as shown schematically, for one example, in FIG. 19B.

FIG. 19B: shows a schematic illustration of one embodiment of a timeline where a NMJ-On-Chip with spontaneous contracting muscle fibers is used for a pharmacology study, i.e. testing agents for inducing or reducing muscle contractions on a baseline chip with or without spontaneously contracting myofibers, in one embodiment, treating NMJ chip with 75 uM Glutamine (Glut) in the NM (upper) channel), in one embodiment, treating NMJ chip with 12 uM alpha-turbocurarine in the hSkMC (lower) channel), in one embodiment, washing out alpha-turbocurarine, in one embodiment, treating NMJ chip with 100 uM Glutamine (Glut) in the NM (upper) channel).

FIG. 20: Shows exemplary High Content Imaging as immunohistochemistry of iPSC derived Myo-fibers, on fixed cells (Experiment 5).

FIG. 20A: shows a fluorescent micrograph of the entire width and length of immunostained cells in a microfluidic NMJ chip. α-bungarotoxin BTX (green), Neuron-specific Class III β-tubulin (TuJ1) (red) and myosin heavy chain (MHC) (blue).

FIG. 20B: shows a higher power fluorescent micrograph of the channel in the chip shown in FIG. 20A.

FIG. 21: shows micrographs of cells grown as shown in Experiment 5 for pharmacology and in-chip imaging for NMJ-On-Chip.

FIG. 21A: shows phase contrast micrographs of myotubes and neurons in chips, higher magnified areas are shown below the larger micrograph white arrows point to potential NMJs where myotubes are adjacent to neurons.

FIG. 21B: shows fluorescent micrographs of superimposed (co-localized images) of neurons stained with a neuronal microtubule marker, Tau, (green) a microtubule stabilization protein, for identifying neurons and motor end plates with BTX (red) (labeling AChRs) for identifying NMJs, where neuronal braches co-localize with end plates. Smaller micrographs show higher magnified areas outlined by corresponding white boxes. White arrows point to motor end plates of myotubes, some of which are in close proximity to neuronal axons.

FIG. 22: shows an exemplary method of growing motor neurons in a microfluidic chip where the MN cells of neural networks have spontaneous calcium bursts. Experiment 5.

FIG. 22AA: shows a microfluidic chip seeded with MNs at day 12 of culture.

FIG. 22BB: shows an exemplary timeline where MN precursor cells from Day 12 cultures are seeded at Day 0 in the microfluidic chip, MN network formation is observed a Day 10 on the chip (Day 18 overall from the start of the original MN culture).

FIG. 22CC: shows exemplary images produced by high content life imaging of cells in chips showing Ca++ imaging of diMN cells on Day 12 after seeding onto the microfluidic chip; at high magnification (20×). diMNs show repetitive calcium bursts as visualized via Flou4 labeling in color within the cellular areas, e.g. cell bodies, axons and terminal bulbs, in neuronal networks, where the concentrations of Ca++ are shown by yellow-lower levels, red-higher than yellow areas and highest levels in white areas within the red areas, as shown in the neuron cell bodies.

FIG. 22A: shows exemplary Ca++ imaging of FIG. 22CC in black and white, where the highest amounts of Ca++ are white areas in black and white micrographs, white arrowheads point to cellular areas with concentrated Ca++.

FIG. 22B: shows a higher magnification of a cell in the center of the micrograph in FIG. 22CC/FIG. 22A with two white arrowhead markers used to identify the same area through the different planes of focus.

FIGS. 22D-22J: shows exemplary Ca++ imaging in color from confocal high content micrograph z-stack layers through the cell (shown in FIG. 22B) where higher concentrations of Ca++ are shown by yellow/red/white areas in the neuronal cytoplasm, which discharge and recharge then discharge over time. White arrowheads mark the same location of the cell shown in FIG. 22B-FIG. 22J.

FIG. 22K: shows a graph of average intensity of Ca++ vs. elapsed time (seconds).

Example 9

Alternative Configurations

In alternative configurations, iPSC derived motor neurons can be introduced into a XONA™ microfluidic device. Cells were labeled using MitoTracker green as shown in FIGS. 24 and 25. iPSC derived motor neurons seeded in this manner in the microfluidic device, exhibited capacity for axonal retraction. with timelapse of axonal retraction at approximately 1, 2, 3, 4, 6, 9, 11, 13 and 16 hour timepoints as indicated as in FIGS. 26 and 27.

As shown in FIG. 28, iPSC-motor neurons "co-culture" in microfluidic device: control (CTR). Microfluidic device, such as optically transparent and biologically inert Polydimethylsiloxane (PDMS) possesses multiple chambers connected by microgrooves. The chamber allows fluidic communication with different cell types. Hydrostatic pressure between the two chambers separated by the microgrooves can allow one to fluidically isolate each chamber by keeping the volumes in the wells on one side of the device higher than the other side of the device. The difference in volume creates hydrostatic pressure, thus fluidically isolating each compartment. Control cells are seeded here for illustration. For comparison iPSC-motor neurons derived from spinal muscular atrophy (SMA) patients can be "co-culture" in microfluidic device as shown in FIG. 29. As shown in FIG. 30, iPSC-motor neurons "co-culture" in microfluidic device: control (CTR). Various labeling agents, including a-bungarotoxin (BTX), synaptic vesicle 2 (SV2) can aid visualization of the neuromuscular junction including co-localization of these markers as depicted. As shown in FIG. 31 iPSC-motor neurons "co-culture" in microfluidic device results in formation of muscular cells aggregated and in connection with neuron projections, across microgrooves.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the methods for generating motor neurons, skeletal muscle cells, neuromuscular junction, methods and compositions related to the aforementioned techniques, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A neuromuscular junction generated on a microfluidic device (NMJ-on-chip) comprising:
   one or more human induced pluripotent stem cell (iPSC)-derived neurons seeded into an upper channel or a lower channel of the microfluidic device; and
   one or more human iPSC-derived muscle cells seeded into the upper channel or the lower channel of the microfluidic device, wherein the one or more human iPSC-derived muscles cells are not in the same channel as the one or more human iPSC-derived neurons,
   wherein the one or more neurons are capable of generating a nerve action potential and inducing spontaneous contraction in the one or more muscle cells,
   wherein the microfluidic device comprises a culture media including Compound E, DAPT, db-cAMP, Ascorbic Acid, Glial cell-derived neurotrophic factor (GDNF), Brain-derived neurotrophic factor (BDNF), and VPA (valproic acid), and
   wherein the culture media lowers spontaneous contraction rates of myofibers or myotube formed from the one or more muscle cells, the myofibers or myotube growing on top of a membrane of the NMJ-on-chip, and the membrane separating the upper channel and the lower channel.

2. The NMJ-on-chip of claim 1, wherein said one or more human iPSC-derived neurons are from a human diagnosed with a neuron disease and/or condition.

3. The NMJ-on-chip of claim 1, wherein said one or more human iPSC-derived muscle cells are from a human diagnosed with a muscle disease and/or condition.

4. The NMJ-on-chip of claim 1, wherein the spontaneous contraction is allowed to begin by removing the culture media.

5. The NMJ-on-chip of claim 1, wherein the one or more neurons are seeded into the upper channel, and the one or more muscle cells are seeded into the lower channel.

6. The NMJ-on-chip of claim 1, wherein the one or more neurons and the one or more muscle cells are from a same patient.

7. The NMJ-on-chip of claim 6, wherein the patient is an amyotrophic lateral sclerosis (ALS) patient.

8. The NMJ-on-chip of claim 1, wherein the culture media further comprises a blocker to stop the spontaneous contraction.

9. The NMJ-on-chip of claim 8, wherein the blocker comprises a calcium channel blocker, a sodium channel blocker, or tetrodotoxin (TTX).

10. The NMJ-on-chip of claim 1, wherein the culture media-further includes all-trans RA and purmorphamine or SAG.

11. The WJ-on-chip of claim 10, wherein the culture media further includes Iscove's Modified Dulbecco's Media/Ham's F-12 Nutrient Mixture (IMDM/F12), Non- Essential Amino Acids (NEAA), B27 supplement (B27), N-2 Supplement (N2), and PSA.

12. The NMJ-on-chip of claim 1, wherein the culture media prevents loss of the myofibers or myotube.

13. The NMJ-on-chip of claim 1, wherein the seeded one or more neurons and one or more muscle cells are exposed to a flow of the culture media for a period of time.

14. The NMJ-on-chip of claim 13, wherein the seeded one or more neurons and one or more muscle cells are cultured under conditions such that the neuromuscular junction forms within the microfluidic device.

15. The NMJ-on-chip of claim 1, wherein the culture media flows into the upper and lower channels such that the one or more neurons and the one or more muscle cells are perfused.

16. The NMJ-on-chip of claim 11, wherein the culture media further includes 2% fetal bovine serum (FBS).

* * * * *